United States Patent
Young et al.

(10) Patent No.: US 6,436,628 B1
(45) Date of Patent: *Aug. 20, 2002

(54) METHODS OF IDENTIFYING AN AGENT WHICH MODULATES PERIOD AND DOUBLETIME PROTEIN INTERACTION

(75) Inventors: Michael W. Young, Old Tappan, NJ (US); Brian Kloss; Justin Blau, both of New York, NY (US); Jeffrey Price, Kansas City, MO (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/335,983

(22) Filed: Jun. 18, 1999

Related U.S. Application Data

(60) Provisional application No. 60/090,068, filed on Jun. 19, 1998.

(51) Int. Cl.[7] .......................... C12Q 1/00; A01N 37/18; A01N 61/00; G01N 33/53

(52) U.S. Cl. .................................. 435/4; 435/7.1; 514/2

(58) Field of Search ............................ 435/7.1, 184, 4; 530/350, 352; 930/350; 514/2

(56) References Cited

U.S. PATENT DOCUMENTS 5,885,831 A * 3/1999 Young et al.
6,057,129 A * 5/2000 Young et al. ............... 435/69.1

FOREIGN PATENT DOCUMENTS

WO    WO 00/75669 A1    12/2000

OTHER PUBLICATIONS

Harvey, Genbank Accession No. AA567638 (Dec. 18, 1997).*
Marrus et al., EMBO Journal, vol. 15, No. 24., pp. 6877–6886, 1996.*
Geysen et al. Cognitive features of continuous antigenic determinants. Journal of Molecular Recognition, vol. 1, pp. 32–41, 1988.*
Russell et al., Journal of Molecular Biology, vol. 244, pp. 332–350, 1994.*
Gerhold et al., BioEssays, vol. 18, No. 12, pp. 973–981, 1996.*
Wells et al., Journal of Leukocyte Biology, vol. 61, No. 5, pp. 545–550, 1997.*
Albrecht et al. Cell, 91:1055–1064 (1997).
Altschul et al., J. Mol. Biol. 215:403–410 (1990).
Bargiello et al Proc. Natl. Acad. Sci. U.S.A. 81:2142–6 (1984).
Baylies et al. in Molecular Genetics of Biological Rhythms, pp. 123–153, M. W. Young, Ed. (Dekker, New York, 1993).
Cavener, NAR, 15:1353–1361 (1987).
Crews et al Cell 52:143–51 (1988).
Crosthwaite et al., Science, 276:763–769 (1997).
Curtin et al., Neuron, 14:365–372 (1995).
Dembinska et al., J. Biol. Rhythms, 12:157–172 (1997).
Dunlap et al., Annu. Rev. Genet., 30:579–601 (1996).
Edery et al Proc. Natl. Acad. Sci. U.S.A 91:2260–4 (1994).

(List continued on next page.)

Primary Examiner—Ardin H. Marschel
(74) Attorney, Agent, or Firm—Klauber & Jackson

(57) ABSTRACT

The present invention provides isolated nucleic acids and/or recombinant DNA molecules that encode the clock protein DOUBLETIME. The present invention further provides both isolated and/or recombinant DOUBLETIME. In addition, the present invention provides antibodies to DOUBLETIME. Methods of using the nucleic acids, proteins and antibodies of the present invention, including as therapeutics are also provided.

25 Claims, 17 Drawing Sheets

OTHER PUBLICATIONS

Ewer et al., *J. Neurosci.*, 12:3321–3349 (1992).
Fish et al., *Journ.BiolChem*, 270:14875–14883 (1995).
Frisch et al., *Neuron*, 12:555–570 (1994).
Gekakis et al., *Science*, 270:811–815 (1995).
Giebultowicz and Hege, *Nature*, 386:664 (1997).
Hamilton et al., *NAR*, 19:1951–1952 (1991).
Hanks et al., *Science* 241: 42–54 (1988).
Hardin et al, *Proc. Natl. Acad. Sci. U.S.A.* 89:11711 (1992).
Hardin et al, *Nature* 343:536–40 (1990).
Helfrich–Forster, *Proc. Natl. Acad. Sci. USA*, 92:612–616 (1995).
Huang et al *Nature* 364:259–72 (1993).
Hunter–Ensor et al., *Cell*, 84:677–685 (1996).
Jackson, in *Molecular Genetics of Biological Rhythms*, pp. 91–121, M. W. Young, Ed. (Dekker, New York, 1993).
James et al *EMBO J.* 5:2313 (1986.
Kaneko et al., *Neurosci.*, 17:6745–6760 (1997).
Kelley et al., *Mol. and Cell Bio.*, 7:1545–1548 (1987).
King et al., *Cell*, 89:641–653 (1997).
Kondo et al., *Sicience*, 266:1233–1236 (1994).
Konopka and Benzer *Proc. Natl. Acad. Sci. U.S.A.* 68:2112 (1971).
Kunes et al. *J. Neurosci.*, 13:752–767 (1993).
Lee et al., *Science*, 271:1740–1744 (1996).
Leloup and Goldbeter, *J. Biol. Rhythms*, 13:70–87 (1998).
Millar et al., *Science*, 267:1161–1163 (1995).
Myers et al., *Science*, 271:1736–1740 (1996).
Myers et al., *Nucl. Acids Res.*, 25:4710–1714 (1997).
Nambu et al *Cell* 67:1157–67 (1991).
Pettendrigh, in *Handbook of Behavioral Neurobiology*, 4, J. Achoff, Ed.., New York: Plenum, 1981, pp. 95–124.
Price et al., *EMBO J.*, 14:4044–4049 (1995).
Ralph and Menaker, *Science*, 241:1225–1127 (1988).
Rosbash et al., Cold Spring *Harb. Symp. Quant. Biol.*, 61:265–278 (1996).
Rutila et al., *Neuron*,17:921–929 (1996).
Saez and Young, *Neuron*, 17:911–920 (1996).
Sehgal et al., *Proc. Natl. acad. Sci. USA*, 89:1423–1427 (1992).
Sehgal et al. *Science* 263:1603 (1994).
Sehgal et al. *Science*, 270:808–810 (1995).
Siwicki et al *Neuron* 1:141–50 (1988).
Stanewsky et al., *J. Neurosci.*, 17:676–696 (1997).
Sun et al., *Cell* 90:1003.1011 (1997).
Tautz and Pfeifle Chromosoma 98:81–85 (1989).
Tei et al., *Nature*, 389 (1997) pp. 512–516.
Vitaterna et al., *Science*, 264:719–725 (1994).
Vosshall et al., *Science*, 263:1606–1609 (1994).
Vosshall and Young, *Neuron*, 15:345–360 (1995).
Zeng et al., *Nature*, 380:129–135 (1996).

* cited by examiner

+ / +, tau=24.0 hrs $dbt^S$ / +, tau=21.5 hrs $dbt^S$ / $dbt^S$, tau=18.0 hrs

+ / +, tau=23.5 hrs $dbt^L$ / +, tau=25.0 hrs $dbt^L$ / $dbt^L$, tau=27.0 hrs

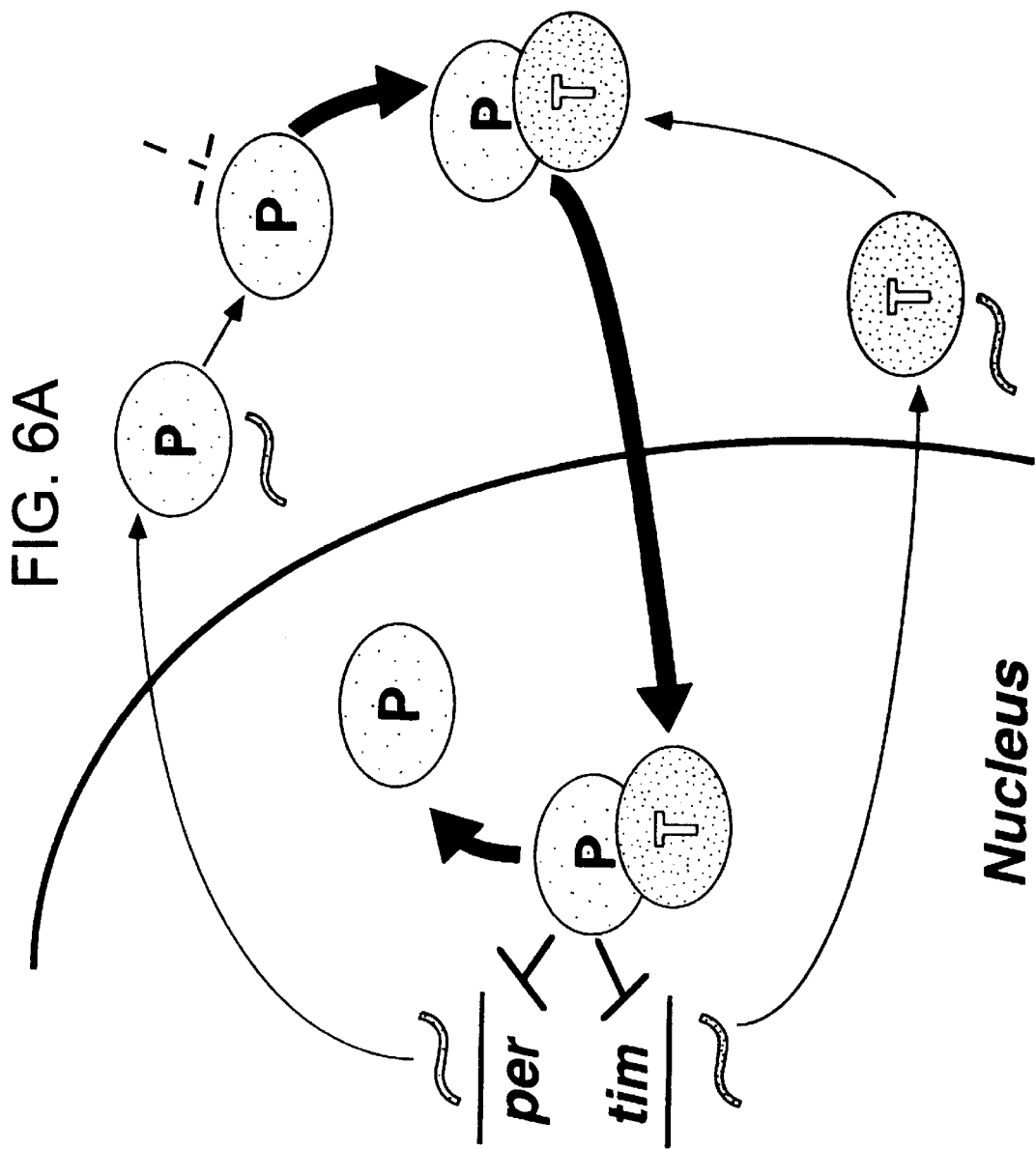

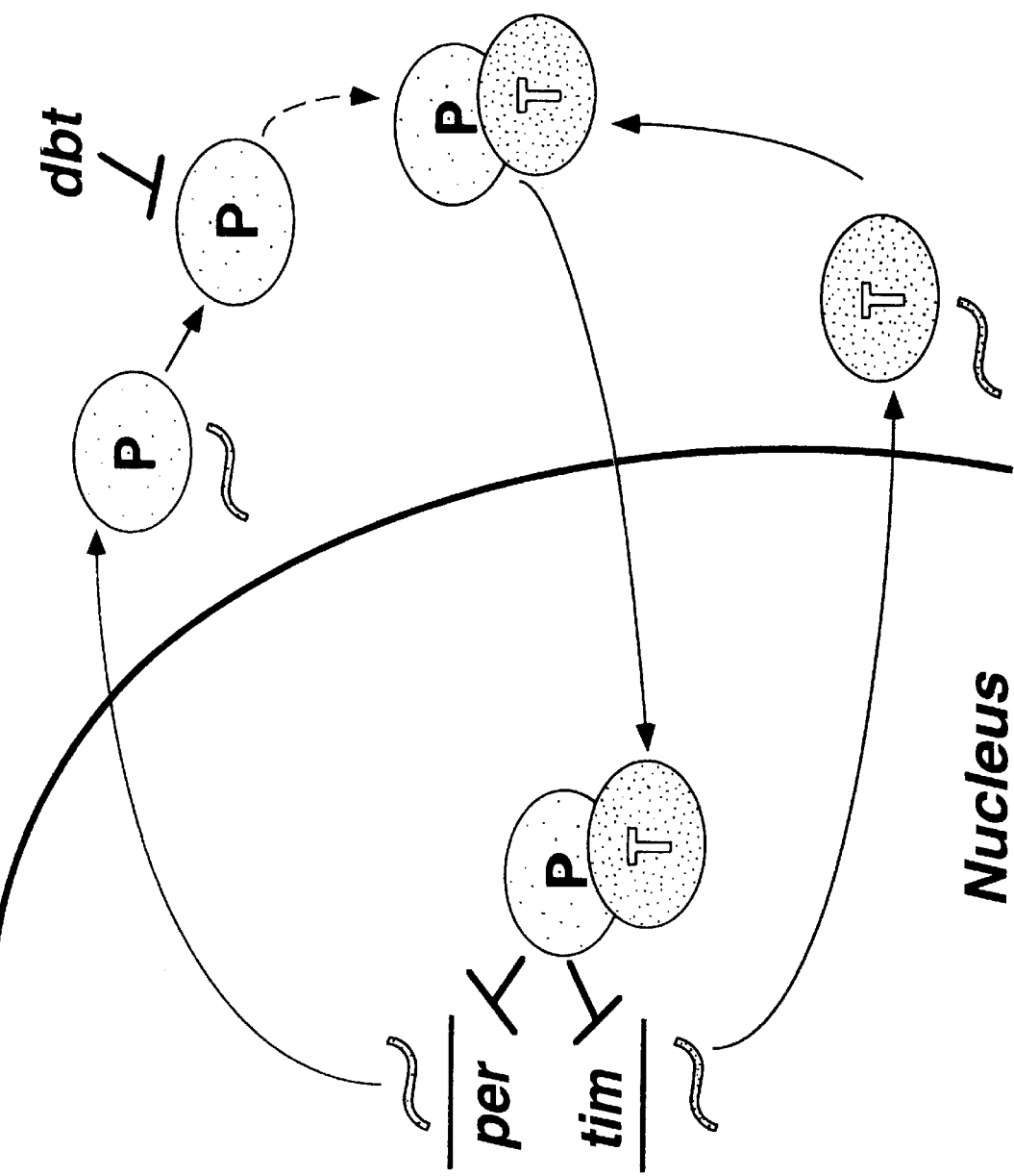

FIG. 11A

```
                        start                                          ATP-binding
DBT
H. sapiens     ------ELRVGNKYRLGRKIGSSFGDIYLGTTINTGEEVAIKLECIRTKHPQLHIE  52
A. thaliana    .-----ELRV.N.YRLG..........DI..GANIAS.......I..CVKTK...HI.  52
X. laevis      -----DLVI.G.FKLG..........EL..GINVQT.......V..SVKTK...HY.  52
G. gallus      ASSSGSKAEFIV.G.YKLV.......DI..AINITN.......V..SQKAR...LY.  60
S. pombe       ASSSGSKAEFIV.G.YKLV.......DI..AINITN.......V..SQKAR...LY.  60
               A-----LDLRI.N.YRIG..........DI..GTNVVS.......I..STRAK...EY.  54
                                                                    DBT^S
                                                                      [S]

DBT                                                                DBT^L
H. sapiens     SKFYKTMQGGIGIPRIIWCGSEGDYNVMMELLGPSLEDLFNFCSRRFSLKTVLLLADQM  112
A. thaliana    SKF.KMMQ...V.I.SIK.C.A.G....VM.ME...............F.S.KFSL...L....M  112
X. laevis      SKL.MLLQ...T.V.NLK.Y.V.G....VM.ID...............Y.N.KLSL...M....L  112
G. gallus      SKL.KILQ...V.I.HIR.Y.Q.K....VL.MD...............F.S.RFTM...M....M  120
S. pombe       SKL.KILQ...V.I.HIR.Y.Q.K....VL.MD...............F.S.RFTM...M....M  120
               YRV.RILS...V.I.FVR.F.V.C....AM.MD...............F.N.KFSL...L....L  114
                                              [I]
                                                          catalytic
DBT
H. sapiens     ISRIDYIHSRDFIHRDIKPDNFLMGLGKKGNLVYIIDFGLAKKFRDARSLKHIPYRENKN  172
A. thaliana    .S.IEYI.SKN.I.....V...................L.KKG.LVYI.....A..YRDARTHQ.......N...  172
X. laevis      .N.VEFM.TRG.L....I....................L.RKA.QVYI.....G..Y..LQTHR.......N...  172
G. gallus      .S.IEYV.TKN.I....I....................I.RHC.KLFL.....A..Y..NRTRQ.......D..  180
S. pombe       .S.IEYV.TKN.I....I....................I.RHC.KLFL.....A..Y..NRTRQ.......D..  180
               .S.IEFI.SKS.L....I....................I.KRG.QVNI.....A..Y..HKTHL.......N..  174
```

FIG. 11B

```
DBT          LTGTARYASINTHLGIEQSRRDDLESLGYVLMYFNLGALPWQGLKAANKRQKYERISEKK 232
H. sapiens   .........I.T....I.........L.S......M..NLGS........AT.R...ER.S... 232
A. thaliana  .........V.T....V.........L.A......M..LKGS........GT.K...DR.S... 232
X. laevis    .........I.A....I.........M.S......M..NRTS........AT.K...EK.S... 240
G. gallus    .........I.A....I.........M.S......M..NRTS........AT.K...EK.S... 240
S. pombe     .........I.T....I.........L.S......V..CRGS........TT.K...EK.M... 234

DBT          LSTSIVVLCKGFPSEFVNYLNFCRQMHFDQRPDYCHLRKLFRNLFHRLGFTYDYVFDWNL 292
H. sapiens   MS.PIE...KGY.S...ST.LNFC.SLR.DDK...SY.RQ...N..HRQGFSY..V...NM 292
A. thaliana  VA.PIE...KNQ.S...VS.FRYC.SLR.DDK...SY.KR...D..IREGYQF..V...TV 292
X. laevis    MS.PVE...KGF.A...AM.LNYC.GLR.EEA...MY.RQ...I..RTLNHQY.T...TM 300
G. gallus    MS.PVE...KGF.A...AM.LNYC.GLR.EEA...MY.RQ...I..RTLNHQY.T...TM 300
S. pombe     IS.PTE...RGF.Q...SI.LNYT.SLR.DDK...AY.RK...D..CRQSYEF.M...TL 294

DBT          LKFGGPRNPQAIQQAQDGADGQAGHDAVAAAAVAAAAASSHQQQHKVNAALGGGGGS 352

DBT          RAQQQLQGGQTLAMLGGNGGGNGSQLIGGNGLNMDDSMAATNSSRPPYDTPERRPSIRMR 412

DBT          QGGGGGGGVGVGMQSGGGGGVGNAK 440
```

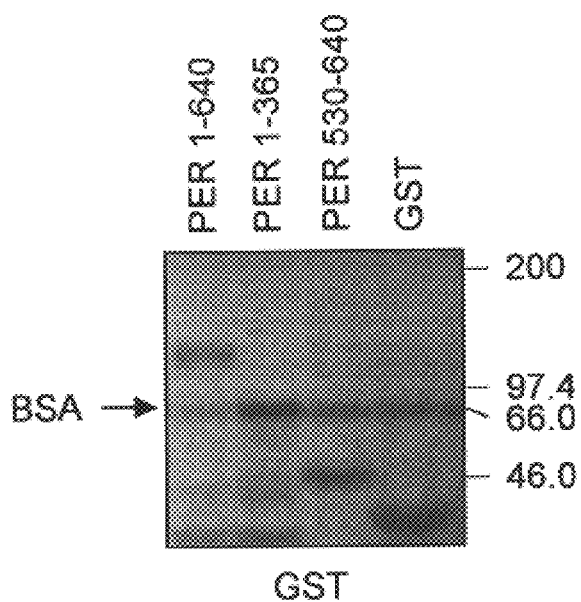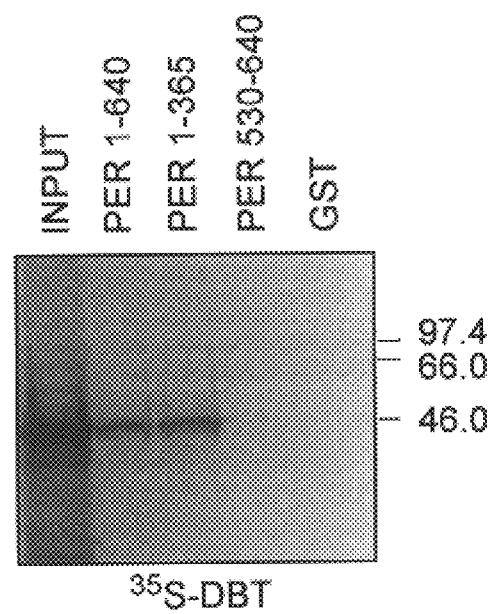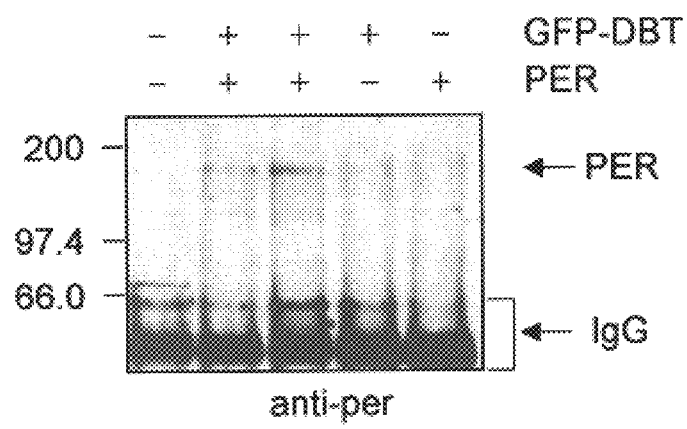

METHODS OF IDENTIFYING AN AGENT WHICH MODULATES PERIOD AND DOUBLETIME PROTEIN INTERACTION

CROSS-REFERENCE TO RELATED APPLICATIONS

The present application is a non-provisional application claiming the priority of copending provisional U.S. Ser. No. 60/090,068 filed Jun. 19, 1998, the disclosure of which is hereby incorporated by reference in its entirety. Applicants claim the benefits of this application under 35 U.S.C. §119(e).

GOVERNMENTAL SUPPORT

The research leading to the present invention was supported, at least in part, by a grant from NIH Grants GM 54339 and NIH MH 56895. Accordingly, the Government may have certain rights in the invention.

FIELD OF THE INVENTION

This invention relates to a protein involved in the nuclear localization of proteins, and more specifically to a protein involved in maintaining circadian rhythms. The invention also relates to mutants of the protein, nucleic acid and amino acid sequences encoding the purified protein itself, as well as methods of using the protein.

BACKGROUND OF THE INVENTION

Patterns of activity with periodicities of approximately 24 hours are termed circadian rhythms, and are governed by an internal clock that functions autonomously, but can be entrained by environmental cycles of light or temperature. These behaviors can be entrained to a "zeitgeiber" (most commonly light), but are sustained under conditions of constant darkness and temperature, revealing activity of an endogenous biological clock. Circadian rhythms produced in constant darkness, for example, can also be reset by pulses of light. Such light pulses will shift the phase of the clock in different directions (advance or delay) and to varying degrees in a fashion that depends on the time of light exposure [Pittendrigh, in *Handbook of Behavioral Neurobiology*, 4, J. Aschoff, Ed., New York: Plenur, 1981, pp. 95–124].

Circadian rhythms appear to be a universal component of animal behavior [Pittendrigh, C. S., *Proc. Natl. Acad. Sci USA*, 58:1762–1767 (1967); Pittendrigh, C. S., *Neurosciences*, 437–458 (1974)]. Indeed, circadian physiological rhythms are not limited to the animal kingdor, and genetic screens have identified clock genes in Drosophila [Konopka and Benzer, *Proc. Natl. Acad. Sci. USA*, 68:2112–2116 (1971); and Sehgal et al., *Science*, 263:1603–1606 (1994)], Chlamydomonas [Bruce, V. G. *Genetics*, 70:537–548 (1972)], Neurospora [Feldman and Hoyle, *Neurospora crassa Genetics*, 75:605–613 (1973); Crosthwaite et al., *Science*, 276:763–769 (1997)], Cyanobacteria [Kondo et al., *Sicience*, 266:1233–1236 (1994)], Arabidopsis [Millar et al., *Science*, 267:1161–1163 (1995)], hamster [Ralph and Menaker, *Science*, 241:1225–1127 (1988)], and mouse [Vitaterna et al., *Science*, 264:719–725 (1994)].

Fruit flies show circadian regulation of several behaviors [Pittendrigh in *The Neurosciences Third Study Program*, Chap. 38, F. O. Schmitt and F. G. Worden, Eds. (MIT Press, Cambridge Mass., 1974); Jackson, in *Molecular Genetics of Biological Rhythms*, pp. 91–121, M. W. Young, Ed. (Dekker, N.Y., 1993)]. When populations of Drosophila are entrained to 12 hours of light followed by 12 hours of darkness (LD 12:12), adults emerge from pupae (eclose) rhythmically, with peak eclosion recurring every morning. The eclosion rhythm persists when the entraining cues are removed and behavior is monitored in constant darkness, thus indicating the existence of an endogenous clock. Adult locomotor activity is also controlled by an endogenous clock and recurs rhythmically with a 24-hour period.

In the fruit fly *Drosophila melanogaster*, two genes are essential components of the circadian clock, period and timeless [Sehgal et al. *Science* 263:1603 (1994)]. Mutations in either of these genes can produce arrhythmicity or change the period of the rhythm by several hours [Konopka and Benzer *Proc. Natl. Acad. Sci. U.S.A.* 68:2112 (1971); Sehgal et al *Science* 263:1603 (1994)]. Molecular studies [Bargiello et al *Proc. Natl. Acad. Sci. U.S.A.* 81:2142 (1984); Reddy et al *Cell* 38:701 (1984); Myers *Science* 270:805 (1995); Hardin et al. *Nature* 343:536 (1990); Sehgal et al., *Science*, 270:808–810 (1995)1 have shown that per and tim are transcribed with indistinguishable circadian rhythms that are influenced by an interaction of the TIM and PER proteins [Sehgal et al. *Science* 263:1603 (1994); Gekakiset et al *Science*, 270:811 (1995)]. A physical association of the two proteins appears to be required for accumulation and nuclear localization of PER [Sehgal et al *Science* 263:1603 (1994); Gekakiset et al. (1995); Price et al. *EMBO J.*, 14:4044 (1995)]. It is likely that nuclear localization leads to suppression of per and tim transcription [Hardin et al. *Nature*, 343:536 (1990); Sehgal et al., *Science*, 270:808–810(1995)]. Cycles of gene expression are thought to be sustained by '5 hour differences in the phases of RNA and protein accumulation. The observed delays in PER accumulation may result, in part, from a requirement for TIM to stabilize PER [Sehgal et al *Science* 263:1603 (1994); Sehgal et al. *Science*, 270:808–810(1995); Price et al. *EMBO J.*, 14:4044–4049 (1995)].

More specifically, mutations in the Drosophila period (per) gene, for example, disrupt circadian rhythms of pupal eclosion and adult locomotor behavior [Konopka and Benzer *Proc. Natl. Acad. Sci. U.S.A.* 68:2112 (1971)]. Although per has been cloned and sequenced and its pattern of expression has been analyzed [Baylies et al. in Molecular Genetics of Biological Rhythms, pp. 123–153, M. W. Young, Ed. (Dekker, N.Y., 1993); Rosbash and Hall *Neuron* 3:387 (1989)], the biochemical function of the PER protein is unknown. PER shares some homology with a family of transcription factors [Crews et al *Cell* 52:143 (1988); Nambu et al *Cell* 67:1157 (1991); Reisz-Porszasz et al *Science* 256:1193 (1992); Hoffman et al *Cell* 252:954 (1991); Burbach et al *Proc. Natl. Acad. Sci. U.S.A.* 89:8185 (1992)] that possess a common sequence motif called the PAS domain.

Imunocytochemical experiments demonstrated that PER is a nuclear protein in a variety of Drosophila tissues [Konopka and Benzer *Proc. Natl. Acad. Sci. U.S.A.* 68:2112 (1971); Baylies et al in *Molecular Genetics of Biological Rhythms*, pp. 123–153, M. W. Young, Ed. (Dekker, N.Y., 1993)]. In cells of the adult fly visual and nervous systems, the amount of PER protein fluctuates with a circadian rhythm [Edery et al *Proc. Natl. Acad. Sci. U.S.A* 91:2260 (1994)], the protein is phosphorylated with a circadian rhythm [Edery et al., *Proc. Natl. Acad. Sci. U.S.A* 91:2260 (1994)], and PER is observed in nuclei at night but not late in the day [Siwicki et al *Neuron* 1:141 (1988); Saez and Young *Mol. Cell. Biol.* 8:5378 (1988); Zerr et al *J. Neuronsci* 10:2749 (1990)]. The expression of per RNA is also cyclic.

However, peak mRNA amounts are present late in the day, and the smallest amounts are present late at night [Konopka and Benzer *Proc. Natl. Acad. Sci. U.S.A.* 68:2112 (1971)]. Three mutant alleles—per$^o$, per$^S$, and per$^L$, —cause arrhythmic behavior or shorten or lengthen periods, respectively [Konopka and Benzer *Proc. Natl. Acad. Sci. U.S.A.* 68:2112 (1971)]. These mutations also produce corresponding changes in the rhythms of per RNA and protein amounts [Edery et al *Proc. Natl. Acad. Sci. U.S.A* 91:2260 (1994); Hardin et al *Nature* 343:536 (1990); *Proc. Natl. Acad. Sci. U.S.A.* 89:11711 (1992); Sehgal et al *Science* 263:1603 (1994)] and PER immunoreactivity in nuclei [Sewicki et al *Neuron* 1:141 (1988); Saez and Young *Mol. Cell. Biol.* 8:5378 (1988); Zerr et al *J. Neuronsci.* 10:2749 (1990)]. This suggests a possible role for molecular oscillations of per in the establishment of behavioral rhythms [Hardin et al, *Proc. Natl. Acad. Sci. U.S.A.* 89:11711 (1992)].

Several mutations that affect eclosion and locomotor activity have been isolated in behavioral screens [Jackson, in *Molecular Genetics of Biological Rhythms*, pp. 91–121, M. W. Young, Ed. (Dekker, N.Y., 1993); Konopka and Benzer *Proc. Natl. Acad. Sci. U.S.A.* 68:2112 (1971); Rosbash and Hall *Neuron* 3:387 (1989); Baylies et al in *Molecular Genetics of Biological Rhythms*, pp. 123–153, M. W. Young, Ed. (Dekker, N.Y., 1993); Jackson, *J. Neurogenet* 1:3 (1983); Dushay et al *J. Biol. Rhythms* 4:1 (1989); Dushay et al *Genetics* 125:557 (1990); Konopka et al., *Proc. Natl. Acad. Sci. U.S.A.* 68:2112 (1991)]. The best characterized, and those with the strongest phenotypes, are mutations at the X chromosome-linked period (per) locus [Konopka and Benzer *Proc. Natl. Acad. Sci. U.S.A.* 68:2112 (1971); Rosbash and Hall *Neuron* 3:387 (1989); Baylies et al in *Molecular Genetics of Biological Rhythms*, pp. 123–153, M. W. Young, Ed. (Dekker, N.Y., 1993); Jackson, *J. Neurogenet* 1:3 (1983); Dushay et al *J. Biol. Rhythms* 4:1 (1989); Dushay et al *Genetics* 125:557 (1990)]. Missense mutations at per can lengthen or shorten the period of circadian rhythms, whereas null mutations abolish circadian rhythms altogether. The per gene is expressed in many cell types at various stages of development. In most cell types, the period protein (PER) is found in nuclei [James et al *EMBO J.* 5:2313 (1986); Liu et al *Genes Dev.* 2:228 (1988); Saez and Young *Mol. Cell. Biol.* 8, 5378 (1988); Liu et al *J. Neurosci.* 12:2735 (1992) Siwicki et al *Neuron* 1:141 (1988); Zerr et al *J. Neurosci.* 10:2749 (1990); Edery et al *Proc. Natl. Acad. Sci. U.S.A.* 91:2260 (1994)]. A domain within PER is also found in the Drosophila single-minded protein (SIM) and in subunits of the mammalian aryl hydrocarbon receptor [Crews et al *Cell* 52:143 (1988); Hoffman et al *Science* 252:954 (1991); Burbach et al *Proc. Natl. Acad. Sci. U.S.A.* 89:8185 (1992); Reyes et al *Science* 256:1193 (1992)], and this domain (PAS, for PER, ARNT, and SIM) mediates dimerization of PER [Huang et al *Nature* 364:259 (1993)]. The amounts of both PER protein and RNA oscillate with a circadian period, which is affected by the per mutations in the same manner as behavioral rhythms are affected [Siwicki et al *Neuron* 1:141 (1988); Zerr et al *J. Neuronsci* 10:2749 (1990) Edery et al *Proc. Natl. Acad. Sci. U.S.A* 91:2260 (1994); Hardin et al *Nature* 343:536 (1990); *Proc. Natl. Acad. Sci. U.S.A.* 89:11711 (1992)]. Given the homologies to sim and the aryl hydrocarbon receptor (which are thought to regulate transcription), the effects of per on behavioral rhythms have been postulated to depend on circadian regulation of gene expression, including that of per itself [Hardin et al, *Nature* 343:536 (1990); Hardin et al, *Proc. Natl. Acad. Sci. U.S.A.* 89:11711 (1992)].

Timeless is a second gene which has been associated with circadian rhythms in Drosophila [U.S. patent application Ser. No. 08/619,198 filed Mar. 21, 1996, hereby incorporated by reference in its entirety]. In the absence of the Timeless protein, TIM, gene products, such as the Period protein, PER, are not stable in the cytoplasm. Upon binding to the Timeless protein, proteins such as PER are stabilized and translocated into the nucleus. Once in the nucleus, the proteins act to inhibit the production of their own RNA. Both the tim and per genes are transcribed cyclically, and this transcription drives behavior. In particular, the gene products are present in the cytoplasm late in the day when a sleeping cycle is induced, while when the gene products are in the nucleus late at night, and a waking cycle follows.

The TIM protein not only acts as a nuclear translocation factor for the PER protein, but the PER protein also serves as a nuclear translocation factor for the TIM protein, thus indicating that PER and TIM act as mutual and reciprocal nuclear translocation factors. The nuclear translocation of the PER-TIM heterodimer is a crucial step in the regulation of both tim DNA and per DNA transcription.

The TIM protein also plays an important role in entraining the circadian rhythm of Drosophila, and by analogy other animals, to environmental cycles of light. This property of the TIM protein is due to its requirement for stabilizing the PER protein; its role in regulating per DNA transcription; and the TIM protein's extreme sensitivity to light. Unlike the PER protein which requires the TIM protein for stability, the stability of the TIM protein is independent of the PER protein.

Our current understanding of the molecular regulation of circadian rhythmicity in Drosophila comes from integrating genetics and molecular biology. Null mutations in either of two genes, period (per) and timeless (tim), abolish behavioral rhythmicity, while alleles encoding proteins with missense mutations have been recovered at both loci and show either short- or long-period behavioral rhythms [Konopka and Benzer, *Proc. Natl. Acad. Sci USA*, 68:2112–2116 (1971); Sehgal et al., *Science*, 263:1603–1606 (1994); Rutila et al., *Neuron*, 17:921–929 (1996)]. The RNA and protein products of the genes oscillate with a circadian rhythm in wild-type flies. These molecular rhythms are abolished by null mutations of either gene, and the periods of all molecular rhythms are correspondingly altered in each long- and short-period mutant indicating a regulatory interaction between these genes (Hardin et al., *Nature*, 343:536–540 (1990); Edery et al., *Proc. Natl. Acad. Sci USA*, 91:2260–2264 (1994); Sehgal et al., *Science*, 263:1603–1606 (1994); Vosshall et al., *Science*, 263:1606–1609 (1994); Seghal et al., *Science*, 270:808–810 (1995); Price et al., *EMBO J.*, 14:4044–4049 (1995); Hunter-Ensor et al., *Cell*, 84:677–685 (1996); Myers et al., *Science*, 271:1736–1740 (1996); Zeng et al., *Nature*, 380:129–135 (1996)].

Production of these molecular cycles appears to depend on the rhythmic formation and nuclear localization of a complex containing the PER and TIM proteins [Seghal et al., *Science*, 270:808–810 (1995); Gekakis et al., *Science*, 270:811–815 (1995); Lee et al., *Science*, 271:1740–1744 (1996); Saez and Young, *Neuron*, 17:911–920 (1996); Saez and Young, *Neuron*, 17:911–920 (1996)]. A physical interaction of PER and TIM is required for nuclear localization of either protein, and nuclear activity of these proteins coordinately regulates per and tim transcription through a negative feedback loop [Sehgal et al., *Science*, 263:1603–1606 (1994); Vosshall et al., *Science*, 263:1606–1609 (1994); Seghal et al., *Science*, 270:808–810 (1995); Gekakis et al., *Science*, 270:811–815 (1995); Hunter-Ensor et al., *Cell*, 84:677–685 (1996); Lee et al.,

*Science*, 271:1740–1744 (1996); Myers et al., *Science*, 271:1736–1740 (1996); Saez and Young, *Neuron*, 17:911–920 (1996);. Zheng et al., *Nature*, 380:129–135 (1996)]. Studies of per$^L$, a mutation that lengthens the period of behavioral rhythms [Konopka and Benzer, *Proc. Natl. Acad. Sci. USA*, 68:2112–2116 (1971)] and delays nuclear localization of PER protein [Curtin et al., *Neuron*, 14:365–372 (1995)], have shown that the PER$^L$ protein has reduced affinity for TIM [Gekakis et al., *Science*, 270:811–815 (1995). This suggests that rates of PER/TIM association influence the period of the molecular cycle in mutant and wild type flies.

Seghal et al., [*Science*, 270:808–810 (1995)] proposed a model for the Drosophila clock in which delayed formation of PER/TIM complexes ensures separate phases of per/tim transcription and nuclear function of the encoded proteins. Recent mathematical treatments of the Drosophila data are consistent with this model [Leloup and Goldbeter, *J. Biol. Rhythms*, 13:70–87 (1998)]. Entrainment of this oscillator is regulated through the TIM protein, which is rapidly eliminated from the nucleus and cytoplasm of pacemaker cells when Drosophila are exposed to daylight [Hunter-Ensor et al., *Cell.*, 84:677–685 (1996); Lee et al., *Science*, 271:1740–1744 (1996); Myers et al., *Science*, 271:1736–1740 (1996); Zheng et al., *Nature*, 380:129–135 (1996)]. Studies of transgenic Drosophila have shown that adult behavioral rhythms can be linked to per and tim expression in a small group of central brain cells, the lateral neurons [Ewer et al., (1992); Frisch et al., *Neuron*, 12:555–570 (1994); Vosshall and Young, *Neuron*, 15:345–360 (1995)]. per and tim are also expressed inlarval brain cells that are most likely the larval LNs [Kaneko et al., *Neurosci.*, 17:6745–6760 (1997)], suggesting a basis for larval entrainment to light/dark cycles [Sehgal et al., *Proc. Natl. Acad. Sci. USA*, 89:1423–1427 (1992)]. Oscillations of per and tim RNA, and PER and TIM proteins have been found outside of the head in a variety of tissues [Giebultowicz and Hege, *Nature*, 386:664 (1997); Emery et al., *Proc. Natl. Acad. Sci. USA*, 94:4092–4096 (1997); Plautz et al., *Science*, 278:1632–1635 (1997)]. Some of the latter oscillations were observed in vitro with isolated tissues, further indicating a cell autonomous mechanism [Giebultowicz and Hege, *Nature*, 386:664 (1997); Emery et al., *Proc. Natl. Acad. Sci. USA*, 94:4092–4096 (1997); Plautz et al., *Science*, 278:1632–1635 (1997)]. Mammalian homologues of per have recently been identified [Tei et al., *Nature*, 389 (1997); Sun et al., *Cell*, 90:1003–1011 (1997); Shigeyoshi et al., *Cell*, 91:1043–1053 (1997); Albrecht et al., *Cell*, 91:1055–1064 (1997); Shearman et al., *Neuron*, 19:1261–1269 (1997)], suggesting that the molecular basis of circadian rhythms may be conserved from flies to mammals. A related circadian oscillator has also been described at the molecular level in Neurospora through the detailed work of Dunlap and colleagues [reviewed by Dunlap et al., *Annu. Rev. Genet.*, 30:579–601 (1996)].

Although key features of the Drosophila clock have been identified, the involvement of additional, essential factors is suspected from prior work. Since neither PER nor TIM has a recognizable DNA-binding motif, an unidentified transcription factor(s) should mediate repression in response to nuclear PER/TIM complexes [(reviewed by Rosbash et al., *Harb. Symp. Quant. Biol.*, 76:265–278 (1996); Young et al., *Harb. Symp. Quant. Biol.*, 61:279–284 (1996)]. PER fails to accumulate in the absence of TIM even in the presence of high per RNA levels [Vosshall et al., *Neuron*, 15:345–360 (1994); Price et al., *EMBO J.*, 14:4044–4049 (1995)], indicating the existence of an activity that de-stabilizes cytoplasmic PER monomers. Both PER and TIM are phosphorylated with a circadian rhythm [Edery et al., *Proc. Natl. Acad Sci. USA*, 94:4092–4096 (1994); Zeng et al., *Nature*, 380:129–135, 1996)] indicating unidentified kinases. PER, in particular, becomes progressively phosphorylated over many hours, and the timing of this is changed in period-altering mutants, leading to the suggestion that defined hyperphosphorylated form(s) of PER might signal PER degradation [Edery et al., *Proc. Natl. Acad. Sci. USA*, 94:4092–4096 (1994)].

In summary, circadian rhythms in Drosophila require periodic interaction of the PERIOD (PER) and TIMELESS (TIM) proteins. Physical associations of PER and TIM allow their nuclear translocation, and autoregulation of per and tim transcription through a negative feedback loop. Because PER/TIM heterodimers are only observed when high levels of per and tim RNA have accumulated, self-sustained oscillations are produced in the feedback loop [Gekakis et al., *Science*, 270:811–815 (1995); Hunter-Ensor et al., *Cell*, 84:677–685 (1996); Myers et al., *Science*, 271:1736–1740 (1996); Saez and Young, *Neuron*, 17:911–920 (1996); Sehgal et al., *Science*, 270:808–810 (1995) and Zeng et al., *Nature*, 380:129–135 (1996)]. Although molecular oscillations are maintained in constant darkness for per and tim RNA and for PER and TIM proteins, light can entrain the phases of these rhythms through rapid degradation of the light-sensitive TIM protein [Hunter-Ensor et al., *Cell*, 84:677–685 (1996); Myers et al., *Science*, 271:1736–1740 (1996) and Zeng et al., *Nature*, 380:129–135 (1996)]. Circadian oscillations of PER and TIM phosphorylation have also been described [Edery et al., *PNAS, USA*, 91:2260–2264 (1994) and Zeng et al., *Nature*, 380:129–135 (1996)]. However, prior studies have not demonstrated a function for these modifications. The recent identification of several PER homologues from mammals [Albrecht et al. *Cell*, 91:1055–1064 (1997); Shearman et al., *Neuron*, 19:1261–1269 (1997); Shigeyoshi et al., *Cell*, 19:1043–1053 (1997); Sun et al., *Cell*, 90:10031011 (1997) and Tei et al., *Nature*, 389:512–516 (1997)] suggests that, like many other biological processes, key molecules and mechanisms involved in circadian rhythms may be evolutionarily conserved between flies and mammals. A related mechanism has also been well defined in Neurospora [cf. Crosthwaite et al., *Science*, 276:763–769 (1997); Dunlap, *Ann. Rev. of Gen*, 30:579–601 (1996) and Garceau et al., *Cell*, 89:469–476 (1997)] and additional genes and proteins are known to play roles in the mouse [Antoch et al., (1997); King et al., *Cell*, 89:641–653 (1997) and Vitaterna et al., *Science*, 264:719–725 (1994)] the hamster [Ralph and Menaker, *Science*, 241:1225–1227 (1988)] and Arabidopsis [Millar et al., *Science*, 267:1161–1163 (1995)].

Therefore there is a need to identify other factors involved in circadium rythms. Furthermore, there is a need to use such factors to identify agents that can aid in the regulation of biological clocks, including as an aid in overcoming such maladies as jet lag. The citation of any reference herein should not be construed as an admission that such reference is available as "Prior Art" to the instant application.

SUMMARY OF THE INVENTION

The present invention discloses a protein DOUBLETIME (DBT), which is involved in circadium rhythms. More particularly, DBT plays a role in the regulation of the concentration of the important clock gene, Period (PER). Therefore the present invention provides isolated nucleic acids and/or recombinant DNA molecules that encode DOUBLETIME (DBT) proteins and the fragments thereof including DBT chimeric peptides and proteins of present invention. The present invention further provides the isolated and/or recombinant DBT proteins and fragments thereof including DBT chimeric peptides and proteins. In addition, the present invention provides antibodies to DBT. Methods of using these nucleic acids, proteins, and antibodies (including the human homologue [Fish et al., Journ.BiolChem, 270:14875–14883 (1995)] having the nucleic acid sequence of SEQ ID NO:14, the amino acid sequence of SEQ ID NO:9, and antibodies thereto)as reagents for drug screening and therapeutics are also provided.

One aspect of the present invention includes a nucleic acid that comprises a nucleotide sequence that encodes DBT. In one such embodiment the nucleic acid comprises a nucleotide sequence that encodes a Drosophila DBT. In another embodiment, the nucleic acid comprises a nucleotide sequence that encodes a mammalian DBT. In a preferred embodiment of this type the mammalian DBT is a human DBT that is not the human casein kinase Iε having the amino acid sequence of SEQ ID NO:9.

In a particular embodiment the nucleic acid comprises a nucleotide sequence that encodes a DBT having an amino acid sequence of SEQ ID NO:2. In a preferred embodiment of this type, the nucleic acid comprises the coding sequence of SEQ ID NO:1. In another embodiment the nucleic acid comprises a nucleotide sequence which encodes a DBT and hybridizes to the complementary strand of a nucleotide sequence that encodes a DBT having an amino acid sequence of SEQ ID NO:2. In a related embodiment the nucleic acid comprises a nucleotide sequence that encodes a DBT having an amino acid sequence of SEQ ID NO:2 comprising a conservative substitution. In another embodiment the nucleic acid comprises a nucleotide sequence which encodes a DBT and hybridizes to the complementary strand of a nucleotide sequence that encodes a DBT having an amino acid sequence of SEQ ID NO:2 comprising a conservative substitution.

In an alternative embodiment the nucleic acid comprises a nucleotide sequence that encodes a modified DBT having an amino acid sequence of SEQ ID NO:3. In another such embodiment the nucleic acid comprises a nucleotide sequence that encodes a modified DBT having an amino acid sequence of SEQ ID NO:3 comprising a conservative substitution. In still another embodiment the nucleic acid comprises a nucleotide sequence that encodes a modified DBT having an amino acid sequence of SEQ ID NO:4. In yet another embodiment the nucleic acid comprises a nucleotide sequence that encodes a modified DBT having an amino acid sequence of SEQ ID NO:4 comprising a conservative substitution.

In a related embodiment the present invention provides a nucleic acid that encodes an ATP-binding site of a DBT having an amino acid sequence of SEQ ID NO:6. In a preferred embodiment of this type, the nucleic acid comprises the coding sequence of SEQ ID NO:5. In another embodiment the nucleic acid encodes an ATP-binding site of a DBT having an amino acid sequence of SEQ ID NO:6 comprising a conservative substitution.

In another related embodiment the present invention provides a nucleic acid that comprises a nucleotide sequence that encodes a kinase catalytic domain of a DBT having an amino acid sequence of SEQ ID NO:8. In a preferred embodiment of this type, the nucleic acid comprises the coding sequence of SEQ ID NO:7. In another embodiment the nucleic acid comprises a nucleotide sequence that encodes a kinase catalytic domain of a DBT having an amino acid sequence of SEQ ID NO:8 comprising a conservative substitution.

The present invention further provides a nucleic acid consisting of at least 15, preferably at least 24, more preferably at least 36 consecutive nucleotides of a nucleotide sequence that encodes a DOUBLETIME protein having an amino acid sequence of SEQ ID NO:2. Another such embodiment is a nucleic acid consisting of at least 15, preferably at least 24, more preferably at least 36 consecutive nucleotides of a nucleotide sequence that encodes a DOUBLETIME protein having an amino acid sequence of SEQ ID NO:2 comprising a conservative substitution. In addition, the present invention provides nucleotide probes of at least 18 nucleotides for a nucleotide sequence that encodes a DOUBLETIME protein having an amino acid sequence of SEQ ID NO:2.

All of the nucleic acids of the present invention can further comprise a heterologous nucleotide sequence. Furthermore, all of the nucleic acids of the present invention can be constructed into recombinant DNA molecules. Such recombinant DNA molecules can be operatively linked to an expression control sequence. The expression vectors containing the recombinant DNA molecules of the present invention are also provided by the present invention. In addition methods of expressing the recombinant DNA molecules for making the corresponding recombinant proteins and peptides are also provided. Thus, the recombinant proteins and peptides can be expressed in a cell (either a prokaryotic cell or a eukaryotic cell) containing an expression vector of the present invention by culturing the cell in an appropriate cell culture medium under conditions that provide for expression of the protein by the cell. In one such embodiment, a recombinant DOUBLETIME protein is expressed in a cell containing an expression vector of the present invention by culturing the cell in an appropriate cell culture medium under conditions that provide for expression of the DOUBLETIME protein by the cell. In a preferred embodiment of this type, the method further comprises the step of purifying the recombinant DOUBLETIME. The present invention also includes the recombinant DOUBLETIME proteins and peptides made and/or purified by such methods.

Another aspect of the present invention is the protein encoded by a DOUBLETIME gene. In one embodiment the protein is a Drosophila DBT. In another embodiment, the protein is a mammalian DBT. In a preferred embodiment of this type the mamnalian DBT is a human DBT.

In a particular embodiment the DBT has an amino acid sequence of SEQ ID NO:2. In another embodiment the DBT has an amino acid sequence of SEQ ID NO:2 comprising a conservative substitution. In a related embodiment the DBT is a modified DBT that has an amino acid sequence of SEQ ID NO:3. In another embodiment the DBT is a modified DBT that has an amino acid sequence of SEQ ID NO:3 comprising a conservative substitution. In still another embodiment the modified DBT has an amino acid sequence of SEQ ID NO:4. In yet another embodiment the modified DBT has an amino acid sequence of SEQ ID NO:4 comprising a conservative substitution.

In a related embodiment the present invention provides a protein or peptide comprising an ATP-binding site of a DBT that has an amino acid sequence of SEQ ID NO:6. In another embodiment the protein or peptide comprises an ATP-binding site of a DBT having an amino acid sequence of SEQ ID NO:6 comprising a conservative substitution. In another related embodiment the present invention provides a protein or peptide comprising a kinase catalytic domain of a DBT having an amino acid sequence of SEQ ID NO:8. In another embodiment the protein or peptide comprises a kinase catalytic domain of a DBT that has an amino acid sequence of SEQ ID NO:8 comprising a conservative substitution.

The present invention further provides fragments of the proteins and peptides of the present invention, including proteolytic fragments. In one embodiment the proteolytic fragment comprises at least six amino acids. In a preferred embodiment the proteolytic fragment comprises at least nine amino acids. In a more preferred embodiment the proteolytic fragment comprises at least fifteen amino acids. In one particular embodiment the fragment binds to the period (PER) protein. In another particular embodiment the fragment has protein kinase activity.

The present invention further provides fusion proteins comprising the proteins, peptides and fragments thereof of the present invention. Thus all of the DBTs and fragments thereof of the present invention can be modified, placed in a fusion of chimeric peptide or protein, or labeled e.g., to have an N-terminal FLAG-tag. In a particular embodiment a DBT can be modified to contain a marker protein such as green fluorescent protein as described in U.S. Pat. No. 5,625,048 filed Apr. 29, 1997 and WO 97/26333, published Jul. 24, 1997 the disclosures of which each are hereby incorporated by reference herein in their entireties. Still another aspect of the present invention provides an antibody to a DBT or fragment thereof, of the present invention. In one such embodiment the antibody of is a polyclonal antibody. In another embodiment the antibody is a monoclonal antibody. In a particular embodiment of this type the monoclonal antibody is a chimeric antibody. The present invention further provides immortal cell lines that produce the monoclonal antibodies of the present invention.

Another aspect of the present invention provides methods for detecting the presence or activity of the DBTs of the present invention. One such embodiment comprises contacting a biological sample from an organism in which the presence or activity of the DBT is suspected with a binding partner for the DBT under conditions that allow binding of the DBT to the binding partner to occur, and then detecting whether the binding has occurred between the DBT and the binding partner in the sample. Detection of such binding indicates that the DBT is present in the sample.

Still another aspect of the present invention includes methods of identifying an agent that modulates the interaction between a PER protein and a DBT protein. One such method comprises contacting the PER protein with the DBT protein in the presence of the agent under conditions in which the DBT protein binds the PER protein in the absence of the agent. The binding of the PER protein and the DBT protein is then measured. An agent that modulates the interaction between the PER protein and the DBT protein is identified when the binding of the PER protein with the DBT protein is different in the presence of the agent than in its absence. An agent that modulates the PER protein—DBT protein interaction by enhancing the binding is identified as an agonist. On the other hand, an agent that modulates the PER protein—DBT protein interaction by diminishing the binding is identified as an antagonist. In a preferred embodiment the DBT protein is human casein kinase Iϵ.

In a particular embodiment, the step of determining the binding of the PER protein and the DBT protein includes determining the dissociation constant between the PER protein and the DBT protein. In another embodiment, an active fragment of the PER protein is used in place of the PER protein. In this case the active fragment of the PER protein minimally retains its DBT protein binding capacity. In a related embodiment, an active fragment of the DBT protein is used in place of the DBT protein. In this case the active fragment of the DBT protein minimally retains its PER protein binding capacity. In still another embodiment, an active fragment of the PER protein is used in place of the PER protein and an active fragment of the DBT protein is used in place of the DBT protein. Again, the active fragment of the PER protein minimally retains its DBT protein binding capacity, whereas the active fragment of the DBT protein minimally retains its PER protein binding capacity.

A related aspect of the present invention includes a method of identifying an agent that modulates the phosphorylation of a PER protein by a DBT. One such embodiment comprises contacting the PER protein with the DBT protein in the presence of the agent under conditions in which the DBT protein phosphorylates the PER protein in the absence of the agent. The phosphorylation of the PER protein is then measured (either directly or indirectly). An agent that modulates the phosphorylation of the the PER protein by the DBT protein is identified when the phosphorylation of the PER protein is different in the presence of the agent than in its absence. An agent that modulates the DBT-dependent phosphorylation of the PER protein by enhancing the phosphorylation is identified as an agonist. On the other hand, an agent that modulates the DBT-dependent phosphorylation of the PER protein by diminishing the phosphorylation is identified as an antagonist. In a preferred embodiment the DBT protein is human casein kinase Iϵ.

In a particular embodiment, an active fragment of the PER protein is used in place of the PER protein. In this case the active fragment of the PER protein minimally retains its phosphorylation site, but preferably also retains its DBT protein binding capacity. In a related embodiment, an active fragment of the DBT protein is used in place of the DBT protein. In this case the active fragment of the DBT protein minimally retains its kinase activity but preferably also retains its PER protein binding capacity. In still another embodiment, an active fragment of the PER protein is used in place of the PER protein and an active fragment of the DBT protein is used in place of the DBT protein. Again, the active fragment of the PER protein minimally retains its phosphorylation site, but preferably also retains its DBT protein binding capacity, whereas the active fragment of the DBT protein minimally retains its kinase activity but preferably also retains its PER protein binding capacity.

Such assays can be performed in vitro or in situ (for example in cells as in the cis-trans assays as described below). In one such in situ assay, the proteins or active fragments thereof are contacted in the cell by expressing the corresponding nucleic acids that encode the two proteins in the cell.

Yet another aspect of the present invention comprises methods of identifying the nucleotide and amino acid sequences of homologues to the Drosophila doubletime gene. Once the coding region of the nucleotide sequence is identified, the corresponding amino acid sequence can be readily determined using the genetic code, preferably with the aid of a computer. Preferably the full-length nucleotide sequence of the coding region of a homologue to the Drosophila doubletime gene is identified. It is also preferable that the non-Drosophila gene is a mammalian gene, more preferably a human gene, i.e., the homologue to the Drosophila doubletime gene is identified as a human doubletime gene, which is not the human casein kinase Iε having the amino acid sequence of SEQ ID NO:9. Recombinant DNA molecules and the recombinant DBT proteins obtained by these methods are also part of the present invention.

One method of identifying a nucleotide sequence of the coding region of a homologue to the Drosophila doubletime gene comprises comparing SEQ ID NO:2 with the amino acid sequences encoded by nucleic acids that are obtained from a library of nucleic acids containing partial nucleotide sequences of the coding regions from non-Drosophila genes. Preferably this determination is aided by computer analysis. A nucleic acid containing a partial nucleotide sequence of a coding region from a non-Drosophila gene that is highly homologous to SEQ ID NO:2 can then be selected. Methods of ascertaining which nucleic acid and amino acid sequences are highly homologous are described below.

The full-length sequence of the coding region of the non-Drosophila gene is preferably determined. The sequence is identified as being that of the homologue to the Drosophila doubletime gene when it is highly homologous to SEQ ID NO:2 as discussed below. In a preferred embodiment this method further comprises determining whether the nucleotide sequence that contains a coding region for an amino acid sequence that is highly homologous to SEQ ID NO:2 is also expressed in the corresponding suprachiasmatic nucleus (SCN), i.e., if the putative homologue is a mouse homologue, the SCN of a mouse is tested [Sun et al., Cell 90:1003–1011 (1997)]. When the nucleotide sequence is expressed in the SCN, it is identified as the nucleotide sequence of the coding region of the homologue to the Drosophila doubletime gene. One means of determining whether the nucleotide sequence is expressed in the SCN is through the use of a labeled nucleotide probe for the nucleotide sequence that contains the coding region for an amino acid sequence that is highly homologous to SEQ ID NO:2. The labeled nucleotide probe can then be hybridized with a sample containing nucleic acids that are expressed in the SCN under stringent conditions. If hybridization is detected, the sequence is identified as being that of the homologue to the Drosophila doubletime gene. Similarly, a PCR primer can be used to aid in the confirmation of the identification of a nucleotide sequence of the coding region of the homologue to the Drosophila doubletime gene In a particular embodiment of the method, determining the full-length sequence of the coding region is performed by sequencing the insert of a plasmid which contains a nucleic acid encoding an amino acid sequence that is highly homologous with SEQ ID NO:2. In this case, the insert comprises the nucleic acid. In another embodiment, the full-length sequence is determined by PCR.

A related embodiment includes a method of identifying the full-length nucleotide sequence of the coding region of a homologue to the Drosophila doubletime gene that comprises determining the percent homology of SEQ ID NO:2 to amino acid sequences encoded by nucleotide sequences from a library of nucleotide sequences for non-Drosophila genes and then selecting a nucleotide sequence that contains a coding region for an amino acid sequence that is highly homologous to SEQ ID NO:2. The full-length nucleotide sequence of the coding region for the amino acid sequence is determined and the full-length nucleotide sequence of the coding region of the homologue to the Drosophila doubletime gene is identified. This method can also comprise determining whether the nucleotide sequence is expressed in the suprachiasmatic nucleus (SCN). When the nucleotide sequence is expressed in the SCN, it is identified as the nucleotide sequence of the coding region of the homologue to the Drosophila doubletime gene.

In another embodiment, the method can further comprise constructing a recombinant DNA that contains the coding region. In one such embodiment a recombinant DBT protein is made by expressing the recombinant DNA. In a preferred embodiment of this type an activity of the recombinant Drosophila DBT is assayed. In one such embodiment, the activity assayed is the ability of the recombinant protein to bind to PER. In another such embodiment the activity assayed is the ability of the recombinant protein to act as a protein kinase. In yet another such embodiment the activity assayed is the ability of the recombinant protein to phosphorylate PER. The sequence is identified as being that of the homologue to the Drosophila doubletime gene when the recombinant protein has the activity of the Drosophila DBT.

In addition the present invention provides test kits for demonstrating the presence or absence of a DBT in a cellular sample. One such kit comprises a predetermined amount of a detectably labeled binding partner of the protein. A preferred kit further comprises a predetermined amount of the DBT to be used as a standard. A kit of the present invention can also provide a protocol for using the kit.

The present invention also provides methods of preventing and/or treating disorders of a circadian rhythm which include depression, narcolepsy and jet lag. Such methods rely on temporary antagonisms to transiently inhibit the natural clock, and then supplying agonists to subsequently reset it e.g., for the treatment of jet lag. One such embodiment comprises administering to an animal a therapeutically effective amount of a DBT. Another such embodiment comprises administering to an animal a therapeutically effective amount of an agent capable of promoting the production and/or activity of a DBT. Yet another such embodiment comprises a mixtures of such agents. Still another embodiment comprises administering to an animal a therapeutically effective amount of an agent capable of inhibiting the activity of the DBT.

Accordingly, it is a principal object of the present invention to provide DBTs in purified form that exhibit activities associated with circadium rhythms.

It is a further object of the present invention to provide antibodies to the DBTs, and methods for their preparation, including by recombinant means.

It is a still further object of the present invention to provide nucleic acids encoding DBTs.

It is a further object of the present invention to provide a method for detecting the presence of the DBT in mammals.

It is a further object of the present invention to provide a method and associated assay system for screening substances such as drugs, agents and the like, that are potentially effective in either mimicking the activity or combating the adverse effects of the DBTs in mammals.

It is a still further object of the present invention to provide a method for the treatment of mammals to control depression, jet lag and/or narcolepsy.

It is a still further object of the present invention to provide pharmaceutical compositions for use in therapeutic methods which comprise or are based upon DBT or upon agents or drugs that control the production, or that mimic or antagonize the activities of the DBT.

It is a still further object of the present invention to provide a method of obtaining a human homologue to the Drosophila DBT.

It is a still further object of the present invention to provide Drosophila expressing mutant forms of DBT.

It is a still further object of the present invention to provide transgenic animals that express mutant forms DBT.

These and other aspects of the present invention will be better appreciated by reference to the following drawings and Detailed Description.

BRIEF DESCRIPTION OF THE DRAWINGS

FIG. 3C shows the side by side analysis of PER proteins at ZT22, ZT0 and CT2 from $dbt^S$, wild type and $dbt^L$ and demonstrates that, relative to wild type, PER phosphorylation is advanced in dbts and delayed in $dbt^L$. Note that three times as much total protein was used in the $dbt^S$ lanes in this panel.

FIG. 4C shows the high magnification of 1vLNs which shows TIM protein in wild type (left), per° (center), and per°; $dbt^P$ (right) strains at ZT22. TIM is nuclear in wild type, but forms cytoplasmic rings in per°, and per°; $dbt^P$.

In FIG. 5A larvae were entrained as in FIG. 4, and PER protein detected as described in Experimental Procedures, Example 1, below. Arrowheads indicate 1vLNs. PER protein oscillates in wild type (WT) 1vLNs, with staining only at ZT1 and CT1. PER is detectable in $dbt^P$ 1vLNs at all 4 time points shown, as well as strongly in other cell clusters. Western blot of extracts from 10 larval brains for per°, wild type, and $dbt^P$ larvae at ZT12 and ZT24 (ZT24 coincides with peak PER accumulation in wild type), run alongside 2 mg protein from wild-type adult heads from either ZT14 or ZT2 (FIG. 5B). The asterisk marks a cross-reacting band that serves as a loading control, confirming that PER accumulates to higher levels in $dbt^P$ than in wild-type or per°. PER is difficult to detect in wild type brain extracts, but a clear PER signal distinguishes wild type from the per° control. FIG. 5C shows RNase protection of per, tim and rp49 RNA from 10 mg wild-type (left) or $dbt^P$ (right) larval brain RNA at ZT14–16 (predicted peak for per RNA expression in wild type). Relative to rp49, per and tim levels are similar in wild type and $dbt^P$. (D) Whole brains of wild-type (left) and $dbt^P$ larvae (center) at ZT1 stained with anti-PER, and SG3 (right) stained with anti-β-gal antibodies (FIG. 5D). The PER-SG3 pattern is very similar to PER in $dbt^P$, indicating that the pattern of PER protein seen in $dbt^P$ larval brains reflects the normal activity of the per promoter. Brain hemispheres from wild type (left) or $dbt^P$ larvae (right) raised in constant light from embryogenesis onwards and stained for PER show that PER accumulates to high levels in 1vLNs and many additional cells of $dbt^P$, but is not detected in wild type (FIG. 5E).

FIGS. 6A–6B show a model depicting influence of dbt on circadian rhythms through altered stability of PER. FIG. 6A shows that in $dbt^P$ mutants, loss of DBT activity results in increased stability of monomeric PER proteins. In constant darkness, high titers of stable PER promote constitutive nuclear translocation of PER/TIM heterodimers. An equilibrium is established in which constitutive production of nuclear PER/TIM dimers is balanced with constitutively low levels of expression of per and tim RNA. High stability of PER in $dbt^P$ leads to a pool of nuclear PER monomers as TIM turns over in nuclei. In wild type Drosophila, DBT activity promotes instability of PER monomers (FIG. 6B). PER proteins are stabilized only when physically associated with TIM. The DBT-conferred instability delays the appearance of PER/TIM complexes, and therefore promotes separate phases of per and tim transcription and PER/TIM complex formation and function.

FIG. 9A shows the total RNA that was isolated from pupae of each of the revertant lines described in Table 4 and dbt mRNA was detected by RNAse protection analysis. Because levels of the dbt transcript do not appear to oscillate (see FIG. 8), pupae from each revertant line were collected without first entraining developing flies to a light:dark cycle. dbt mRNA is weakly detected in homozygous dbt$^P$ pupae and in two incomplete revertants (VIII and IX), high levels of expression are restored in all seven complete phenotypic revertants (see text). Revertant VII was sampled twice. FIG. 9B shows the relative levels of dbt mRNA in (FIG. 9A) which were determined by normalizing to tubulin mRNA levels in each line. The revertant line in which the highest levels of dbt mRNA were detected (line VII) was set to one. Level of dbt mRNA in dbt$^P$ homozygous pupae is ~10% of that detected in line VII. In all of the homozygous viable, behaviorally rhythmic revertant lines, the dbt transcript is detected at 75% or more of the levels detected in revertant line VII.

FIG. 11 shows the dbt gene encodes a casein kinase I family member that is altered in dbt$^S$ and dbt$^L$ mutants. The conceptual translation of the open reading frame of the dbt gene is shown. The predicted protein is 440 amino acids in length with a molecular mass of 48 kDa. PROSITE [Bairoch, *Nucleic Acids Research* 19 *Suppl.*: 2241–2245 (1991)] searches have identified an ATP-binding site between amino acids 15–38 and a Serine/Threonine kinase catalytic domain between amino acids 124–136. Both of these domains are indicated. Sequencing of genomic DNA isolated from the dbt$^S$ and dbt$^L$ lines, as well as the parental line used for EMS mutagenesis identified single nucleotide changes, which result in amino acid changes, in each mutant. The dbt$^S$ mutation changes Proline to Serine at amino acid 47 and the dbt$^L$ mutation changes Methionine to Isoleucine at amino acid 80. An alignment of the kinase domains between DBT (SEQ ID NO:2) and casein kinase I family members from five different species is shown. BLAST [Altschul et al. (1990)] searches reveal that DBT is most closely related to human casein kinase I$\epsilon$, being 86% identical at the amino acid level over the length of the kinase domain. Gaps in sequence are indicated by dashes. Amino acids which are identical to DBT in every species are indicated with a dot. Sequence identity between DBT and other kinases begins with the initiator Methonine and is shaded. Significant homology to other kinases ends with amino acid 292. The names, accession numbers and SEQ ID NOs: of the kinases used for sequence alignment are as follows: H. sapiens (human casein kinase I$\epsilon$, L37043; SEQ ID NOs: 9), A. thaliana (dual specificity kinase, U48779; SEQ ID NO: 10), X. laevis (casein kinase Ia, Y08817, SEQ ID NO: 11), G. gallus (casein kinase Ia S, U80822, SEQ ID NO: 12) and S. pombe (hhpI protein kinase, yeast casein kinaseI homologue, X78871, U10863, SEQ ID NO: 13). [The nucleotide sequence naturally encoding the human homolog of doubletime is SEQ ID NO:14]. The nucleotide and amino acid sequences of the dbt open reading frame have been deposited to GenBank and have been assigned accession number x.

FIG. 12A shows Canton S flies that were entrained to a 12:12 LD cycle and collected at four hour intervals over three days. Heads were separated from bodies of flies collected at each time point and total head RNA was isolated from each sample. per, tim and dbt mRNAs were detected by RNAse protection analysis. FIG. 12B shows per, tim and dbt mRNA levels that were normalized to tubulin mRNA levels at each time point and the relative levels of each transcript plotted against time. The time point with the highest levels of each transcript was set to 100%. While both the per and tim mRNAs display an approximately 10-fold circadian oscillation in their levels, levels of the dbt transcript remain essentially unchanged over three days.

FIG. 13A–13C show DBT and PER physically interact in vitro and in cultured Drosophila cells. FIG. 13A shows (Left) Coomassie-stained, SDS-PAGE of GST and GST-PER fusions proteins after binding of $^{35}$S-labeled DBT proteins. The staining confirms that similar amounts of GST and GST-PER fusion proteins were used in the assay. Arrow indicates BSA present in all the washes. (Right) GST alone and the indicated GST-PER fusions were used to bind in vitro translated, $^{35}$S-labeled DBT protein. Labeled DBT proteins that bound to the indicated GST-PER fusions were visualized by SDS-PAGE and autoradiography. DBT binds to the first 365 aa of PER, but does not bind to aa 530–640 of PER or to GST alone. FIG. 13B shows the co-immunoporecipitation of PER and a GFP-DBT fusion protein in S2 Drosophila cells. FIG. 13C shows proteins from S2 cells, or from S2 cells transfected with hs-per and hs-gfp-dbt, hs-gfp-dbt alone, or hs-per alone were immunoprecipitated with anti-GFP antibodies, separated by SDS-PAGE, transferred to nitrocellulose and co-immunoprecipitated PER was detected by Western analysis. For hs-gfp-dbt, GFP was fused to the amino terminus of DBT.

DETAILED DESCRIPTION OF THE INVENTION

Figure 1A:
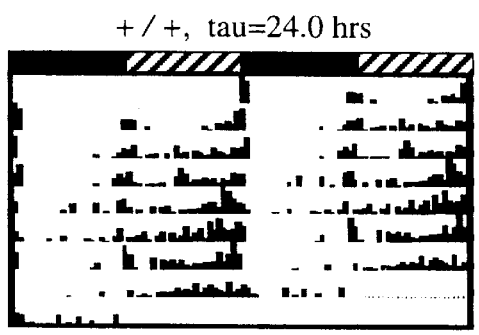
FIGS. 1A–1F show that $dbt^S$ shortens and $dbt^L$ lengthens periods of locomotor activity. Representative locomotor records of single flies of wild type (+/+) in FIG. 1A; $dbt^S$/+ in FIG. 1B; $dbt^S/dbt^S$ in FIG. 1C; wild type in FIG. 1D; $dbt^L$/+ in FIG. 1E; and $dbt^L/dbt^L$ in DD in FIG. 1F. Adult flies were entrained in a 12 hr light: 12 hr dark cycle for more than 3 days, and then locomotor activity was monitored in constant darkness. The phase of the previous light:dark regime is indicated at the top of each record with the hatched boxes indicating the time of the photophase. Horizontal lines are 48 hour intervals and activity is denoted by filled bars, with level of activity indicated by height of each bar. The record for each 24 hour period composing the right half of each line is plotted again on the left half of the line underneath for visual continuity. The period of the rhythm, calculated by chi-square periodogram analysis, and the genotype of each fly are indicated on top of the records. Records in each column are from sibling flies. Activity events occur later on successive days in records with long periods, while they occur earlier on successive days in records with short periods. Note that both $dbt^L$ and $dbt^S$ are semidominant.

The present invention provides the identification and genetic characterization of the clock gene double-time (dbt), a new gene required for circadian rhythms in Drosophila. Isolated alleles that either shorten or lengthen the periods of behavioral and molecular rhythms are also disclosed. A strongly hypomorphic dbt allele that is associated with pupal lethality, and blocks circadian oscillations of per and tim gene products in larvae has been isolated. dbt is therefore shown to be a central clock component alongside per and tim. dbt period-altering alleles alter the kinetics of PER phosphorylation and degradation. The hypomorphic allele produces unusually high levels of PER proteins that are hypophosphorylated. Thus, DBT is involved in the regulation of PER concentration in the cell.

$dbt^S$ and $dbt^L$, mutations which confer short- and long-period mutant phenotypes respectively, are produced by amino acid changes in highly conserved regions of the predicted kinase domain $dbt^P$ mutants, which fail to show circadian rhythms of per and tim expression and produce unusually high levels of hypo-phosphorylated PER protein, produce very low levels of dbt mRNA. In wild type adult fly heads, dbt mRNA appears to be expressed in the same cell types as are per and tim. Furthermore, the present invention shows that DBT is capable of binding to PER in vitro and in cultured Drosophila cells, indicating that a physical association of PER and DBT regulates PER phosphorylation and accumulation in vivo. Two features of dbt distinguish it from other genes involved in circadian rhythms of Drosophila: First, levels of its transcript show no evident oscillation. Second, hypomorphic mutations of dbt are lethal during pupal development, suggesting that DBT may have other important roles beyond that in circadian rhythms.

In addition, the present invention shows that DBT is most closely related to human casein kinase Iε, thereby providing strong evidence that human casein kinase Iε is a Drosophila DBT homologue. This aspect of the present invention therefore allows the novel use of the human casein kinase Iε for the development of new assays and pharmaceuticals based on its role as a human DOUBLETIME protein. More particularly, such assays can lead to the identification of agents that act as either agonists or antagonists of the DBT-dependent phosphorylation of PER.

Therefore, if appearing herein, the following terms shall have the definitions set out below As used herein "DOUBLETIME" and "DBT" are interchangeable names for a protein that can bind the clock protein PER and possesses protein kinase activity. As disclosed herein, Drosophila DBT has an amino acid sequence of SEQ ID NO:2. The natural nucleic acid sequence encoding Drosophila DBT consists of the coding region of SEQ ID NO:1.

As used herein the term "approximately" is used to signify that a value is within ten percent of the indicated value i.e., a protein containing "approximately" 450 amino acid residues can contain between 405 and 495 amino acid residues.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such as solvent preferences.

A "vector" is a replicon, such as a plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transduced" by exogenous or heterologous DNA when the exogenous or heterologous DNA is introduced by a viral vector.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another embodiment the heterologous nucleotide can function as a means of detecting a nucleotide sequence of the present invention. A heterologous nucleotide sequence can comprise non-coding sequences including restriction sites, regulatory sites, promoters and the like.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the negative gene). Allelic variations or naturally-occurring mutational events do not give rise to a heterologous region of DNA as defined herein.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA—RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasnids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, andno formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably at least about 36 nucleotides.

In a specific embodiment, the term "standard hybridization conditions" refers to a $T_m$ of 55° C., and utilizes conditions as set forth above e.g., 5×SSC. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e. g., mammalian) DNA, and even synthetic DNA sequences. If the coding sequence is intended for expression in a eukaryotic cell, a polyadenylation signal and transcription termination sequence will usually be located 3' to the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfanily) and homologous proteins from different species (e.g., myosin light chain, etc.) (Reeck et al., 1987, Cell 50:667).

As used herein, the term "homologue" refers to the relationship between proteins that have a common evolutionary origin and differ because they originate from different species. For example, Drosophila xanthine dehydrogenase is a homologue of human xanthine dehydrogenase.

The term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not necessarily a common evolutionary origin. In a specific embodiment, two highly homologous DNA sequences can be identified by the homology of the amino acids they encode. Such comparison of the sequences can be performed using standard software available in sequence data banks. Alternatively, two highly homologous DNA sequences can be identified by Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

As used herein a nucleic acid sequence is 100% "homologous" to a second nucleic acid sequence if the two nucleic acid sequences are identical. Accordingly, a nucleic acid sequence is 50% "homologous" to a second nucleic acid sequence if 50% of the two nucleic acid sequences are identical.

As used herein an amino acid sequence is 100% "homologous" to a second amino acid sequence if the two amino acid sequences differ only by neutral or conservative substitutions as defined below, or preferably if the two amino acid sequences are identical. Accordingly, an amino acid sequence is 50% "homologous" to a second amino acid sequence if 50% of the two amino acid sequences differ by only neutral or conservative amino acid substitutions, or preferably 50% of the two amino acid sequences are identical.

Since amino acids 1–292 of SEQ ID NO:2 contain a relatively conserved putative protein kinase domain, a "highly homologous" sequence as used herein which corresponds to amino acids 1–292 of SEQ ID NO:2 would be at least about 75%, and preferably at least about 85%, and more preferably at least 90% homologous to amino acids 1–292 of SEQ ID NO:2. For the remainder of the DBT amino acid sequence, i.e., amino acids 293–440 of SEQ ID NO:2, a highly homologous amino acid sequence is at least about 20% homologous with the corresponding portion of SEQ ID NO:2. In a preferred embodiment a highly homologous amino acid sequence is at least about 30% homologous with the corresponding portion of SEQ ID NO:2. In a more preferred embodiment a highly homologous amino acid sequence is at least about 40% homologous with a corresponding portion of SEQ ID NO:2. The amount of homology required for nucleic acids that contain amino acid sequences corresponding to portions of both the kinase and/or non-kinase domains can be determined accordingly. A full-length amino acid sequence that is highly homologous to SEQ ID NO:2 is at least about 55% homologous to SEQ ID NO:2. [In this case 66% of the sequence (contained by amino acids 1–292) is at least 75% homologous, whereas 34% of the sequence (amino acids 293–440) is at least about 20% homologous, or 0.75*0.66+0.34*0.20=~55% homologous.] This calculation is partially based on the finding that the mouse and human PER homologue is about 35% homologous to the Drosophila PER protein [Sun et al., Cell, 90:1003–1011 (1997)]. Such homologous sequences can be identified by alignment using, for example, the GCG (Genetics Computer Group, Program Manual for the GCG Package, Version 7, Madison, Wiss.) pileup program using the default parameters. Alternatively, the commercially available MEGALIGN program within the LASERGENE sequence analysis software package from DNASTAR, Inc, can also be used (see below).

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

DBTs: Proteins and Polypeptides

The present invention provides isolated DBTs and active fragments thereof. DBT is the third Drosophila gene to be isolated that has an essential role in circadian rhythms. DBT has been shown to be capable of binding to PER in vitro and in Drosophila cells. DBT is a kinase that is required for wild type patterns of PER phosphorylation and for adult viability. Sequence analyses indicate that DBT is a structural homologue of human casein kinase I$\epsilon$, with 86% of the amino acids comprising the putative kinase domain of Drosophila DBT being identical to those comprising the kinase domain of human casein kinase I$\epsilon$. PER proteins are hypophosphorylated in $dbt^P$ mutants, and the timing of PER phosphorylation appears to be altered in $dbt^L$ and $dbt^S$ mutants [Example 1, below] indicating that a kinase activity supplied by DBT is required for normal PER phosphorylation in vivo. PER and DBT also physically associate in vitro and in cultured Drosophila cells, and in addition, the formation of a PER/DBT complex leads to DBT-dependent phosphorylation of PER in vitro. DBT is the first Drosophila clock protein to have a structure that indicates a recognizeable biochemical function. Although strong evidence for involvement of protein phosphorylation in circadian rhythmicity has been reported in several organisms DBT is the first specific kinase to be isolated which regulates circadian rhythmicity.

In one embodiment the DBT is a mammalian protein, preferably a human protein. In another embodiment the DBT is a protein encoded by a nucleotide sequence that is hybridizable with the coding sequence of SEQ ID NO:1 under standard, or preferably stringent conditions. In still another embodiment the DBT is encoded by a nucleotide sequence having the coding sequence of SEQ ID NO:1. In yet another embodiment the DBT has an amino acid sequence of SEQ ID NO:2 comprising one or more conservative substitutions. The DBTS of the present invention may be used in assays to identify novel drugs, and the like, and in protein structure and mechanistic studies.

Modified DBTs: The present invention also provides modified DBTs and DBTs that are tagged proteins, labeled proteins, fusion proteins and the like. Such DBTs may be used for example as antigens or for marker purposes. In a particular embodiment of this type, the fusion protein comprises an DBT protein or active fragment thereof having an amino acid sequence of SEQ ID NO:2 or SEQ ID NO:2 comprising a conservative substitution. Such DBTs preferably retain their protein kinase activity and bind PER. One particular use of the DBT fusion proteins of the present invention is for the production of the DBT-antibodies of the present invention.

A DBT fusion protein comprises at least a portion of a non-DBT protein joined via a peptide bond to at least a portion of an DBT polypeptide. In preferred embodiments the portion of the DBT is functional. The non-DBT sequences can be amino- or carboxy-terminal to the DBT sequences. More preferably, for stable expression of a DBT fusion protein, the portion of the non-DBT fusion protein is joined via a peptide bond to the amino terminus of the DBT protein. A recombinant DNA molecule encoding such a fusion protein comprises a sequence encoding at least a portion of a non-DBT protein joined in-frame to the DBT coding sequence, and preferably encodes a cleavage site for a specific protease, e.g., thrombin or Factor Xa, preferably at the DBT-non-DBT juncture. In a specific embodiment, the fusion protein is expressed in *Escherichia coli*. Such a fusion protein can be used to isolate the DBTs of the present invention, through the use of an affinity column which is specific for the protein fused to the DBT. The purified DBT may then be released from the fusion protein through the use of a proteolytic enzyme and the cleavage site such as has been referred to above.

In one such embodiment, a chimeric DBT can be prepared, e.g., a glutathione-S-transferase (GST) fusion protein, a maltose-binding (MBP) protein fusion protein, or a poly-histidine-tagged fusion protein, for expression in a eukaryotic cell. Expression of a DBT as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the DBT and the fusion partner (e.g., GST, MBP, or poly-His) as described above. Alternatively the chimeric DBT protein may contain the green fluorescent protein, and be used to determine the intracellular localization of the DBT in the cell.

Genes Encoding DBTs

The present invention contemplates isolation of a gene encoding a DBT of the present invention, including a full length, or naturally occurring form of DBT, and antigenic fragments thereof from any animal, particularly mammalian, and more particularly human, source. Such nucleic acids may be used for designing primers for RT-PCR, and for making probes that are useful for determining the expression of DBT messenger RNA in tissues and tumors. Similarly such nucleic acids can be used to determine the expression of DBT messenger RNA in normal tissues and tumors by Northern Blot analysis, RNA protection assays and the like. As used herein, the term "gene" refers to an assembly of nucleotides that encode a polypeptide, and includes cDNA and genomic DNA nucleic acids. Therefore, the present invention provides the primary structure of a gene encoding a.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A gene encoding DBT, whether genomic DNA or cDNA, can be isolated from any source, particularly from a human cDNA or genomic library. In view and in conjunction with the present teachings, methods well known in the art, as described above can be used for obtaining DBT genes from any source (see, e.g., Sambrook et al., 1989, supra).

Accordingly, any animal cell or transformed animal cell line potentially can serve as the nucleic acid source for the molecular cloning of a DBT gene. The DNA may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired DBT gene may be accomplished in a number of ways. For example, the generated DNA fragments may be screened by nucleic acid hybridization to a labeled probe of the present invention (Benton and Davis, 1977, Science 196:180; Grunstein and Hogness, 1975, Proc. Natl. Acad. Sci. U.S.A. 72:3961). For example, a set of oligonucleotides corresponding to the sequence information provided by the present invention can be prepared and used as probes for DNA encoding DBT (e.g., in combination with a poly-T primer for RT-PCR). Preferably, a probe is selected that is highly unique to DBT of the invention. Those DNA fragments with substantial homology to the probe will hybridize. As noted above, the greater the degree of homology, the more stringent hybridization conditions can be used.

Further selection can be carried out on the basis of the properties of the gene, e.g., if the gene encodes a protein product having the isoelectric, electrophoretic, amino acid composition, or partial amino acid sequence of the DBT as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for DBT.

A DBT gene of the invention can also be identified by mRNA selection, i. e., by nucleic acid hybridization followed by in vitro translation. In this procedure, nucleotide fragments are used to isolate complementary mRNAs by hybridization. Such DNA fragments may represent available, purified DBT DNA, or may be synthetic oligonucleotides designed from the partial amino acid sequence information. Immunoprecipitation analysis or functional assays (e.g., nucleoside transport activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against DBT.

A radiolabeled DBT cDNA can be synthesized using the selected mRNA (from the adsorbed polysomes) as a template. The radiolabeled mRNA or cDNA may then be used as a probe to identify homologous DBT DNA fragments from among other genomic DNA fragments.

The present invention also relates to cloning vectors containing genes encoding analogs and derivatives of DBT of the invention, that have the same or homologous functional activity as DBT, and in particular homologue thereof from other species. The production and use of derivatives and analogs related to DBT are within the scope of the present invention. In a specific embodiment, the derivative or analog is functionally active, i.e., capable of phosphorylating PER.

DBT derivatives can be made by altering encoding nucleic acid sequences by substitutions, additions or deletions that provide for functionally equivalent molecules. Preferably, derivatives are made that have enhanced or increased functional activity or greater specificity.

Due to the degeneracy of nucleotide coding sequences, other DNA sequences which encode substantially the same amino acid sequence as a DBT gene may be used in the practice of the present invention. These include but are not limited to allelic genes, homologous genes from other species, and nucleotide sequences comprising all or portions of DBT genes which are altered by the substitution of different codons that encode the same amino acid residue within the sequence, thus producing a silent change. Likewise, the DBT derivatives of the invention include, but are not limited to, those containing, as a primary amino acid sequence, all or part of the amino acid sequence of a DBT protein including altered sequences in which functionally equivalent amino acid residues are substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the protein's structure.

The genes encoding DBT derivatives and analogs of the invention can be produced by various methods known in the art. The manipulations which result in their production can occur at the gene or protein level. For example, the cloned DBT gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of DBT, care should be taken to ensure that the modified gene remains within the same translational reading frame as the DBT gene, uninterrupted by translational stop signals, in the gene region where the desired activity is encoded.

Additionally, the DBT-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated DBT gene product. Any technique for mutagenesis known in the art can be used, including but not limited to, in vitro site-directed mutagenesis (Hutclson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transduction, transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharonyces cerevisiae* by linking sequences from an *E. coli* plasmid with sequences from the yeast $2\mu$ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

The nucleotide sequence of the Drosophila doubletime, SEQ ID NO:1 or more preferably the amino acid sequence of SEQ ID NO:2, can also be used to search for highly homologous genes from other species, including humans using computer data bases containing partial nucleic acid sequences. Human ESTs, for example, can be searched. The Drosophila doubletime amino acid sequence, for example, can be compared with computer translated human EST sequences, e.g., in GenBank, using GCG software and the blast search program for example. Matches with highly homologous EST sequences can then be obtained.

The matched EST can then be fully sequenced. One such example is outlined here, though many equivalent systems and variations are known and practiced in the art. DNA sequencing reactions can be assembled on a Beckman Biomek robotic system using standard dye-terminator chemistry, Taq polymerase and thermal cycling conditions described by the vendor (Perking Elmer/Applied Biosystems Division (PE/AB)). Preferably sequencing is performed multiple times to insure accuracy. Reaction products can be resolved on PE/ABD model 373 and 377 automated DNA sequencers. Contig assembly can be performed using any number of programs (e.g., Gap4) and a consensus sequence can be further analyzed using the GCG suite of applications. The resulting sequence can then be used in place of, and/or in conjunction with SEQ ID NO:1 to identify other ESTs which contain coding regions of the human homologue to DBT.

Plasmids containing the matched ESTs can be digested with restriction enzymes in order to release the cDNA inserts. If the plasmid does not contain the full length homologue the digests can be purified, e.g., run on an agarose gel and the bands corresponding to the inserts can be cut from the gel and purified (Quiagen Gel Extraction kit). Such purified inserts are likely to contain overlapping regions which can be combined as templates of a PCR reaction using primers which are preferably located outside of the human DBT open reading frame. The PCR reaction can be performed using ELONGASE (and its standard amplification system) supplied by Gibco-BRL, Gaithersburg, Md., under the following standard conditions:

5 minutes at 94° C.; followed by 25 cycles of: 30 seconds at 94° C., 30 seconds at 50° C., and 3.5 minutes at 72° C.; followed by 10 minutes at 72° C. Amplification should yield the expected product which can be ligated into a vector and used to transform an E coli derivative via TA cloning (Invitrogen) for example. The resulting full-length human DBT can be placed into an expression vector and the expressed recombinant DBT can then be assayed for kinase activity and PER binding activity.

Alternatively, plasmids containing matched EST homologue fragments can be used to transform competent bacteria (e.g, from Gibco BRL, Gaithersburg Md.). Bacteria can be streaked, then grown up overnight. Plasmid preps can be performed (e.g., Quiagen Corp, Santa Clarita Calif.) and the plasmids can be digested by simultaneous restriction digest. Products of the digest can be separated by size on an agarose gel, for example, and purified. The corresponding bands cut from these gels can be ligated to form a fulllength dbt cDNA and used to transform competent bacteria (DHFalpha) and the resulting plasmid can be purified.

Expression of DBTs

The present invention provides for expressing the nucleic acids which encode the DBTs fragments thereof, derivatives or analog thereof, or a functionally active derivative, including a chimeric protein, thereof, that has been inserted into an appropriate expression vector, i.e., a vector which contains the necessary elements for the transcription and translation of the inserted protein-coding sequence. Such elements are termed herein a "promoter." Thus, the nucleic acid encoding a DBT of the invention is operationally associated with a promoter in an expression vector of the invention. Both cDNA and genomic sequences can be cloned and expressed under control of such regulatory sequences. An expression vector also preferably includes a replication origin. One particular use for such expression vectors is to express a DBT in large quantities that can be used for functional and structural studies of the purified protein kinase. The necessary transcriptional and translational signals can be provided on a recombinant expression vector, or they may be supplied by the native gene encoding DBT and/or its flanking regions.

Potential chimeric partners for the DBT of the present invention include green fluorescent protein which may be useful in monitoring the cellular localization of the DBT.

Potential host-vector systems include but are not limited to mammalian cell systems, infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant DBT protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra). The cell containing the recombinant vector comprising the nucleic acid encoding DBT is cultured in an appropriate cell culture medium under conditions that provide for expression of DBT by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of DBT may be controlled by any promoter/enhancer element known in the art, but these regulatory elements must be functional in the host selected for expression. Promoters which may be used to control DBT gene expression include, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thynidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krurlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding a DBT of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding DBT is inserted within the "selection marker" gene sequence of the vector, recombinants containing the DBT insert can be identified by the absence of the DBT gene function. In the fourth approach, recombinant expression vectors can be identified by assaying for the activity, biochemical, or immunological characteristics of the gene product expressed by the recombinant, provided that the expressed protein assumes a functionally active conformation. For example, the protein kinase activity of DBT can be tested.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids coT E1, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker;

Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HinIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the DBT protein. For example, the non-fusion pYES2 vector (XbaI, SphI, ShoI, NotI, GstXI, EcoRI, BstXI, BamHI, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, DBT expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, DBT activity. Furthermore, different vector/host expression systems may affect processing reactions, such as proteolytic cleavages, to a different extent.

Vectors are introduced into the desired host cells by methods known in the art,. e.g., transfection, transduction, electroporation, microinjection, cell fusion, DEAF dextran, calcium phosphate precipitation, lipofection (lysosome fusion), use of a gene gun, or a DNA vector transporter (see, e.g., Wu el al., 1992, J. Biol. Chem. 267:963–967; Wu and Wu, 1988, J. Biol. Chem 263:14621–14624; Hartmut et al., Canadian Patent Application No. 2,012,311, filed Mar. 15, 1990).

The present invention also provides cell lines made from cells transfected or transduced with the DBTs of the present invention. In preferred embodiments of this type the cells are Drosophila cells. In another embodiment the cells are mammalian cells.

General Protein Purification Procedures:

The initial step for purifying the DBTs of the present invention, active fragments thereof, and related tagged or fusion proteins generally consists of lysing the cells containing the DBTs. Cell lysis can be achieved by a number of methods including through the use of a physical means such as a French press, a sonicator, or a blender; or through chemical means including enzymatic extractions (with for example, lysozyme or pancreatin), and/or organic extractions or solubilizations with detergents, such as sodium dodecyl sulfate (SDS), Triton X-100, nonidet P-40 (NP-40), digoxin, sodium deoxycholate, and the like, including mixtures thereof; or through a combination of chemical and physical means. For example, solubilization can be enhanced by sonication of the suspension. Subsequent steps of purification include salting in or salting out, such as in ammonium sulfate fractionations; solvent exclusion fractionations, e.g., an ethanol precipitation; detergent extractions to free the membrane bound DBTs of the present invention using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as PHENYLSEPHAROSE and a high salt buffer; affinity-binding, using, e.g., placing a nucleoside or nucleoside analog on to an activated support; irnmuno-binding, using e.g., an antibody to a DBT of the present invention bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations are used. Low concentration buffers generally infer 5–25 mM concentrations. High concentration buffers generally infer concentrations of the buffering agent of between 0.1–2M concentrations. Typical buffers can be purchased from most biochemical catalogues and include the classical buffers such as Tris, pyrophosphate, monophosphate and diphosphate. The Good buffers [Good, et al., *Biochemistry*, 5:467 (1966); Good et al. *Meth. Enzymol.*, 24: Part B, 53 (1972); and Fergunson, et. al *Anal. Biochem.* 104:300, (1980)] such as Mes, Hepes, Mops, tricine and Ches.

Materials to perform all of these techniques are available from a variety of sources such as Sigma Chemical Company in St. Louis, Mo.

Alignment Programs

DNA and protein sequence alignments can be created using the MEGALIGN program (for ALIGN in older versions) within the LASERGENE sequence analysis software package from DNASTAR, Inc. (See *User's Guide for LASERGENE for the Macintosh*, especially Pages 119–120). The alignments of the DNA sequence for the present invention is performed by the method of Wilbur-Lipman [Wilbur and Lipman, *Proc. Natl. Acad. Sci. USA* 80: 726–730 (1983)] using the default parameters:

(i) K-tuple=3; (ii) Gap Penalty=3; and (iii) Window=20

The alignments of the amino acid sequence for the present invention is performed by the method of Lipman-Pearson [Lipman, and Pearson. *Science* 227:1435–1441 (1985)] using the default parameters:

(i) K-tuple=2; (ii) Gap Penalty=4; and (iii) Gap Length Penalty=12

The LASERGENE manual defines the following terms as:

(1) K-tuple: A K-tuple, or word, is the number of residues compared to each other at a time. A K-tuple of 1 provides a more exhaustive search but takes longer. A higher K-tuple value finds fewer but longer matching regions. A lower K-tuple value finds shorter matching regions.

(2) Gap penalty: For each gap introduced in the alignment, the MEGALIGN deducts a penalty from the score. A higher gap penalty suppresses gapping, a lower value promotes it.

(3) Gap length penalty: MEGALIGN also assesses penalties based on the length of the gap. The more residues the gap spans, the greater the penalty. These penalties are deducted from the overall score of the alignment.

(4) Window: Window determines over how long a range MEGALIGN searches for all possible k-tuples. MAGALIGN first finds a dominant region of similarity. It then uses this region as its starting point and extends diagonally until it reaches the end of the window.

Antibodies to DBTs

According to the invention, a DBT obtained from a natural source or produced recombinantly or by chemical synthesis, and fragments or other derivatives or analogs thereof, including fusion proteins, may be used as an immunogen to generate antibodies that recognize the DBT polypeptide. Such antibodies include but are not limited to polyclonal, monoclonal, chimeric, single chain, Fab fragments, and an Fab expression library. The anti-DBT antibodies of the invention may be cross reactive, e.g., they may recognize a DBT from different species. Polyclonal antibodies have greater likelihood of cross reactivity. Alternatively, an antibody of the invention may be specific for a single form of the DBT, such as Drosophila DBT.

Various procedures known in the art may be used for the production of polyclonal antibodies to a DBT of the present invention or derivative or analog thereof. For the production of antibody, various host animals can be immunized by injection with a DBT or a derivative (e.g., fragment or fusion protein) thereof, including but not limited to rabbits, mice, rats, sheep, goats, etc. In one embodiment, a DBT or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a DBT of the present invention, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. in an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a Drosophila antibody molecule specific for a DBT, for example, together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce DBT-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a DBT or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and imrnunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a DBT, for example the kinase catalytic site, one may assay generated hybridomas for a product which binds to a DBT fragment containing such an epitope. For selection of an antibody specific to a DBT from a particular species of animal, one can select on the basis of positive binding with a DBT expressed by or isolated from cells of that species of animal.

The foregoing antibodies can be used in methods known in the art relating to the localization and activity of the DBT, e.g., for Western blotting, imaging DBT in situ, measuring levels thereof in appropriate physiological samples, etc. using any of the detection techniques mentioned above or known in the art. More particularly, the antibodies of the present invention can be used in flow cytometry studies, in immunohistochemical staining, and in immunoprecipitation which serves to aid the determination of the level of expression of a DBT in a tumor or normal cell or tissue.

In a specific embodiment, antibodies that agonize or antagonize the activity of a DBT can be generated. Such antibodies can be tested using the assays described herein.

Assays for Identifying Agonists and Antagonists of DOUBLETIME

Identification of the DOUBLETIME protein provides a basis for screening for drugs capable of specific interaction with the functionally relevant aspects of the protein. For example, an agonist or antagonist can be identified that stimulate or inhibit the kinase activity of the DOUBLETIME protein. Since DOUBLETIME plays an important role regarding the stabilization of PER and therefore, the regulation of the biological clocks dependent on PER such agonists or antagonists can be used in treating disorders related to these biological clocks. Indeed, as described below, particular assays can be designed to identify drugs that particularly modulate the interaction between the PER protein and the DBT protein [including the human casein kinase Iε (CK1ε) protein]. In addition, the present invention envisions the use of alternative assays that can aid in distinguishing antagonists or agonists of the interaction of the DBT protein, e.g., CK1ε, with the PER protein in order to limit undesirable side effects on alternative biologically important substrates by such agents.

Accordingly, in addition to rational design of compounds that bind to DOUBLETIME, the present invention contemplates an alternative method for identifying specific agents that bind to DOUBLETIME using the various screening assays known in the art. Thus any screening technique known in the art can be used to screen for agonists or antagonists to the DOUBLETIME protein and/or its interaction with the PER protein including those performed using high throughput techniques and biological chip technology such as exemplified in U.S. Pat. No. 5,874,219, Issued Feb. 23, 1999, the disclosure of which is hereby incorporated by reference in its entirety. The present invention further contemplates screens for small molecule ligands or ligand analogs and mimics, as well as screens for natural ligands that bind to and antagonize DOUBLETIME in vivo.

Knowledge of the primary sequence of a factor of the present invention, see above, e.g., the DOUBLETIME protein, and the similarity of that sequence with proteins of known function, can provide an initial clue as to the agonists or antagonists of the protein. Identification and screening of antagonists is further facilitated by determining structural features of the DOUBLETIME protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, Volume 5*, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

The screening can be performed directly using peptides corresponding to the kiinase catalytic domain of DBT. Alternatively, chimeric proteins, which contain the kinase catalytic domain of DBT may be used, as such proteins will contain one element under investigation.

Screening can be performed with recombinant cells that express the DOUBLETIME protein, or alternatively, using purified protein, and/or specific structural/functional domains of the DOUBLETIME protein e.g., produced recombinantly, as described above. For example, a labeled DOUBLETIME protein can be used to screen libraries, as described in the foregoing references for small molecules that will inhibit the kinase activity of the DOUBLETIME protein.

The effective peptide(s) can be synthesized in large quantities for use in in vivo models and eventually in humans to modulate the DOUBLETIME protein. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, Vaccine 10:175–178 (1990)].

In addition, a potential drug, e.g., a modulating agent, can be obtained from a commercially available chemical library such as is available from most large chemical companies including Merck, Glaxo Welcome, Bristol Meyers. Squib, Monsanto/Searle, Eli Lilly, Novartis, and Pharmacia UpJohn. In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for modulators and/or binding partners of the DOUBLETIME protein.

The reagents that contain the DOUBLETIME protein or fragments thereof can be labeled for use in the screening assays. In one embodiment, the compound may be directly labeled including as part of a fusion protein, e.g., with green fluorescent protein. In another embodiment, a labeled secondary reagent may be used to detect binding of the compound to a solid phase support containing a binding molecule of interest. Binding may be detected by in situ formation of a chromophore by an enzyme label. Suitable enzymes include, but are not limited to, alkaline phosphatase and horseradish peroxidase. Other labels for use in the invention include colored latex beads, magnetic beads, fluorescent labels (e.g., fluorescein isothiocyanate (FITC), phycoerythrin (PE), Texas red (TR), rhodamine, Lucifer Yellow, AMCA blue, free or chelated lanthanide series salts, especially $Eu^{3+}$, to name a few fluorophores), chemiluminescent molecules, radio-isotopes, or magnetic resonance imaging labels.

As mentioned above, an important aspect of the present invention is the recognition of casein kinase I$\epsilon$ as a human homologue of DBT. Therefore, the present invention provides assays that can be used to identify agents/compounds that (i) bind to a mammalian PER protein (of which three are currently known) and affect the physical association between the PER protein and human CK1$\epsilon$ and/or (ii) affect the kinase activity of human CK1$\epsilon$ towards the PER protein substrate. Agents are selected that alter the binding constant of the physical association and/or the quantity or quality of phosphorylation of the PER protein by the CK1$\epsilon$ protein. Such assays can also be performed with active fragments of the PER protein and/or active fragments CK1$\epsilon$ protein. In this case an active fragment of the PER protein would minimally retain its CK1$\epsilon$ protein binding capacity and/or its phosphorylation site whereas the active fragment of the CK1$\epsilon$ protein would minimally retain its PER protein binding capacity and/or its kinase activity. Of course, the CK1$\epsilon$ protein, the PER protein and their corresponding active fragments could also be part of fusion proteins and peptides as described above.

For example, a chemical agent might be initially selected by its ability to bind to a PER protein or its ability to bind to a DBT, such as CK1$\epsilon$. It canbe subsequently tested to determine if it is a modulator of the physical association of PER with CK1$\epsilon$ in vitro and/or in a cultured cell expression assay. An agent that is selected as such a modulator is identified as an agonist if it increases the physical association between PER and CK1$\epsilon$ whereas a modulator is identified as an antagonist if it decreases the physical association. As discussed above, such binding agents could be small peptides or non-protein chemical agents.

An assay useful and contemplated in accordance with the present invention is known as a "cis/trans" assay. Briefly, this assay employs one or more constructs, which encode: a Per, Tim and DOUBLETIME (including the human CK1$\epsilon$) and a reporter gene that is under the control of the activated transcription factors e.g. the Tim-Per dimer. The contruct(s) are transfected into an appropriate cell line (preferably a mammalian cell line) and the expression of the reporter (such as luciferase, or green fluorescent protein) can be monitored. This assay may be performed to identify antagonists and agonists to the DOUBLETIME protein. For example, if it is desired to evaluate a compound as an agonist for the DOUBLETIME protein, a constuct is used that possesses a promoter linked to the reporter gene (e.g., luciferase) in which a response element is inserted that is ultimately under the control of the PER-Tim dimer (e.g., a response element for the per and/or tim genes). The resulting signal (chemiluminescence in this example) is then measured (photometrically in this example), and dose response curves are obtained and compared to those in which the agonist is not included in the assay. Since the DOUBLETIME protein serves to destabilize Per, and therefore inhibit the negative effect that Per has on its own transcription, an agonist for the DOUBLETIME protein should cause an increase in the transcription of a reporter gene that is ultimately under the control of the PER-Tim dimer. Protocols somewhat analogous to the one presented above can be found U.S. Pat. No. 4,981,784 and PCT International Publication No. WO 88/03168, for which purpose the artisan is referred. Additional assays that can be used to test potential agents/drugs can be readily adapted from the assays described below in the Examples and above in the Brief Description of the Drawings.

Kits

The present invention provides test kits for demonstrating the presence or absence of a DBT protein or nucleic acid encoding a DBT in a cellular sample. One such kit comprises a predetermined amount of a binding partner of the protein or nucleic acid. Preferably the binding partner is detectably labeled (such as a labeled antibody or nucleic acid probe). A preferred embodiment further comprises a predetermined amount of the DBT protein or nucleic acid encoding a DBT to be used as a standard. A kit of the present invention preferably also provides a protocol for using the kit.

The present invention further provides kits that can be used to identify agents/compounds that (i) bind to a mammalian PER protein (of which three are currently known) and affect the physical association between the PER protein and a DBT, such as human CK1$\epsilon$ and/or (ii) affect the kinase activity of the DBT (e.g., human CK1$\epsilon$) towards the PER protein substrate. One such kit comprises a predetermined amount of a DBT (e.g., human CK1$\epsilon$) or an active fragment thereof, and a predetermined amount of a PER protein or an active fragment thereof. As above, an active fragment of the PER protein would minimally retain its DBT protein binding capacity and/or its phosphorylation site, whereas the active fragment of the DBT protein would minimally retain its PER protein binding capacity and/or its kinase activity. Of course, the DBT protein, the PER protein and their corresponding active fragments could also be part of fusion proteins and peptides as described above. Preferably either the DBT protein or the PER protein are detectably labeled (e.g., as part of a fusion protein). Either the DBT protein or the PER protein can also be on a solid support. This kit preferably also provides a protocol for using the kit.

Labels

Suitable labels include enzymes and proteins such as green fluorescent protein, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme immunoassay ELISA and EMIT in *Methods in Enzymology*, 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Pat. No. 0372707 (application No. 89311108.8) by Sidney Pestka, or U.S. Pat. No. 5,459,240, issued Oct. 17, 1995 to Foxwell et al.

Proteins, including the DBTs of the present invention and antibodies thereto, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-metlionine, the invention further contemplates labeling with [$^{14}C$]-amino acids and [$^3H$]-amino acids (with the tritium substituted at non-labile positions).

Solid Supports

A solid phase support for use in the present invention will be inert to the reaction conditions for binding. A solid phase support for use in the present invention must have reactive groups in order to attach a binding partner, such as an oligonucleotide encoding a DBT, a DBT, or an antibody to a DBT, or for attaching a linker or handle which can serve as the initial binding point for any of the foregoing. In another embodiment, the solid phase support may be a useful chromatographic support, such as the carbohydrate polymers SEPHAROSE, SEPHADEX, and agarose. As used herein, a solid phase support is not limited to a specific type of support. Rather a large number of supports are available and are known to any person having skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California). In synthesis of oligonucleotides, a silica based solid phase support may be preferred. Silica based solid phase supports are commercially available (e.g., from Peninsula Laboratories, Inc.; and Applied Biosysterns, Inc.).

Antisense, Gene Targeting and Ribozymes

The functional activity of the DOUBLETIME protein can be evaluated transgenically. In one embodiment of this type, a transgenic mouse model is used. A DOUBLETIME gene for example, can be used in complementation studies employing transgenic mice. Transgenic vectors, including viral vectors, or cosmid clones (or phage clones) corresponding to the wild type locus of candidate gene, can be constructed using the isolated dbt gene. Cosmids may be introduced into transgenic mice using published procedures [Jaenisch, *Science*, 240:1468–1474 (1988)].

Alternatively, a transgenic animal model can be prepared in which expression of the dbt gene is either prevented or altered due to a disruption in its corresponding gene. Such alterations are exemplified below in Drosophila. Though a Drosophila are exemplified, other species including mice with altered dbt alleles are also part of the present invention. Altering a single allele may be preferable since in Drosophila such a single alteration appears to be dominant, and disruption of both alleles of dbt appeared to be lethal in Drosophila. Gene expression is disrupted, according to the invention, when no functional protein is expressed. Knock-out technology to delete a gene is described in U.S. Pat. No. 5,464,764 Issued Nov. 7, 1995 (herein incorporated by reference in its entirety.)

The present invention also extends to the preparation of antisense nucleotides and ribozymes that may be used to interfere with the expression of the dbt gene. This approach utilizes antisense nucleic acid and ribozymes to block translation of a specific mRNA, either by masking that mRNA with an antisense nucleic acid or cleaving it with a ribozyme. Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Res*, 15: 5749–5763 (1987); Marcus-Sekura *Anal. Biochem.*, 172:289–295 (1988); Brysch et al., *Cell Mol. Neurobiol.*, 14:557–568 (1994)]. Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient. Antisense methods have been used to inhibit the expression of many genes in vitro [Marcus-Sekura, *Anal.Biochem.*, 172:289–295 (1988); Hambor et al., *Proc. Natl. Acad. Sci.*

U.S.A. 85:4010–4014 (1988)] and in situ [Arima et al., *Antisense Nucl. Acid Drug Dev.* 8:319–327 (1998); Hou et al., *Antisense Nucl. Acid Drug Dev.* 8:295–308 (1998)].

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it [Cech, *JAMA*, 260:3030–3034 (1988); Cech, *Biochein. Intl*, 18:7–14 (1989)]. Because they are sequence-specific, only mRNAs with particular sequences are inactivated.

Investigators have identified two types of ribozymes, Tetrahymena-type and "hammerhead"-type [Haselhoff and Gerlach, *Nature* 334:585–591 (1988)]. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences of DOUBLETIME described herein may thus be used to prepare antisense molecules against, and ribozymes that cleave mRNAs encoding the DOUBLETIME protein.

Gene Therapy and Transgenic Vectors

In one embodiment, a gene encoding a DOUBLETIME protein is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), or a defective retrovirus such as HIV. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

For in vitro administration, an appropriate immunosuppressive treatment may be employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* 1:887–889 (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Haitmut et al., Canadian Patent Application No. 2,012,311, filed Mar. 15, 1990].

Administration

The nucleic acids encoding DBT (including human CK1ε) and fragments thereof, and the proteins and fragments encoded thereby, can be used to promote desired effects on circadian rhythms or related disorders. Thus such factors can be used in the treatment of numerous sleep-related disorders, including depression, narcolepsy, shift work, psychological disturbances associated with sleep disorder, and other mental disorders linked to the sleep-wake cycle. These proteins and nucleic acids can also be used in the treatment of jet lag. Similarly, the therapeutic administration of agents exhibiting mimicry or antagonism to a DBT such as the human CK1ε kinase, or antagonism to DBT binding activity toward PER, or antagonism to DBT kinase activity toward PER can also be used for the treatments of the conditions outlined above.

Thus, in instances where it is desired to reduce or inhibit the transcription of per or tim, an appropriate inhibitor of DBT could be introduced to stabilize PER and thereby aid in the inhibition of per and tim transcription.

DBT or a binding partner or agents exhibiting either mimicry or antagonism to DBT or control over its production, may be prepared in pharmaceutical compositions, with a suitable carrier and at a strength effective for administration by various means to a patient experiencing an adverse medical condition associated with PER or TIM. A variety of administrative techniques may be utilized, among them parenteral techniques such as subcutaneous, intravenous and intraperitoneal injections, catheterizations and the like. The precise doses used should be based upon the recommendations and prescription of a qualified physician or veterinarian.

Also, antibodies including both polyclonal and monoclonal antibodies, and drugs that modulate the production or activity of the DBT may possess certain diagnostic applications and may for example, be utilized for the purpose of detecting and/or measuring conditions such as to classify groups of individuals with sleep-related disorders, in order to better treat the disorders. For example, antibodies directed against a DBT, e.g., human CK1ε and/or PER can be used to aid in the diagnosing of the effects and/or in the evaluation of the therapies described above that are aimed at disturbing the normal interaction and inter-related functions of CK1ε and PER proteins.

A DBT (such as human CK1ε) may be used to produce both polyclonal and monoclonal antibodies in a variety of cellular media, by known techniques such as the hybridoma technique utilizing, for example, fused mouse spleen lymphocytes and myeloma cells. Likewise, small molecules that mimic or antagonize the activity(ies) of DBT may be identified (see above) or synthesized, and may be used in diagnostic and/or therapeutic protocols.

The present invention further contemplates therapeutic compositions useful in practicing the therapeutic methods of this invention. A subject therapeutic composition includes, in admixture, a pharmaceutically acceptable excipient (carrier) and DBT (such as human CK1ε), a polypeptide analog thereof or fragment thereof, as described herein as an active ingredient. In a preferred embodiment, the composition comprises an antigen capable of modulating the specific binding of DBT within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropyl amine, trimethylamine, 2-ethylamino ethanol, histidine, procaine, and the like.

The therapeutic polypeptide-, analog- or active fragment-containing compositions are may be administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

A subject in whom administration of the agent is an effective therapeutic regimen is preferably a human, but can be any animal, preferably a mammal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, or for veterinary medical use.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1
DOUBLE-TIME IS A NEW DROSOPHILA CLOCK GENE THAT REGULATES PERIOD PROTEIN ACCUMULATION Introduction Three alleles of a new Drosophila clock gene, double-time (dbt) have been isolated. Short ($dbt^S$) and long-period ($dbt^L$) mutants alter both behavioral rhythmicity and the molecular oscillations of the protein products of the two previously identified clock genes, period and timeless. This indicates that dbt encodes a central clock component. A third allele, $dbt^P$, is associated with pupal lethality and eliminates circadian cycling of per and tim gene products in larvae. In $dbt^P$ mutants, PERIOD (PER) protein constitutively accumulates to very high levels, is no longer dependent on TIM for its accumulation and remains hypo-phosphorylated. Evidence is presented for altered PER stability in $dbt^S$ and $dbt^L$ mutants. The results presented herein are consistent with the normal function of DOUBLETIME protein (DBT) being to reduce the stability and thus the level of accumulation of monomeric PER proteins. This would promote a delay between per/tim transcription and PER/TIM complex function, which is essential for molecular rhythmicity.

Experimental Procedures

Mutagenesis and Genetic Crosses: en bw males were mutagenized with EMS (denoted by *) as described [Lewis and Bacher, *Dros. Inf. Serv.* 43:193 (1968)] and mated to virgin females. Two cross strategies were employed. Strategy I generated lines with isogenous second chromosomes, while strategy II allowed the $F_1$ generation to be screened for dominant or semidorminant mutations on the second or third chromosome.

Strategy I:
1) cn bw*/cn bw* males X CyO/Sco virgins
2) cn bw*/(CyO or Sco) single $F_1$ male X CyO/Sco virgins
3) cn bw*/CyO $F_2$ males X cn bw*/CyO $F_2$ females
4) Screen cn bw*/cn bw* males in locomotor assays.

Strategy II
1) en bw*/cn bw* males X TM3, Ser/Sb virgins
2) assay locomotor activity of male progeny, and if aberrant phenotype is displayed, cross cn bw*/+; */Sb single $F_1$ male X TM3, Ser/Sb and Sp/SM5 virgins 3) rescreen locomotor activity of male progeny, and if aberrant phenotype is reproduced, establish lines with isogenous second or third chromosomes:
   a) (cn bw* or+)/+; */TM3, Ser F$_2$ males X TM3, Ser/Sb virgins
   b) cn bw*/SM5; +/Sb males X Sp/SM5 virgins Locomotor Assays and Eclosion Assays: Flies were first entrained to 12 hr of light followed by 12 hrs of darkness at 25° C. (LD), and then transferred to constant darkness at 25° C. for the DD assays. Monitoring and analysis of locomotor activity of individual flies, and chi-square periodogram analysis, was as described previously [Sehgal et al., *Proc. Natl. Acad. Sci. USA*, 89:1423–1427 (1992)].

For eclosion assays, populations of flies with the indicated genotypes were reared in pint-size plastic bottles and entrained in LD. They were then transferred to DD, and emerging adults collected and counted every two hours. Bottles in DD were handled under a darkroom red light (15 W bulb, Kodak GBX-2 filter), the wavelength of which has no effect on Drosophila circadian rhythms.

Recombination and Complementation Tests: Flies from the dbt$^S$ lines were crossed to several different lines containing multiple mutations on their third chromosomes. Heterozygous females containing a third chromosome from the dbt$^S$ line and a third chromosome with these other mutations (dbt$^S$/multiple mutations) were mated to males from a third chromosome balancer stock (TM3,Sb Ser/D), so that individual recombinant chromosomes could be recovered in male progeny which also carried the balancer chromosome (TM3,Sb Ser/recombinant chromosome). Lines were established from each individual male (TM3,Sb Ser/recombinant male X TM3,Sb Ser/D virgins), and multiple individuals from each line were scored for the presence or absence of all the mutations, including dbt$^S$ (which by definition leads to short-period locomotor activity).

For the deficiency analysis, flies from the dbt$^S$ and dbt$^L$ stocks were crossed to the following stocks obtained from the Drosophila Stock Center (Bloomington, Ind.): Df(3R) XTA1 (96A17-21;96D1-2), Df(3R)T1-I (97B;97E), Df(3R) T1-X (97B;97D1-2), Df(3R)T3450 (98E3;99A6-8), Df(3R) X3F (99D1-2;99E1), Df(3R)awdKRB (100C;100D), Df(3R)T1-P (97A;98A1-2), Df(3R)ro80b (97D1;97D13), Df(3R)tll-g (99F1-2;100B5).

The duplication employed came from Df(3R)R133, B(S)/TM3; Dp(3;1)124P. A recombinant chromosome was produced in which the mutation bv (distal to 100B5) was linked to dbt$^S$ (see recombination test 3, table 2). This chromosome was introduced into a line in which the X chromosome was either normal or contained a duplication [Dp(3:1)124P] of the right tip of the third chromosome (includes 99E to 100F). The presence of the duplication was detected by absence of the bv mutant phenotype (short bristles), since the duplication contains a wild-type copy of the bv gene that rescues the phenotype.

Larval culture: Larvae were entrained for at least 3 days before an experiment in a standard 12 h:12 hr light:dark cycle at 25° C. Immunocytochemistry: Larval brains were processed for immunocytochemistry using a modified protocol of Kunes et al. [*J. Neurosci.*, 13:752–767 (1993)]. Brains were dissected from entrained wandering third instar larvae, treated with 1 mg/ml Sigma blend collagenase in PBS with 50 mM CaCl$_2$ for 15 min at room temperature, and then fixed for 30 min in 4% paraformaldehyde in PBS. Including a collagenase pre-treatment gave a stronger signal for TIM than omitting it—therefore TIM is not light-sensitive in the short time before fixing. Brains were permeabilized and rinsed in PBS, 1% Triton for 2 periods of 20 min, and then blocked in PBS, 0.5% Triton (PBT) with 10% heat inactivated goat serum for 1 hr or longer. Primary antibodies were incubated overnight at 4° C. in blocking solution. Anti-TIM 316, anti-PER [Stanewsky et al., *J. Neurosci.*, 17:676–696 (1997)], and anti-lacZ (Promega) were used at dilutions of 1:1500, 1:16,000 and 1:1,000 respectively. PER and TIM antisera were pre-absorbed against per$^o$ or tim$^{01}$ embryos, and neither antibody gave significant staining on the relevant control (respectively per$^o$ or tim$^{01}$ larval brains). The rest of the procedure was carried out at room temperature according to standard procedures. The results shown are representatives of at least 20 larvae analyzed for each time shown in independent experiments, which all had results consistent with one another.

In situ hybridization: In situ hybridizations were performed essentially as described in Tautz and Pfeifle [*Chromosoma* 98:81–85 (1989)] except that proteinase K was used at 5 mg/ml. The TIM probe was synthesized from pSK-TIM2 [Myers et al., *Nucl. Acids Res.*, 25:47 10–20 1714 (1997)] using DIG RNA labeling mix (Boehringer Mannheim) according to manufacturer's instructions.

RNase protection: 100 larval brains were dissected in PBS, placed into RNAzol (TelTest), frozen on dry ice, thawed and RNA isolated according to the manufacturer's instructions. 10 mg RNA (approximately 50 brains) were used for one lane of an experiment. RNase protections used the Ambion RPAII kit according to manufacturer's instructions. The per $^{32}$P-labeled riboprobe protects nucleotides 1426–1749 of the per cDNA; the tim probe was as in Myers et al. [*Nucl. Acids Res.*, 25:4710–1714 (1997)]; and the rp49 probe protects nucleotides 323–381 of the rp49 cDNA. per and tim probes were synthesized with only radioactive UTP, while synthesis of the rp49 probe included 5 mM non-radioactive UTP.

Western blotting: For adult head Western blots, extracts were made as in Edery et al., [*Proc. Natl. Acad. Sci. USA*, 91:2260–2264 (1994)], and 100 mg protein loaded per lane. For larval brain extracts, 10 larval brains were dissected in PBS, frozen, boiled in 30 ml 1.1×SDS loading buffer, spun and the supernatant loaded on a gel. All samples were run on 5.7% (75:1) SDS-polyacylamide gels [Edery et al., *Proc. Natl. Acad. Sci. USA*, 91:2260–2264 (1994)]. They were transferred with either a semi-dry or wet transfer apparatus according to manufacturer's instructions (Bio-Rad). Blots were incubated overnight at 4° C. with either anti-PER [Stanewsky et al., *J. Neuronsci*, 17:676–696)1997)] or anti-TIM [Myers et al., *Nucl. Acids Res.*, 25:4710–1714 (1997) at dilutions of 1:10,000 or 1:2,000 respectively. For washes, secondary antibody incubation, and ECL (Amersham), we followed standard procedures.

Results

Double-time is a New Gene that Alters the Period of Locomotor Activity Rhythms of Drosophila: Ethyl methane sulfonate (EMS) mutagenesis was used to induce new clock mutations affecting the period length of locomotor activity rhythms in homozygous or heterozygous flies (Experimental Procedures). Screening of heterozygous phenotypes was performed because all known clock mutations that affect period length in Drosophila, Neurospora, Arabidopsis, mice, and hamsters, are semi-dominant [reviewed by Dunlap, *Genet*, 30:579–601 (1996)].

The locomotor activity of individual flies, each bearing heterozygous or homozygous mutagenized chromosomes, was monitored under constant darkness (DD), to reveal free-running period length (Experimental Procedures, above). From a screen of ~15,000 second and third chromosomes, three lines were recovered carrying long-period alleles of timeless. Two additional lines were isolated that contained mutations in a new clock gene, which is named doubletime (dbt), because the first mutant allele to be isolated (dbt$^S$) dramatically shortens the behavioral period (described below). The second dbt allele (dbt$^L$) lengthens the period.

TABLE 1

Locomoter Activity of dbt Flies in DD

| genotype | tau ± SEM | (#AR/n) |
|---|---|---|
| dbt$^S$ | 18.0 ± 0.1 | (4/24) |
| dbt$^S$/+ | 21.8 ± 0.2 | (0/10) |
| +/+ | 23.8 ± 0.1 | (0/9) |
| dbt$^L$ | 26.8 ± 0.1 | (0/19) |
| dbt$^L$/+ | 24.9 ± 0.1 | (1/17) |
| +/+ | 23.6 ± 0.1 | (0/15) |

The average period (tau) of each genotype is indicated. The dbt/+ and +/+ genotypes in each group came from the progeny of a cross between dbt/+ parents. #AR/n, number of arrhythmic flies/total number of flies assayed.

Figure 1B:
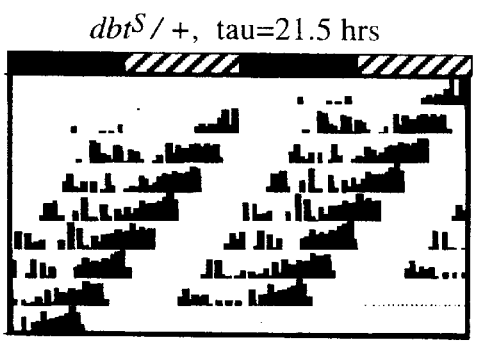
Figure 1C:
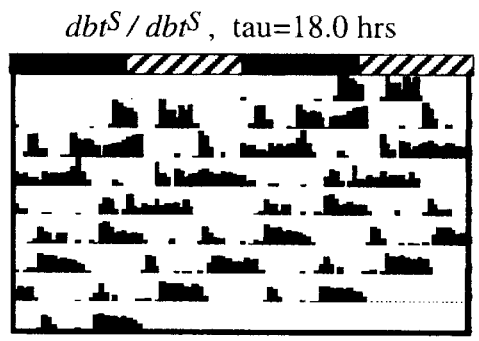
Figure 1D:
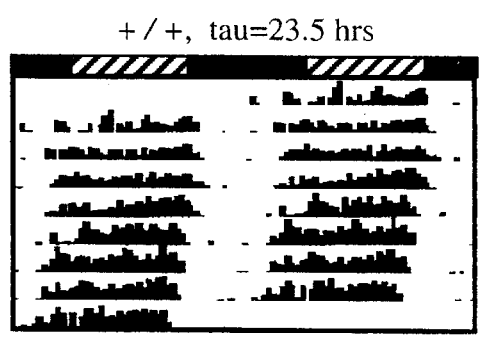
Figure 1E:
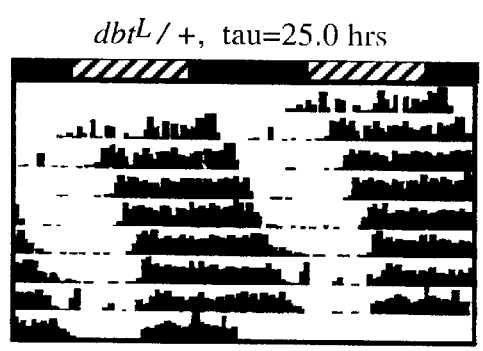
Figure 1F:
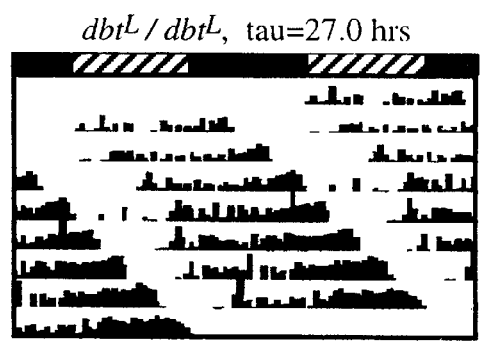

Flies that are heterozygous for the dbt$^S$ mutation (dbt$^S$/+) produce locomotor rhythms with an average period of 21.8 hrs in DD (FIG. 1B and Table 1), while homozygous flies (dbt$^S$/dbt$^S$) produce locomotor rhythms with an average period of 18.0 hrs (FIG. 1C and Table 1). Flies that are heterozygous for the dbt$^L$ mutation (dbt$^L$/+) produce locomotor rhythms with an average period of 24.9 hr (FIG. 1E and Table 1), while homozygous flies (dbt$^L$/dbt$^L$) produce locomotor rhythms with 26.8 hr periods (FIG. 1F and Table 1). Because dbt$^S$/+ and dbt$^L$/+ flies have shorter and longer periods, respectively, than wild type controls, but not as short or long as homozygous mutant flies, dbt$^S$ and dbt$^L$ are semi-dominant. Homozygous dbt$^S$ and dbt$^L$ flies can be entrained by an imposed 12 hr light: 12 hr dark cycle (LD 12:12) since they exhibit 24 hr periodicity under such conditions. Analysis of several hundred locomotor activity records from homozygous dbt$^S$ and dbt$^L$ flies indicated complete penetrance of the mutant phenotypes.

The dbt$^S$ mutant was also tested for aberrant circadian rhythms of eclosion (emergence of the adult fly from the pupal case) to determine whether dbt mutations affect this phenotype as previously observed for per and tim [Konopka and Benzer, et al., *Proc. Natl. Acad. Sci. USA*, 68:2112–2116 (1971); Sehgal et al., *Science*, 263:1603–1606 (1994)]

Figure 2:
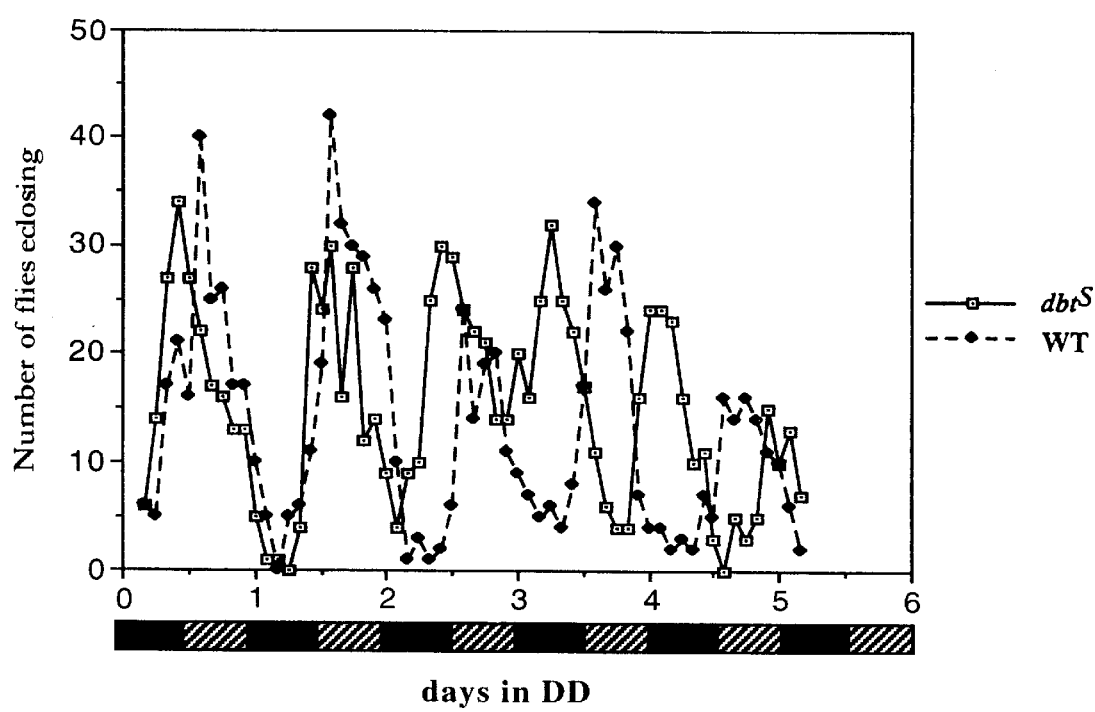
FIG. 2 shows the circadian rhythm of eclosion has a shorter period in $dbt^S$ flies than in wild type flies. Bottles of wild type (wt) and $dbt^S$ flies were maintained in LD 12 hr: 12 hr for 10 days at 25° C. At the end of the final 12 hr period of light (day 0 on the plot), the bottles were cleared of adult flies and transferred to constant darkness (DD). Newly emerged adults were cleared and counted every 2 hours. A Kodak safelight with a 15 W bulb and a GBX-2 filter, which blocks wavelengths less than 600 nm, was used to collect the flies. The phase of the previous light:dark regime is indicated at the bottom, with the hatched boxes indicating the time of the photophase.

Although eclosion occurs only once in the lifetime of an individual fly, it occurs repeatedly and rhythmically in a population of flies of diverse ages. In DD, the period of the dbt$^S$ eclosion rhythm was shorter than the rhythm of the wild type population. Peaks of eclosion occurred progressively earlier in dbt$^S$ as compared to wild type over the 5 day interval tested (FIG. 2). The parallel effects of the dbt$^S$ mutation on two behavioral outputs of the Drosophila circadian clock are consistent with an effect on the central pacemaker mechanism rather than on a specific output pathway. In this regard, the effects of dbt mutations on rhythmicity are comparable to those of period and timeless mutations (see also below).

Genetic Tests Co-Localize the dbt$^S$ and dbt$^L$ Mutations to the Right Arm of the Third Chromosome: Flies from the dbt$^S$ stock were crossed to Drosophila stocks containing multiple third chromosome mutations and individual recombinant F$_2$ progeny used to establish lines. Locomotor activity rhythms were analyzed for several representatives from each recombinant line to verify the presence or absence of the dbt$^S$ mutation. These recombination tests placed the dbt$^S$ mutation near the tip of the right arm of chromosome 3 between claret (ca) and brevis (bv), and closely linked to loboid (ld) (Table 2).

TABLE 2

Recombination Analysis of dbt$^S$

| Parental Chromosome | Recombinant Chromosome | Frequency |
|---|---|---|
| (ru$^-$ h$^-$ th$^-$ st$^-$ cu$^-$ sr$^-$) e$^-$ ca$^-$ dbt$^+$ | e$^-$ ca$^-$ dbt$^S$ | 0/38 |
| (ru$^+$ h$^+$ th$^+$ st$^+$ cu$^+$ sr$^+$) e$^+$ ca$^+$ dbt$^S$ | e$^+$ ca$^-$ dbt$^S$ | 0/38 |
|  | e$^+$ ca$^+$ dbt$^+$ | 2/38 |
|  | e$^-$ ca$^+$ dbt$^+$ | 0/38 |
|  | e$^-$ ca$^+$ dbt$^S$ | 6/38 |
|  | e$^+$ ca$^-$ dbt$^+$ | 6/38 |
| (h$^-$ th$^-$ st$^-$ cu$^-$ sr$^-$) e$^-$ [ld$^+$, dbt$^S$] | e$^-$ [ld$^+$, dbt$^{+}$] | 0/50 |
| (h$^+$ th$^+$ st$^+$ cu$^+$ sr$^+$) e$^+$ [ld$^-$, dbt$^+$] | e$^+$ [ld$^+$, dbt$^{+}$] | 0/50 |
|  | e$^+$ [ld$^-$, dbt$^S$] | 0/50 |
|  | e$^-$ [ld$^-$, dbt$^S$] | 0/50 |
|  | e$^-$ [ld$^-$, dbt$^+$] | 12/50 |
|  | e$^+$ [ld$^+$, dbt$^S$] | 4/50 |
| ca$^-$ dbt$^+$ bv$^-$ | ca$^-$ dbt$^S$ bv$^+$ | 2/93 |
| ca$^+$ dbt$^S$ bv$^+$ | ca$^-$ dbt$^+$ bv$^+$ | 0/93 |
|  | ca$^+$ dbt$^+$ bv$^-$ | 2/93 |
|  | ca$^+$ dbt$^S$ bv$^-$ | 1/93 |
|  | ca$^+$ dbt$^+$ bv$^+$ | 0/93 |
|  | ca$^-$ dbt$^S$ bv$^-$ | 0/93 |

Flies with the indicated parental chromosomes were mated, and F1 heterozygous females were mated to males with the TM3 balancer. Single F$_2$ male progeny with TM3 were mated to TM3 females to establish a line. The dbt allele of each line was scored by locomotor assays of multiple individuals in DD, while the other markers were scored visually in homozygous flies. Recombination events between the markers in parentheses () are not tabulated here.

dbt$^S$ and dbt$^L$ were also genetically localized by complementation analyses with a series of deficiencies affecting the right arm of chromosome 3 (see Experimental Procedures, above, for a complete list of the deficiencies tested). One deficiency, Df(3R)tll-g, produced flies with 19.1 hr locomotor rhythms in dbt$^S$/Df heterozygotes, and 27.2 hr rhythms in dbt$^L$/Df heterozygotes (Table 3). Df(3R)tll-g/+ heterozygotes produced flies with wild type periods (~24 hr). These results argue that this deficiency lacks the wild-type allele of dbt. The deficiency is missing polytene chromosomal region 99E–F to 100B, which is distal to ca. The results are consistent with the recombination analysis of dbt$^S$.

Figure 3A:
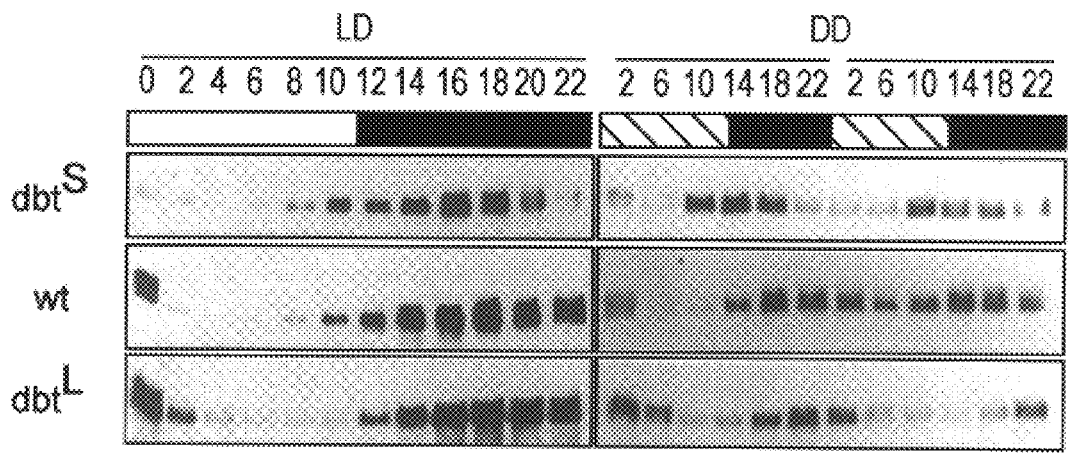
FIGS. 3A–3C shows the timing of PER and TIM oscillations are altered in $dbt^S$ and $dbt^L$ adult heads. Western blot analysis of TIM (FIG. 3A) and PER (FIG. 3B) from $dbt^S$ (top), wild-type, wt, (middle) and $dbt^L$ (bottom) fly head extracts during one day of LD, and two days of DD. The times of collection are indicated above the blots. Total protein levels in all lanes of a panel were judged to be similar by comparing a slower running cross-reacting band. Note the successive phase changes in DD for $dbt^S$ and $dbt^L$ respectively.

Duplication analysis was also performed. dbt$^S$/dbt$^S$ flies carrying Dp(3;1)124P, which includes chromosomal region 99E–100F, produced locomotor activity rhythms with a period of 21.2 hr (Table 3; Experimental Procedures, above). Hence, dbt is contained within the duplicated region. The duplication had no significant effect on the period of the rhythm of wild type flies indicating that an essentially wild type rhythm is obtained with 1, 2 or 3 doses of wild type dbt.

dbt$^S$ and dbt$^L$ Alter the Periods of PER and TIM Protein Oscillations: To investigate whether dbt period-altering alleles change the molecular oscillation of known clock components, PER and TIM protein time-courses were looked at on Western blots. One day of LD, and two days of DD were assayed for wild type, dbt$^S$ and dbt$^L$ genotypes (FIG. 3). Overall, the levels of expression of both PER and TIM are not grossly altered. However. in LD, both proteins oscillate with a slight phase advance in dbt$^S$, and phase delay in dbt$^L$. In DD, the protein levels oscillate with a period length corresponding to the locomotor activity rhythms of the mutants. Hence, mutations at dbt that change behavioral rhythms also change molecular oscillations of PER and TIM.

Figure 3B:
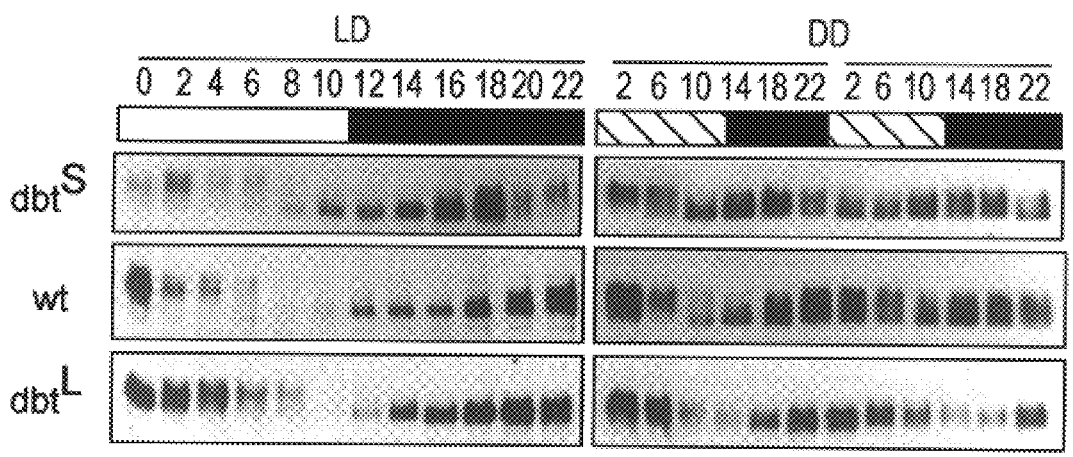
Figure 3C:
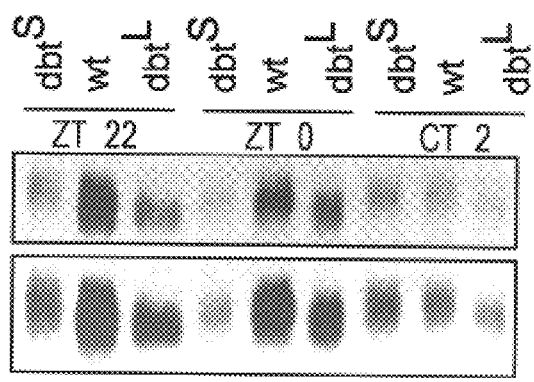

A closer inspection of dbt$^S$ reveals that both PER and TIM disappear prematurely in an LD cycle. Forms of PER with lowest electrophoretic mobility, which have been associated with highest levels of PER phosphorylation [Edery et al.,

*Proc. Natl. Sci. Acad. USA*, 91:2260–2264 (1994)], appear earlier than in wild type (FIG. 3C). In contrast, in dbt$^L$, both PER and TIM are detectable for an extended period of time in DD (see LD to DD transition, FIG. 3A–3B), and the appearance of low mobility forms of PER is delayed (FIG. 3C). In contrast to wild type flies, persistence of PER in the absence of TIM after lights-on in an LD cycle in dbt$^L$ are detected(FIG. 3B). This effect suggests unusual persistence of monomeric PER proteins after TIM is eliminated by light. The higher level of PER from ZT2–6 (ZT, zeitgeiber time, indicates time in LD cycles) is not simply due to increased PER levels in dbt$^L$, since a side by side comparison of PER proteins in wild type and dbt$^L$ at ZT0 shows roughly equal amounts of PER (FIG. 3C). Thus, there seems to be an increase in PER stability in dbt$^L$. Conversely, dbt$^S$ may cause premature degradation of both PER and TIM.

Isolation of a P Element Insertion in the dbt Locus: Drosophila strains containing single P element insertions on the right arm of the third chromosome were screened for failure to complement the original dbt$^S$ mutation. One strain, referred to hereafter as dbt$^P$, behaved like the Df(3R)tll-g deficiency. dbt$^S$/dbt$^P$ flies produced locomotor activity rhythms with a period of 19 hr, while dbt$^P$/+ flies had wild-type periods (23.8 hrs; Table 3). Similarly, dbt$^L$/dbt$^P$ flies had locomotor activity rhythms of 26.6 hrs, similar to those obtained in dbt$^L$/Df(3R)tll-g flies (Table 3). The P element is therefore likely to result in a large reduction, or even absence, of dbt gene products (demonstrated in Example 2, below). The finding that dbt$^P$ fails to complement both dbt$^S$ and dbt$^L$, indicates that the latter mutations affect the same gene, a conclusion that has been confirmed by molecular studies described in Example 2.

TABLE 3

Complementation of Analysis of dbt

| genotype | tau ± SEM | (#AR/n) |
| --- | --- | --- |
| dbt$^S$/Df(3R)tllG | 19.1 ± 0.04 | (1/25) |
| dbt$^S$/TM6B | 21.7 ± 0.1 | (1/11) |
| Df(3R)tllG/TM3 | 24.8 ± 0.2 | (3/5) |
| dbt$^S$/dbt$^P$ | 19.0 ± 0.1 | (1/11) |
| dbt$^S$/TM3 | 21.8 ± 0.3 | (1/4) |
| dbt$^P$/TM3 | 23.8 ± 0.1 | (0/4) |
| Dp(3;1)124P; dbt$^S$/dbt$^S$ | 21.2 ± 0.1 | (1/7) |
| dbt$^S$/dbt$^S$ | 18.4 ± 0.1 | (3/10) |
| Dp(3;1)124P; dbt$^S$/dbt$^+$ | 22.5 ± 0.2 | (0/5) |
| dbt$^S$/dbt$^+$ | 22.4 ± 0.1 | (0/4) |
| dbt$^L$/Df(3R)tllG | 27.2 ± 0.1 | (0/16) |
| dbt$^L$/TM3 | 25.1 ± 0.1 | (1/14) |
| Df(3R)tllG/TM3 | 24.7 ± 0.3 | (1/6) |
| dbt$^L$/dbt$^P$ | 26.6 ± 0.1 | (0/15) |
| dbt$^L$/TM3 | 25.0 ± 0.1 | (0/14) |
| dbt$^P$/TM3 | 24.4 ± 0.3 | (0/8) |
| dbt$^S$/TM3 | 21.5 ± 0.1 | (0/19) |
| dbt$^L$/dbt$^S$ | 22.9 ± 0.1 | (0/15) |
| dbt$^L$/TM3 | 24.9 ± 0.1 | (0/13) |
| dbt$^P$/Df(3R)tllG | † | |

Lines with the three alleles of dbt (dbt$^S$, dbt$^L$, and dbt$^P$) were crossed to each other and to lines containing Df(3R)tllG or DP(3;1)124P, and progeny with the indicated genotypes were tested in locomotor assays in DD. The average period (tau) of each genotype is indicated. Genotypes in each group came from the same cross. #AR/n, number of arrhythmic flies/total number of flies assayed. † indicates no progeny survived to adulthood.

Recessive lethality is associated with the dbt$^P$ strain, as no adults of the genotype dbt$^P$/dbt$^P$ or Df(3R)tll-g/dbt$^P$ have been recovered (Table 3). A strain, dbt$^P$/TM6, that produces homozygous larvae and pupae distinguishable from their heterozygous siblings by virtue of the dominant marker Tubby (on TM6), was constructed. Most third-instar homozygous dbt$^P$ larvae pupate, but die later in pupal development. Proof that dbt function is required for both viability and circadian rhythmicity has come from reversion studies of dbt$^P$ (Example 2, below). Using Third Larval Instar Brain Clock Cells to Analyze dbt$^P$: The strongly hypomorpllic allele, dbt$^P$, was hypothesized to show the most dramatic effects on clock gene cycling. Although dbt$^P$ embryos take longer to develop into third instar larvae than do their heterozygous siblings, the foraging motility of these larvae and their touch sensitivity appear normal. In the analyses below, only clearly motile larvae were used.

Behavioral studies have demonstrated that a circadian clock is active in Drosophila larvae [Sehgal et al., *Proc. Natl. Acad. Sci. USA*, 89:1423–1427 (1992)]. It has recently been shown that a specific group of central brain cells is likely to compose the larval pacemaker [Kaneko et al., *Neurosci*, 17:6745–6760 (1997)]. In each hemisphere of the third instar larval brain, four to five cells co-express PER and TIM with circadian oscillations that are in phase with the oscillations of these proteins in adult pacemaker cells (LNs) (FIGS. 4A and 5A) [Kaneko et al., *J. Neurosci.*, 17:6745–6760 (1997]. The only detectable staining in the hemispheres of the larval brain for pigment-dispersing hormone (PDH), a marker for adult lateral neurons [Helfrich-Forster, *Proc. Natl. Acad. Sci. USA*, 92:612–616 (1995)], is found in the axons of these PER-TIM expressing cells [Kaneko et al., *J. Neurosci.*, 17:6745–6760 (1997)]. Therefore, the PER-TIM-PDH co-expressing larval brain cells can be considered larval lateral neurons (1vLNs). In per$^o$ larvae, TIM is constitutively cytoplasmic in 1vLNs (FIG. 4C), and in tim$^{01}$ larvae, PER is undetectable in these cells by immunocytochemistry. Both of these mutant phenotypes are characteristics of adult clock cells [Vosshall et al., *Neuron*, 15:345–360 (1994); Myers et al., *Science*, 271:1736–1740 (1996)]. PER and TIM oscillations can also be seen in two groups of cells at the anterior of the third instar larval brain, but in one of these groups, the oscillations are out of phase with the 1vLNs [Kaneko et al., *J. Neurosci.*, 17:6745–6760 (1997)]; {FIGS. 4A and 4B), and may be regulated by activity of the 1vLNs [Kaneko et al., *J. Neurosci.*, 17:6745–6760 (1997)]. These oscillations are not as robust as in the 1vLNs.

The 1vLNs were initially examined to see if they were still present in dbt$^P$ larvae. In a total of 13 dbt$^P$ larval brains (25 hemispheres) in either LD or DD, PDH staining was detected in the cytoplasm of precisely 4 cells in each hemisphere, as seen for wild-type larvae [Kaneko et al., *J. Neurosci.*, 17:6745–6760 (1997)]. The axons of these dbt$^P$ 1vLNs fasciculate and head to the anterior of the brain as in wild type. However, dbt$^P$ 1vLNs are found slightly more peripherally than in wild-type, as seen in the staining patterns of PER and TIM in FIGS. 4A, 4B, 5A and 5E.

Figure 4A:
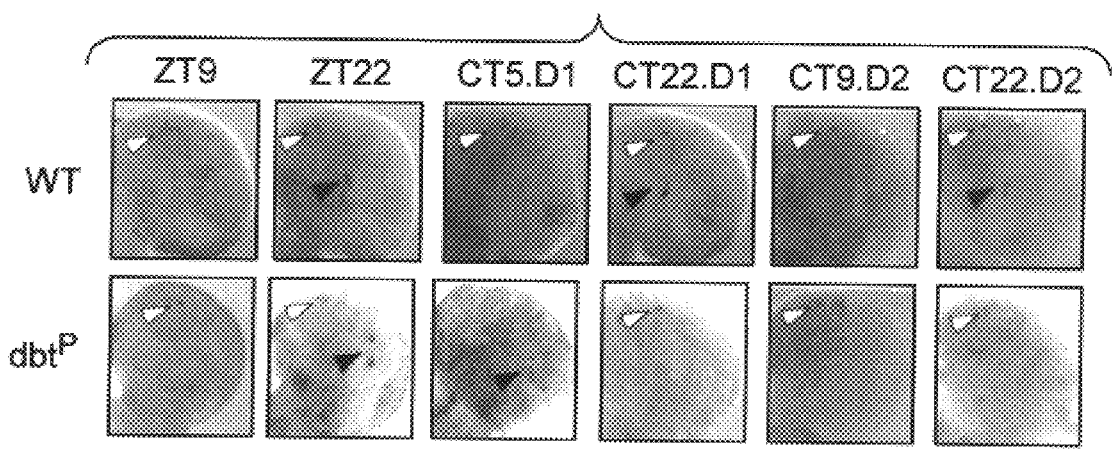
FIGS. 4A–4C shows the Circadian oscillations of tim RNA and protein are blocked in $dbt^P$ third instar larval brains. Larvae were entrained for at least 3 days in standard LD cycles, with some transferred to DD for either one (D1) or two (D2) further days. Larval brains were isolated at the times shown (ZT and CT indicate time in LD and DD cycles respectively), and processed for either TIM protein (A, C), or tim RNA (B) as described (see Experimental Procedures in Example 1, below). Representative single hemispheres are shown in FIG. 4A and 4B. Closed arrowheads indicate 1vLNs, and open arrowheads indicate out of phase cells (see text of Example 1). Wild type brains (WT, top panels in FIG. 4A and 4B) show oscillations of TIM protein and tim RNA in 1vLNs in both LD and DD cycles. In contrast, 1vLNs of $dbt^P$ brains (bottom panels in FIG. 4A and 4B) show oscillations of TIM protein and tim RNA only in LD. On transfer to DD, TIM protein and tim RNA persist weakly in 1vLNs at CT5 or CT2 respectively, and are subsequently not detected. TIM protein and tim RNA levels oscillate in out of phase cells in wild type, albeit more weakly than in 1vLNs, whereas significant oscillations are not seen in these cells in $dbt^P$. TIM protein is detected in $dbt^P$ brain hemispheres in the out of phase cells at CT5, but in the panel shown, visualization required a slightly different optical plane. The 1vLNs in $dbt^P$ are found more peripherally than in wild type, as seen for PDH expression (see text, Example 1).

Regulation of TIM's Light-Sensitivity and Nuclear Localization are not Affected by dbt$^P$: In an LD cycle, TIM oscillates in the 1vLNs in both wild-type and dbt$^P$ larvae, and is detected only during the dark phase of the cycle (FIG. 4A compare ZT9 and 22). Therefore, the light sensitivity of TIM in 1vLNs is not affected in a strongly hypomorphic dbt background. In contrast to wild type, TIM can be detected in the out of phase cells in dbt$^P$ larvae at both day and night time-points, indicating that dbt$^P$ blocks molecular cycling in these cells, and, as previously shown by [Kaneko et al., *J. Neurosci.*, 17:6745–6760 (1997)], that TIM fails to show light sensitivity in the out of phase cells. TIM accumulation was also examined in per$^o$ and per$^o$; dbt$^P$ larvae. TIM accumulated at night in the cytoplasm of 1vLNs in both strains in contrast to the predominantly nuclear localization observed in wild-type (FIG. 4C). A similar cytoplasmic accumulation of TIM is observed in the photoreceptors and LNs of adult per° Drosophila [Myers et al., *Science*, 271:1736–1740 (1996)]. Therefore dbt has no role in retaining TIM in the cytoplasm in the absence of PER [Myers et al., *Science*, 271:1736–1740 (1996); Saez and Young, *Neuron*, 17:911–920 (1996)].

Oscillations of TIM Protein and tim RNA Cease in $dbt^P$ Larval Brains in Constant Darkness: When wild-type larvae are transferred to constant darkness, TIM continues to oscillate robustly with only night time TIM accumulation in the 1vLNs, and subjective day time TIM accumulation in the out of phase brain cells (FIG. 4A; Kaneko et al., *J. Neurosci.*, 17:6745–6760 (1997)]. In contrast, in $dbt^P$ larvae transferred to DD, TIM is weakly detected in 1vLNs in the first subjective morning at CT5 (CT, circadian time, indicates time in DD), disappears by CT10 and is undetectable thereafter in the 1vLNs (FIG. 4A). TIM is detected in $dbt^P$ in the out of phase larval brain cells in DD as in LD. The staining in these cells serves not only as a positive control for the procedure, but also indicates that in DD, $dbt^P$ blocks molecular cycling in both the 1vLNs and in the out of phase brain cells. For the 1vLNs, the differential effects of $dbt^P$ on TIM in LD and DD shown in FIG. 4A are not due to selecting larvae from slightly different developmental stages since identical results were derived from larvae that had been synchronized developmentally.

Figure 4B:
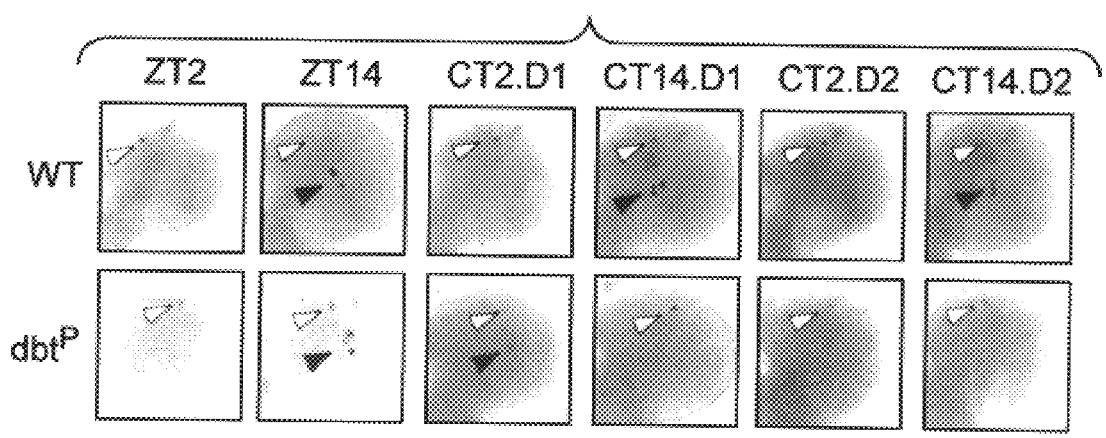
Figure 4C:
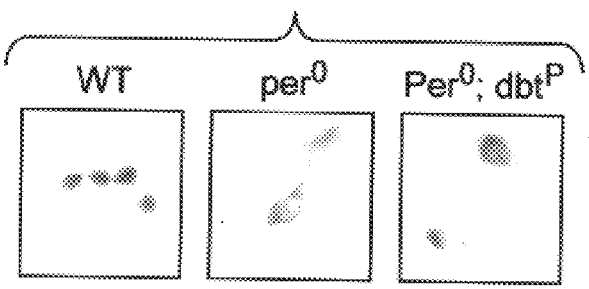

In wild-type larvae, tim RNA, as detected by in situ hybridization with an antisense tim probe, shows robust oscillations in the 1vLNs both in LD and in DD (FIG. 4B). Cycling is also seen for tim RNA in the out of phase brain cells, with the expected phase difference (FIG. 4B). tim RNA levels oscillate in the 1vLNs of $dbt^P$ mutants in an LD cycle (FIG. 4B), indicating that PER/TIM complexes can still negatively regulate tim gene expression in $dbt^P$ larvae, and that this regulation can be blocked by light-dependent degradation of TIM. When $dbt^P$ larvae are transferred to DD, tim RNA is weakly detected in 1vLNs on the first subjective morning (CT2), but is undetectable thereafter in these cells (FIG. 4B). In DD and LD, tim RNA is detected in the out of phase brain cells of $dbt_P$ larvae. Thus the effects of the $dbt^P$ mutation on levels of TIM protein (FIG. 4A) probably reflect more direct effects of $dbt^P$ on tim RNA levels (FIG. 4B).

Figure 5A:
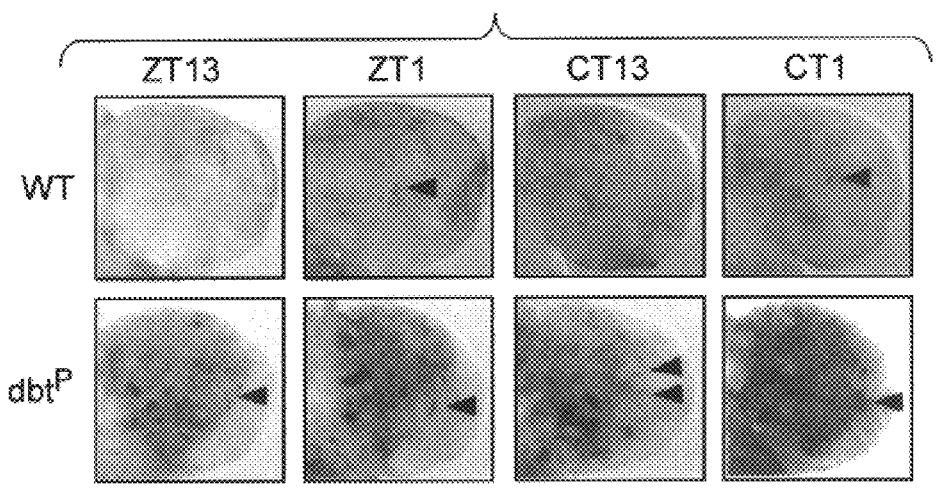
FIGS. 5A–5E show that PER accumulates to unusually high levels in $dbt^P$ third instar larval brains.
Figure 5B:
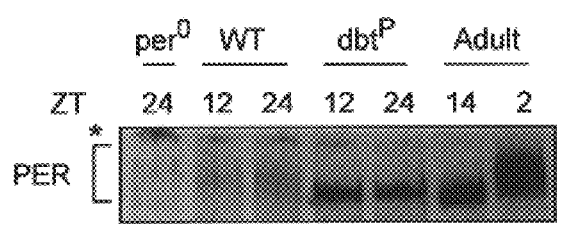

PER is Constitutively Expressed at High Levels in $dbt^P$ Larval Brains: PER protein levels oscillate in the 1vLNs of wild-type larvae in LD cycles and in DD, with detectable protein at ZT1 or CT1, but not at ZT13 or CT13 [(FIG. 5A; Kaneko et al., *J. Neurosci.*, 17:6745–6760 (1997)]. PER proteins produced by $dbt^P$ larvae show three significant differences from wild-type (FIG. 5A). First, PER is detectable at ZT13 and CT13 in the 1vLNs of $dbt^P$ larvae. Second, the intensity of staining in the 1vLNs is stronger in $dbt^P$ than in wild-type larvae (samples shown were processed identically on the same day). Third, the pattern of expression in $dbt^P$ is widened to include regions of the brain not significantly stained in a wild-type background (seen most clearly in FIG. 5D). The elevated level of PER in $dbt^P$ was confirmed by Western blotting using extracts from dissected larval brains collected in LD (FIG. 5B). The latter results show that PER protein accumulation is dramatically increased by the $dbt^P$ mutation (compare $dbt^P$ to wild-type larvae, where PER is difficult to detect, FIG. 5B), and the high levels of accumulated PER protein do not show significant differences between ZT12 and ZT24 (FIG. 5B) in LD cycles in $dbt^P$. In addition, the electrophoretic mobility of PER proteins is relatively high and uniform in $dbt^P$ larvae, in contrast to the broad spectrum of lower PER protein mobilities observed in wild type larvae and adult heads (FIG. 5B). As the spectrum of protein mobilities in wild type Drosophila reflect PER protein phosphorylation [Edery et al., *Proc. Natl. Acad. Sci. USA*, 91:2260–2264 (1994)], the results suggest that PER is hypo-phosphorylated in $dbt^P$ mutants.

Figure 5C:
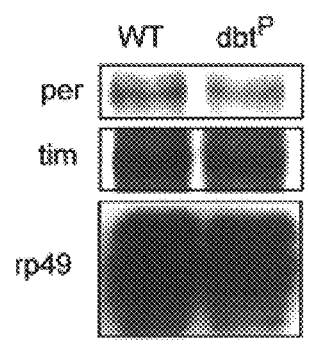

To determine whether the high levels of PER protein found by Western blotting of dissected $dbt^P$ larval brains reflected altered per RNA levels, RNase protection was used to detect per RNA in these tissues at ZT14–16 (time of expected peak per RNA accumulation in wild type Drosophila). The results in FIG. 5C show that per RNA is expressed at similar levels in wild-type and $dbt^P$ larval brains. Thus, the aberrant accumulation of PER proteins in $dbt^P$ mutants does not reflect increased per transcription or per RNA stability, but must be downstream of these events.

Figure 5D:
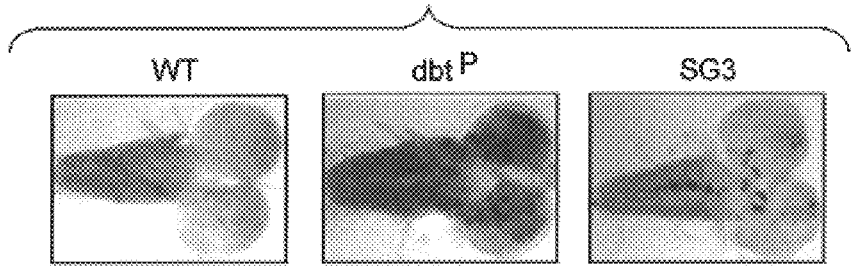

The pattern of PER expression in $dbt^P$ is similar to a PER-β-galactosidase fusion protein, PER-SG, expressed from the per promoter (FIG. 5D). In adults, per-SG RNA oscillates, but PER-SG protein does not. In fact, the PER-SG protein accumulates over progressive cycles, suggesting that it is a stable protein [Vosshall et al., *Science*, 263:1606–1609 (1994); Dembinska et al., *J. Biol.*, 12:157–172 (1997)]. PER-SG, detected with an antibody against β-galactosidase, is expressed in larvae in the 1vLNs and other cell clusters in the brain hemispheres, as well as cells adjacent and close to the ventral ganglion midline (FIG. 5D; Kanekoet al., *J. Neurosci.*, 17:6745–6760 (1997)]. The presence of the non-cycling PER-SG fusion protein therefore marks cells in which the per promoter is active, or has been active, during development. Comparable patterns were seen with two independently constructed SG lines [Kaneko et al., *J. Neurosci.*, 17:6745–6760 (1997)]. PER in wild type larvae has also been detected at very low levels in these cells [Kaneko et al., *J. Neurosci.*, 17:6745–6760 (1997)]. Thus, the pattern of staining of PERseen in $dbt^P$ reflects a normal spatial expression of per, but this pattern is only easily visible with a stable fusion protein or in a $dbt^P$ background.

Figure 5E:
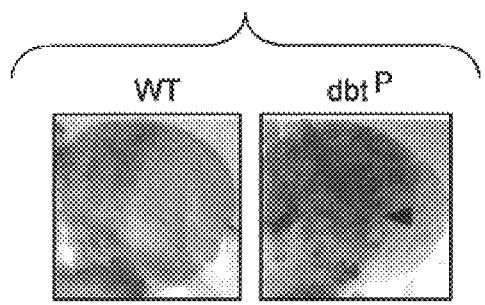

PER is Stable in $dbt^P$ Larvae in Constant Light: PER is detected at high levels in $dbt^P$ larval brains in DD as in LD (FIG. 5A). The persistence of PER proteins in 1vLNs in DD is presumably occurring in the presence of very low levels of the TIM protein which, as indicated above, fall below immunocytochemical detection in these cells in DD (FIG. 4A). In dbt+ larvae and adults, PER accumulation is suppressed in the absence of TIM [Vosshall et al., *Science*, 263:1606–1609 (1994); Price et al., *EMBO J.*, 14:4044–4049 (1995)]. It therefore seemed likely that PER in $dbt^P$ had become less dependent on TIM for its accumulation than in wild-type, especially since PER is detectable in brain cells where TIM is not detected in wild type or $dbt^P$ larvae (FIG. 4A, 5D) [Kaneko et al., *J. Neurosci.*, 17:6745–6760 (1997)]. This possibility would have been ideally tested using $tim^{01}$; $dbt^P$ larvae. However, it has not been possible to obtain third instar larvae from two different $tim^{01}$; $dbt^P$/TM6 lines. This may indicate a shift in the lethal phase of $dbt^P$ by the $tim^{01}$ mutation. An alternative to $tim^{01}$ was possible as constant light (LL) in a wild-type background produces a $tim^{01}$ phenocopy through light-dependent degradation of TIM [Hunter-Ensor et al., *Cell*, 84:677–685 (1996); Lee et al., *Science*, 271:1740–1744 (1996); Myers et al., *Scinece*, 271:1736–1740 (1996); Zeng et al., *Nature*, 380:129–135 (1996)]. FIG. 5E shows that in wild type larvae, PER accumulation is suppressed in response to LL as previously seen for adults. In contrast, in $dbt^P$ larvae raised in LL, PER continues to be strongly detected in the 1vLNs and the other PER-expressing cells (FIG. 5E). The persistence of PER in DD and LL indicates that PER proteins can accumulate in $dbt^P$ mutants even with very low levels of TIM.

Discussion

Doubletime Encodes a Central Clock Component: A new Drosophila clock gene, double-time, has been isolated by screening for circadian rhythm mutants. The short-period and long-period alleles alter behavioral rhythms and the timing of molecular oscillations of products of the two previously identified clock genes, per and tim. A third allele, $dbt^P$, is arrhythmic since it stops circadian oscillations of PER and TIM in third instar larvae. $dbt^P$ behaves as a strong hypomorph or null allele in complementation tests with $dbt^S$ and $dbt^P$. Since dbt mutations alter both behavior and clock gene cycling, it can be concluded that dbt encodes a central clock component as opposed to part of an output pathway.

The Role of dbt in the Clock: tim RNA and protein cycle in LD, and TIM remains cytoplasmic in $per^o$; $dbt^P$ indicating that at least some regulatory features of the Drosophila clock are unaffected in $dbt^P$ mutants. In contrast, PER is constitutively expressed at very high levels in LD and DD cycles, with increased levels also seen in new regions of the larval brain. These observations, and the finding that increased PER accumulation is not due to increased per RNA production, suggest that dbt affects circadian rhythmicity through PER protein. Altered patterns of tim RNA and TIM protein accumulation in $dbt^P$ are presumably secondary effects derived from the substantially increased accumulation of PER.

dbt Appears to Affect Stability of the PER Protein: The high levels of PER observed in $dbt^P$ are due either to: (i) increased per RNA translation; or (ii) increased PER stability. Altered patterns of PER degradation in $dbt^S$ and $dbt^L$ mutants could also reflect changes in either translational control or stability: PER in $dbt^S$ starts to accumulate 2 hours before wild type, but most PER disappears at least 6 hours before loss of the wild type protein (FIG. 3B). This is consistent with decreased stability of PER in $dbt^S$ mutants, although the possibility that in $dbt^S$, per RNA available at ZT20 is translated significantly less efficiently than at other times of day cannot be completely ruled out. In wild type flies, light degrades TIM which promotes elimination of PER. However, in $dbt^L$ mutants, PER remains for about 4 hours longer than in wild-type. Since these are times of day when little per RNA is present, the results suggest that the $dbt^L$ mutation reduces the rate of PER degradation. The low electrophoretic mobility observed for PER in $dbt^L$ mutants collected from ZT2 to ZT6 indicates hyperphosphorylation of the persistent PER proteins, which also suggests that these proteins were translated many hours earlier [Edery et al., Proc. Natl. Acad. Sci. USA, 91:2260–2264 (1994)]. The delayed degradation of PER in $dbt^L$ is not simply a consequence of lengthening the period of the rhythm, because in $per^L$ mutants, which have a period two hours longer than $dbt^L$ [Konopka and Benzer, Proc. Natl. Acad. Sci. USA, 68:2112–2116 (1971)], 'KMPER is degraded with kinetics more comparable to wild type [Rutila et al., Neuron, 17:921–929 (1996)]. It has been suggested that hyperphosphorylation of PER may signal nuclear degradation of this protein in wild type flies [Edery et al., Proc. Natl. Acad. Sci. USA, 91:2260–2264 (1994)]. Consistent with this proposal hyperphosphorylated forms of PER appear prematurely in $dbt^S$ mutants, and with a delay in $dbt^L$ mutants (FIG. 3C).

The electrophoretic mobility of PER in $dbt^P$ mutants differs significantly from wild-type: its migration in relation to PER proteins formed in wild type larval brains and in adult heads suggests that it is constitutively hypo-phosphorylated (FIG. 5B). Since a substantial portion of the PER accumulating in $dbt^P$ larval brains is derived from non-clock cells, the possibility that PER is more highly phosphorylated in 1vLNs cannot be ruled out, but slower-migrating PER proteins have never been observed in $dbt^P$ mutants despite high protein levels. dbt mutants appear to affect PER stability and circadian rhythmicity by altering PER phosphorylation. This is also consistent with the results of dbt sequence analysis, which has shown that the DBT protein is very closely related to human casein kinase Iε (Example 2, below). Therefore, the most likely role for DBT in the Drosophila clock is as a mediator of post-translational modification that determines PER stability.

PER in $dbt^P$ behaves much like the PER-β-galactosidase fusion protein, PER-SG, in wild type flies. PER-SG is expressed widely in the larval brain, and is detectable at high levels in adults even in the absence of TIM [Vosshall et al., Neuron J., 263:345–360 (1994)] as well as in constant light in adults and larvae. In adults, per-SG RNA cycles, but the protein does not, indicating that PER-SG is either more stable than PER or its translation is much more efficient. Adding an additional 231 amino acids of PER to PER-SG to make the fusion protein PER-BG results in cycling of this larger fusion protein [Dembinska et al., J. Biol. Rhythms, 12:157–172 (1997)]. Since cycling was correlated with a change in protein structure, it was suggested that the SG-BG region confers protein instability [Dembinska. et al.,J. Biol. Rhythms, 12:157–172 (1997)]. PER-SG is not phosphorylated in a circadian ranner, whereas PER-BG is, [Dembinska. et al., J. Biol. Rhythms, 12:157–172 (1997)] showing that a defined segment of PER may be involved in both phosphorylation and stability, and that a possible link exists between the two events. The parallels between PER in $dbt^P$ larvae and PER-SG are very striking. Neither protein cycles, both accumulate to high levels with a similar expression pattern in larvae, and phosphorylation is affected for both proteins. If the 231 amino acid difference between PER-SG and PER-BG indeed confers instability, one interpretation of our data is that DBT works through this region of PER.

Determination of where DBT Acts in the Cell: In $tim^{01}$ mutants, which block PER nuclear translocation, PER is unstable [Vosshall et al., Science, 263:1606–1609 (1994); Price et al., EMBO J., 14:4044–4049 (1995)], indicating the presence of a cytoplasmic activity that destabilizes PER monomers. In wild type adults, constant light suppresses TIM, which subsequently results in very low levels of PER [Price et al., EMBO J., 14:4044–4049 (1995)], and the same result is seen in wild-type third instar larvae raised in constant light (FIG. 5E). However, in $dbt^P$ mutants, similar high levels of PER accumulate in LD, DD and LL. Since the $dbt^P$ allele allows comparable PER accumulation with either high or low levels of TIM, we conclude that $dbt^P$ allows TIM-independent PER accumulation, and that DBT is a component of the cytoplasmic activity that destabilizes PER monomers in wild type and $tim^{01}$ flies. Consistent with this conclusion, predominantly cytoplasmic accumulation for the expanded PER pattern in $dbt^P$ larval brains was observed. tim does not appear to be expressed in this expanded pattern in wild type larvae [Kaneko et al., J. Neurosci., 17:6745–6760 (1997)], so expanded accumulation of PER monomers in $dbt^P$, but not wild type, larval brains indicates novel cytoplasmic stability for PER in the mutant.

There is also evidence that DBT influences stability of nuclear PER proteins. PER is detected immunocytochemically in nuclei of $dbt^S$ and $dbt^L$ 1vLNs prior to its disappearance, suggesting that the differing kinetics of PER degradation in wild type, $dbt^S$ and $dbt^L$, reflect different rates of PER elimination from the nucleus. Increased nuclear stability of PER monomers is also apparent from our analyses of $dbt^P$ 1vLNs: PER is lost from wild type, but persists in $dbt^P$ nuclei after exposure to light has removed most TIM proteins (FIGS. 5A and 5E). Thus, dbt may affect the stability of both cytoplasmic and nuclear PER monomers. This does not mean that DBT must function in both subcellular compartments, since a post-translational modification generated in the cytoplasm could have delayed effects in the nucleus.

A Basis for Light-Driven Molecular Cycles in $dbt^P$ Mutants: If PER is constitutively expressed in the nuclei of 1vLNs in $dbt^P$, why are tim RNA oscillations seen in LD cycles, but not in DD? Prior work has indicated that suppression of per and tim RNA levels requires activity of a PER/TIM complex (reviewed in [Rosbash et al., Harb. Symp. Quant. Biol. J., 61:265–278 (1996); Young et al., Harb. Symp. Quant. Biol., 61:279–284 (1996)]. Because light eliminates TIM proteins, LD cycles will periodically eliminate PER/TIM complexes, but generate a large pool of long-lived, monomeric PER proteins in $dbt^P$ mutants. The latter proteins are predicted to have little or no influence on per and tim transcription. One interpretation of the present results is that in DD, $dbt^P$ mutants produce a low level of tim transcription that is maintained by constitutive formation, nuclear translocation, and nuclear activity of PER/TIM complexes. In wild type Drosophila, PER's cytoplasmic instability allows high levels of per and tim RNA to accumulate prior to formation of PER/TIM complexes, promoting oscillations of RNA and protein accumulation. Stable accumulation of PER monomers in $dbt^P$ mutants should allow an equilibrium to be established in DD in which constitutive transfer of PER/TIM complexes to nuclei produces two effects: (i) low levels of RNA expression and (ii) a sizeable pool of PER monomers that are evidently much more stable than TIM (FIGS. 4A and 5A). Although, neither tint RNA nor protein were detected in $dbt^P$ in DD immunocytochemically, this probably reflects how even a very low level of TIM (which is stable in the absence of light) is sufficient to maintain continuous nuclear entry of PER/TIM complexes when PER proteins are stabilized (further evidence is discussed below). An important difference between wild-type and $dbt^P$ Drosophila is that most PER monomers are degraded with only a small fraction of the proteins escaping to form PER/TIM complexes in wild type flies, whereas stable PER proteins in $dbt^P$ mutants now bind TIM without temporal constraints. This interpretation is summarized in FIG. 6.

In constant light, PER translocation to the nucleus is seen in the 1vLNs, but this probably reflects that light is less effective at removing TIM than the $tim^{01}$ mutation, and that increased tim transcription during the period of lights-on can offset some light-induced TIM depletion (FIG. 4B). The results also indicate that a very low level of residual TIM protein can translocate highly stabilized PER to the nucleus. A precedent for nuclear translocation of PER in constant light exists with the PER-β-gal fusion protein, PER-SG, which is stable cytoplasmically in $tim^0$, but can be found in the nucleus in $tim^+$ LNs and photoreceptors in constant light.

Example 2
THE DROSOPHILA CLOCK GENE DOUBLE-TIME ENCODES A PROTEIN CLOSELY RELATED TO HUMAN CASEIN KINASE Iε

Introduction

In Example 1, above, the isolation of mutant alleles of a new clock gene, double-time (dbt) was described. Two of these mutations either shorten ($dbt^S$) or lengthen ($dbt^L$) the period of the behavioral rhythm, and each mutation has period-altering effects on molecular oscillations of PER and TIM that are correlated with the mutant behavioral rhythms. A third, P-element-induced mutation ($dbt^P$), is associated with pupal lethality, but blocks circadian molecular rhythms of per and tim gene products in pacemaker cells of the larval brain. Therefore dbt is an essential component of the Drosophila clock [Example 1, above]. In both short- and long-period dbt mutants, the kinetics of PER protein phosphorylation and degradation are altered, and $dbt^P$ mutants constitutively produce unusually high levels of a hypophosphorylated PER protein. In contrast to wild type larvae, PER protein accumulation in $dbt^P$ larvae is not dependent on accumulation of TIM. All of these observations suggested that DBT regulates circadian rhythmicity through effects on stability of monomeric PER proteins [Example 1, above] The finding that both PER phosphorylation and stability are simultaneously affected in all three dbt alleles suggests that dbt might alter PER stability through effects on phosphorylation.

In this example, both the clock and lethal phenotypes of $dbt^P$ are shown to be capable of being reverted by excision of the associated P-element, and that the affected gene encodes a protein closely related to human casein kinase Iε. $dbt^P$ suppresses transcription of the locus, and transcription is restored following P-element excision. $dbt^S$ and $dbt^L$ are caused by single amino acid substitutions in highly conserved residues of the predicted kinase domain of the protein. dbt is expressed in the same regions of the adult Drosophila brain as per and tim, but, in contrast to per and tim, dbt RNA levels do not appear to oscillate. DBT protein is shown to interact with PER both in vitro and in Drosophila cells. These studies establish dbt as the first vital gene to be associated with circadian rhythmicity in any organism, and indicate a role for the predicted kinase in phosphorylation and regulated accumulation of PER in wild type flies.

Experimental Procedures

Genomic and cDNA Library Screening: Drosophila genormic library in Lambda FIX II vector is from Stratagene. Directionally cloned Drosophila adult head cDNA library has been described previously [Hamilton et al., NAR, 19:1951–1952 (1991); Palazzolo et al., Gene, 88:25–36 (1990)]. Directionally cloned Drosophila embryonic and pupal cDNA libraries were prepared using the ZAP cDNA synthesis kit and the Uni-ZAP XR cloning kit (both from Stratagene) and were generously provided by Simon Kidd. Molecular techniques were performed using standard protocols [Ausubel et al., in Current Protocols in Molecular Biology, edited by K. Janssen: John Wiley & Sons, Inc. (1995); and Sambrook et al., Molecular Cloning: A Laboratory Manual: Cold Spring Harbor Laboratory Press. (1989)].

Genomic DNA flanking the P element insertion site was isolated by plasmid rescue [Pirrotta, In Drosophila: A Practical Approach, edited by D. B. Roberts. (Oxford: IRL Press Limited) 1986)]. DNA fragments to be used as template for probe preparation were purified using QlAquick gel extraction kit (Qiagen). $^{32}P$ labeled probes were prepared by random prining of gel purified DNA fragments using a 10× hexanucleotide mix (Boehringer Mannheim) according to the manufacturer's recommendations. Hybridizations were performed in 50% formamide, 6×SSPE, 5× Denhardt's, 1% SDS and 0.1 mg/ml salmon sperm DNA at 42° C. for at least 16 hours. Membranes were washed twice in 2×SSC/0.1% SDS at room temperature and twice in 0.2×SSC/0.1% SDS at 65° C. before being exposed to film at −80° C. with an intensifying screen.

Southern Hybridization: Isolation of genomic DNA from adult flies was performed as described [Jowett, In Drosophila: *A Practical Approach*, edited by D. B. Roberts. (Oxford: IRL Press Limited), (1986)]. $^{32}$P labeled probes were prepared by random priming as described above. Hybridizations were perfomed for at least 16 hours at 42° C. in 20 ml hybridization buffer (50% formamide, 2×SSPE, 1% SDS, 0.5× Denhardt's, 10% w/v dextran sulphate and 0.5 mg/ml salmon sperm DNA). Probes were removed by two washes in boiling 0.1×SSC/0.5% SDS and the stripped membranes were exposed to film to confirm that the hybridized probe had been completely removed before re-probing.

RNA Isolation and Analysis: Total RNA from pupae, adult heads or adult bodies was isolated using RNAzol B (Tel-Test). Poly A+ mRNA was isolated using the Oligotex mRNA isolation kit (Qiagen). For Northern analysis, RNA was separated by denaturing agarose gel electrophoresis and transferred to membranes as described [Fourney et al., *Focus*, 10:5–7 (1988)]. $^{32}$P labeled probes were prepared as described above. Hybridizations were carried out for at least 16 hours at 42° C. in 20 ml hybridization buffer (50% formamide, 2×SSPE, 1% SDS, 2× Denhardt's, 10% w/v dextran sulphate and 0.5 mg/ml salmon sperm DNA). Probes were removed as described above.

Ribonuclease (RNAse) protection analysis was performed using 20 mg total RNA from each time point. Ther per [Sehgal et al., *Science*, 263:1603–1606 (1994)], tim and tubulin [Sehgal et al., *Sciencie*, 270:808–810 (1995)] ribroprobes have been described previously. The dbt riboprobe template was prepared by subcloning a fragment from the dbt cDNA corresponding to nucleotides 1583–2090 into pBSIISK- (Stratagene). This was linearized with EarI and transcribed with T3 RNA polymerase to generate an antisense riboprobe 294 nucleotides in length and which produces a protected fragment of 270 nucleotides. Hybridizations and RNAse digestions were performed using the RPA II kit (Ambion), according to the manufacturer's recommendations. Protected fragments were separated on 5% acrylamide/8M Urea gels and visualized by autoradiography. Quantitation of protected fragments was performed with a Molecular Dynamics phosphorimager, with levels of per, tim and dbt mRNA normalized to tubulin at each time point.

DNA Sequencing: Genomic DNA from dbt$^S$, dbt$^L$ and the cn bw parental line used for mutagenesis (see Example 1, above) was isolated as described above. Genomic DNA from each line was used as template for PCR amplification of the dbt gene with AmpliTaq DNA Polymerase (Perkin Elmer). An aliquot of each reaction was used as template for re-amplification. PCR products were separated by agarose gel electrophoresis and purified as described above. 100–200 ng of each gel purified PCR product was used as template for sequencing with the AmpliCycle Sequencing Kit (Perkin Elmer) according to the manufacturer's recommendations. Complete sequencing of cDNA and genomic clones was performed using the AmpliCycle Sequencing Kit, or by the Taq FS dye terminator cycle sequencing method using a Perkin Elmer/Applied Biosystems Model 377 DNA Sequencer (Protein/DNA Technology Center, Rockefeller University).

In Situ Hybridization to Adult Head Sections: 12 mm frozen sections of adult Drosophila heads were cut as in Amrein and Axel [Amrein and Axel, *Cell* 88: 459–69 (1997)]. In situ hybridization was performed as described in Schaeren-Wiemers and Gerfin-Moser [Schaeren-Wiemers and Gerfin-Moser, *Histochemistry*, 100:431–40 (1993)] except that per and tim antisense DIG RNA probes derived from full-length cDNAs were hydrolyzed prior to use, and all the hybridization and washes were performed at 55° C. The dbt probe was the same as used in RNAse protection experiments.

Protein Interaction Studies: GST fusion proteins were constructed and expressed as described [Saez and Young, *Neuron*, 17:911–920 (1996)]. In vitro translation of DBT proteins, and interaction studies with GST-PER fusion proteins in vitro and GFP-DBT fusion proteins in S2 cultured Drosophila cells were performed as described [Saez and Young, *Neuron*, 17:911–920 (1996)].

Results

Analysis of the Region Surrounding the dbt$^P$ Insertion Site: As described in greater detail in Example 1, above, short and long period alleles of a novel circadian rhythm gene, double-time (dbt$^S$ and dbt$^L$, respectively) have been isolated from a genetic screen for locomotor rhythm mutations. A chromosome deficiency, Df(3R)tll-g, and a P-element-induced mutation (dbt$^P$), both of which fail to complement the dbt$^S$ and db$^L$ mutations, have been identified as well. Given the similar behavioral phenotype of Df(3R)tll-g/dbt$^S$ and dbt$^P$/dbt$^S$ flies [Example 1, above], dbt$^P$ is most likely a null or strong hypomorphic allele. As dbt$^P$ failed to complement the Df(3R)tll-g, dbt$^S$ and dbt$^L$ mutations [Example 1, above], it provided a basis for molecular cloning of the dbtlocus.

Figure 7:
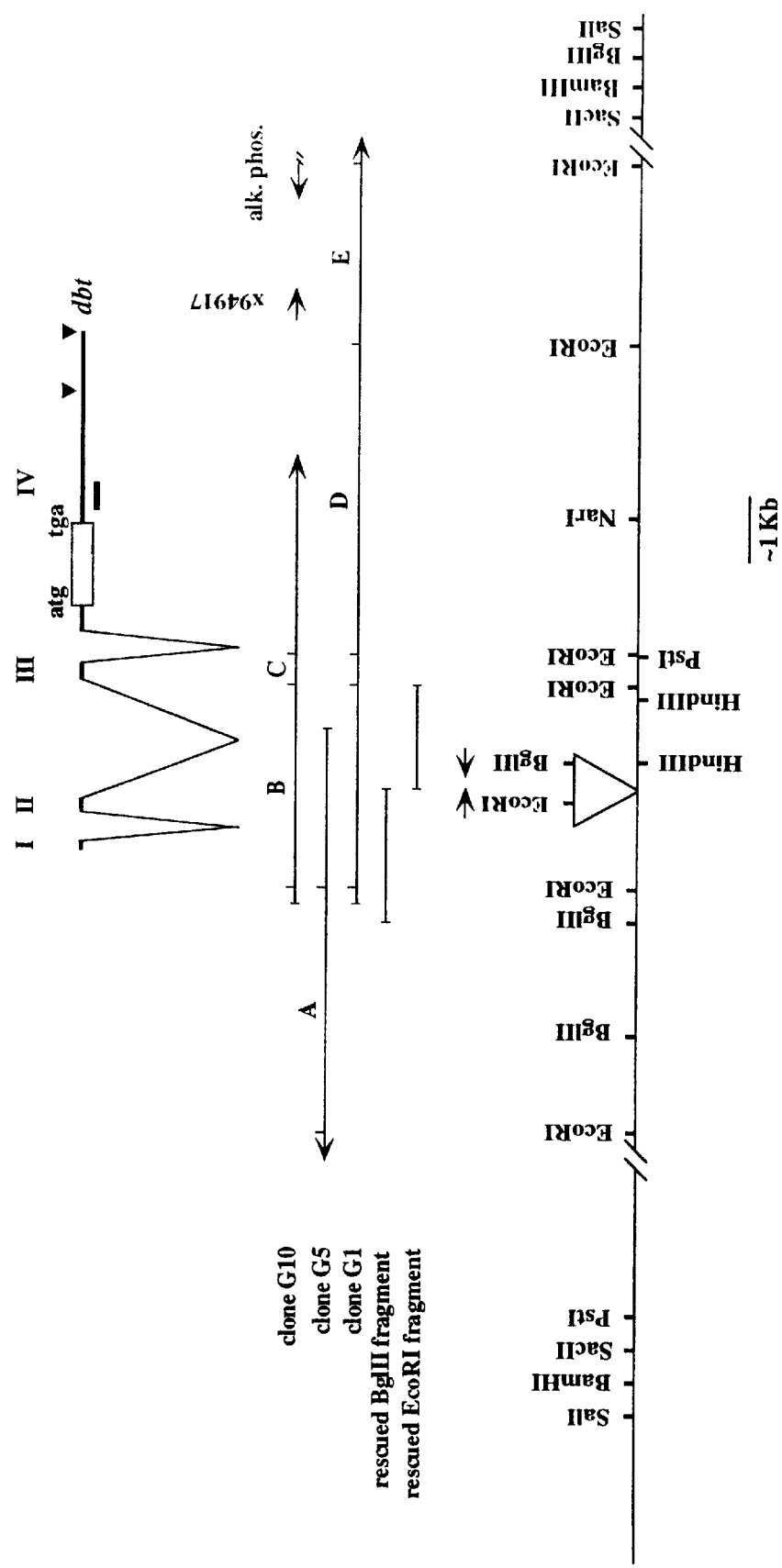
FIG. 7 shows a map of the region surrounding the P element insertion site of dbt$^P$. The map was created following Southern hybridization of genomic DNA isolated from dbt$^P$ and dbt$^{Pex}$ lines, as well as analysis of restriction digests of the genomic DNA clones. Restriction sites far to the right or left of the P element insertion were identified, but were not resolved well enough to accurately determine their distance from the the P element. Regions of genomic DNA recovered by plasmid rescue are indicated. The relative sizes and orientations of genomic clones 1, 5 and 10 are shown. Arrows on the ends of genomic clones indicate that those ends were not precisely defined. A–E, fragments resulting from EcoRI digestion of the three genomic DNA clones. Positions and orientations of a 1.9 kb alkaline phosphatase gene (accession number X98402), and a previously described 0.9 kb transcript of unknown function (accession number X94917) are indicated (see text in Example 2). The dbt transcription unit is comprised of four exons with the open reading frame (shaded rectangle) residing entirely within exon IV. The P element insertion is within the intron separating exons II and III. The black bar beneath the dbt transcript indicates the location of the fragment used to synthesize antisense riboprobes for RNAse protection analysis and in situ hybridization. Filled triangles identify to the locations of two potential polyadenylation signals (see text in Example 2).

Genomic DNA fragments flanking the P element insertion site were obtained by plasmid rescue [Pirrotta, In Drosophila: *A Practical Approach*, edited by D. B. Roberts. (Oxford: IRL Press Limited) (1986)], and these fragments (rescued BglII- and EcoRI fragments, FIG. 7) were then used as probes to screen a Drosophila genomic DNA library. Three genomic DNA fragments (clones G1, G5 and G10, FIG. 1), each between 8 and 12 kilobases (kb) in length, were recovered and mapped by restriction analysis. FIG. 7 shows a restriction map of the region surrounding the P element insertion site. Five smaller genomic DNA fragments, resulting from EcoRI digestion of the genomic clones, were isolated and subcloned (fragments A–E, FIG. 1). Together, these five non-overlapping fragments represent approximately 16 kb of genomic DNA surrounding the P element insertion site.

Since P elements tend to insert near the transcription start site of the affected gene [Kelley et al., *Mol. and Cell Bio.*, 7:1545–1548 (1987); Spradling et al., *PNAS, USA*, 92:10824–10830 (1995)], it was predicted that the P element insertion site would be close to the transcribed region of the dbt gene. To determine the number of transcription units in the cloned genomic region, the five EcoRI fragments were used as probes for Northern analysis of poly A+ RNA isolated from heads and bodies of wild type flies. While no transcribed regions within EcoRI fragments A or B were detected, three transcripts, approximately 1.1, 2.05 and 3.2 kb in length, were detected by this method with probes corresponding to fragments D and E.

Since all of the transcribed regions surrounding the P element insertion site appeared to include sequences located within EcoRI fragments D and E, these two genomic DNA fragments were selected as probes to screen Drosophila embryonic, pupal, and adult head cDNA libraries. In addition, genomic sequence from both ends of each of the EcoRI fragments was obtained. Conceptual translation of these genomic sequences revealed the presence of a gene encoding a previously described alkaline phosphatase [GenBank accession NO: X98402] within EcoRI fragment E (FIG. 7). The complete cDNA for the alkaline phosphatase gene is 1867 nucleotides in length [GenBank accession NO:X98402] and presumably corresponds to the 2.05 kb transcript observed by Northern analysis. The P-element insertion site maps ~9 kb downstream of this gene. Three cDNA clones were isolated from the embryonic library, and partial sequencing of these cDNAs revealed that all were part of the same transcript. Following a search of DNA and protein sequence databases [Altschul et al., *J. Mol. Biol.* 215: 403–410 (1990)], it was determined that this gene had been previously isolated as part of a GAL4 enhancer trap screen. The complete cDNA is 907 bp in length and presumably corresponds to the 1.1 kb transcript detected by Northern analysis. Comparison of this cDNA sequence to genomic sequence obtained from EcoRI fragment E demonstrated that this gene is located ~7 kb downstream of the P element insertion in $dbt^P$ (FIG. 1, transcript x94917).

The pupal and head cDNA libraries yielded a total of eight cDNA clones. Partial sequencing of each cDNA revealed that all were derived from the same transcript and demonstrated that the 3' end of this gene spanned the EcoRI site separating the D and E fragments used as probes (FIG. 7). These cDNAs also included 5' sequences from EcoRI fragment C, and fragment B, which contains the P-element insertion site. This gene was likely to correspond to dbt, and (as shown below), to encode the 3.2 kb transcript found by Northern analysis.

Figure 8:
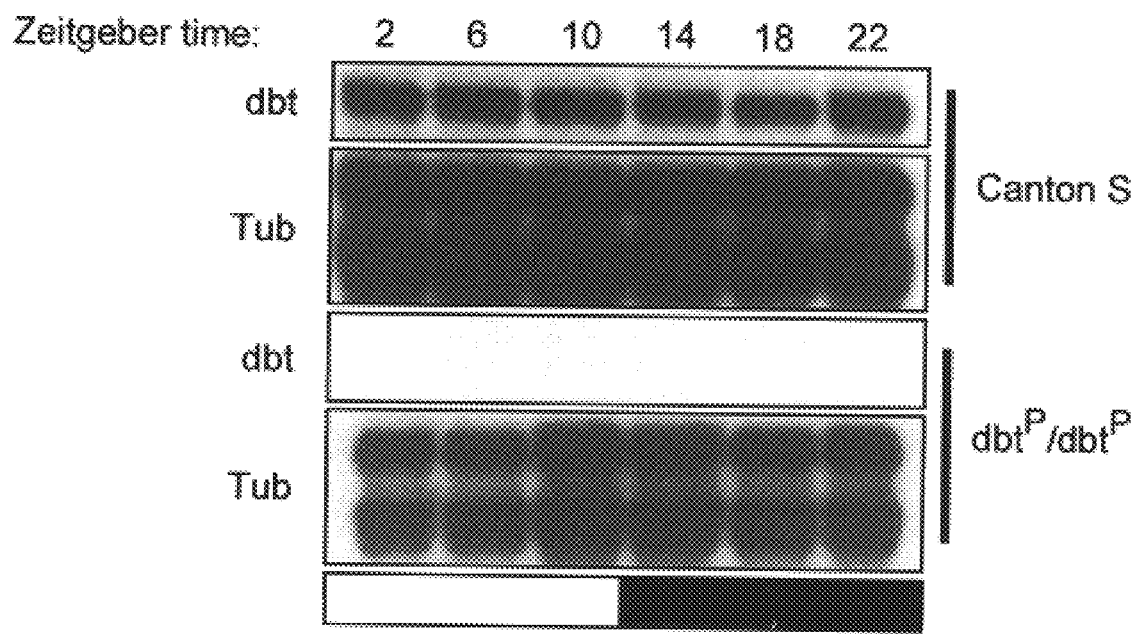
FIG. 8 shows the mRNA levels of the candidate dbt gene are significantly reduced in homozygous P element containing lines. Canton S and dbt$^P$/TM6Tb flies were transferred to fresh bottles and allowed to lay for 1–2 days. Adult flies were removed and bottles were placed in incubators to entrain developing flies to LD12:12. As Drosophila began to pupate, wild type, or Tb$^+$ (dbt$^P$ homozygous) pupae were collected at four hour intervals for one day. Total RNA was isolated from whole pupae of each genotype at each time point, and candidate dbt mRNA detected by RNAse protection analysis using a $^{32}$P labeled antisense riboprobe (see FIG. 7). Protected fragments were resolved by denaturing polyacrylamide gel electrophoresis and visualized by autoradiography. While the dbt transcript is readily detected at each time point in Canton S pupae, it is barely detected in dbt$^P$ homozygous pupae. Tubulin served as an internal control to confirm that intact total RNA had been isolated and quantitation of dbt mRNA levels was normalized to tubulin mRNA levels at each time point.

Molecular and Behavioral Analyses of $dbt^P$ and its Revertants: Because mid- to late stage $dbt^P$ pupae do not survive, $dbt^P$ homozygotes were recovered as viable early pupae from balanced $dbt^P$/TM6, Tubby stocks as previously described [Example 1, above]. In order to measure the relative levels of the candidate RNA in mutant and wild type pupae, $dbt^P$ and wild type pupae were collected at four hour intervals over one day of LD, and total RNA prepared for each time point. The cDNA sequence (described below) was used to generate an antisense riboprobe for RNAse protection studies. A protected fragment of the expected size was detected in total RNA isolated from wild type pupae at all timepoints, but the same protected fragment is detected at no more than 10–20% of the wild type level in the $dbt^P$ samples (FIG. 8). A similar result was obtained on comparing RNA from mutant and wild type third instar larvae. Thus, the P-element strongly reduces the level of the candidate RNA, but not control RNA species (FIG. 8), further indicating an association between the dbt mutant phenotypes and changes in this transcription unit.

Figure 9A:
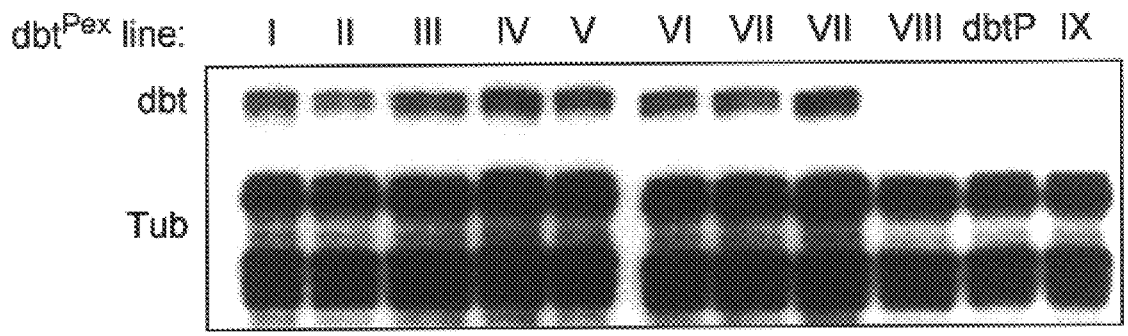
FIGS. 9A–9B show the loss of the P element restores expression of the dbt gene.
Figure 9B:
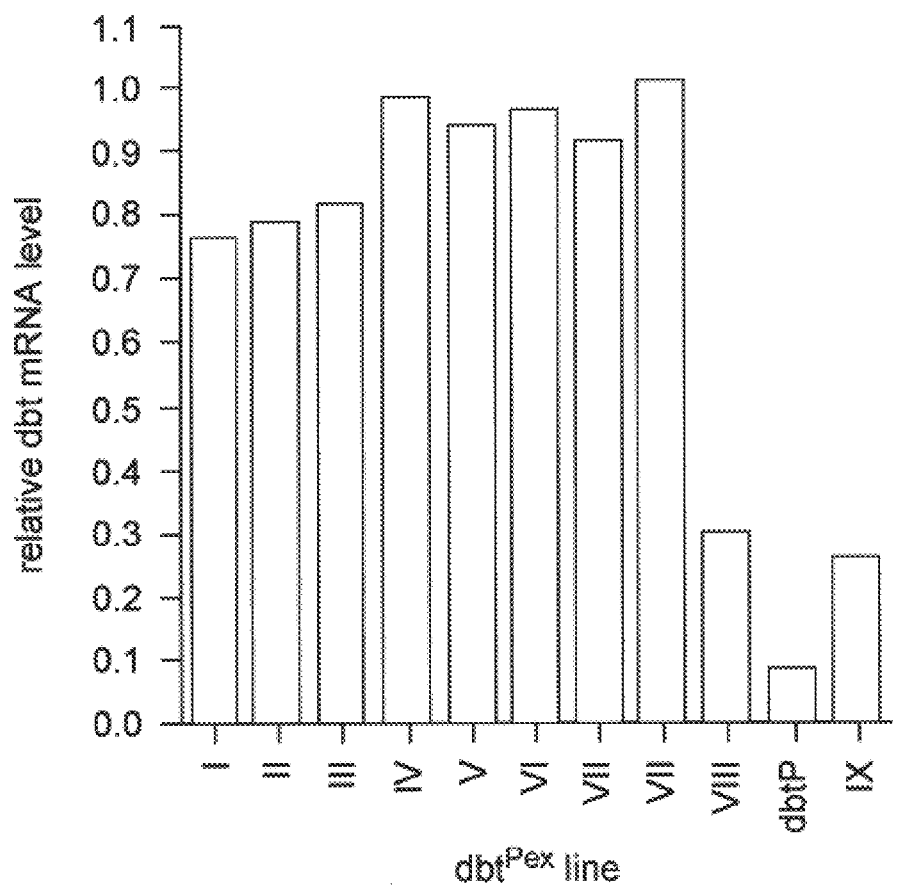

Several revertant lines were produced and subsequently examined, to determine if viability, normal locomotor rhythms, and putative dbt RNA expression were restored in lines from which the P-element had been excised. Seven of nine P-element revertants produced were viable as homozygotes and showed normal locomotor activity rhythms. Two lines failed to fully revert the rhythm phenotype, and one of these also did not revert lethality (VIII and IX, Table 4). To determine whether the collection of revertants restored normal levels of the candidate dbt mRNA as well, RNA was derived from homozygous, $dbt^P$ revertant pupae as described above. Since no oscillation in the putative dbt transcript was previously observed in $dbt^P$ pupae (FIG. 8), pupae were not first entrained to a light:dark cycle prior to collection. The seven revertants that restored both viability and rhythmicity expressed approximately 8–10 times as much of the putative dbt RNA as the parental $dbt^P$ mutant line (FIG. 9), confirming that the P element insertion disrupts the normal expression of the candidate dbt gene. The two lines showing incomplete reversion of the dbt phenotypes continued to produce low to intermediate levels of the putative dbt RNA (FIG. 9). Molecular studies to be presented elsewhere indicate that the incomplete revertants VIII and IX have obtained additional sequence changes affecting this transcription unit in conjunction with the P-element excision. Together the revertant data strongly indicate that the P-element is the cause of both pupal lethality and aberrant circadian rhythmicty, and that the affected transcript is a product of the dbt locus.

TABLE 4

| $dbt^{Pex}$-Line | $dbt^{Pex}/dbt^-$ | | $dbt^{Pex}/dbt^S$ | |
|---|---|---|---|---|
| | tau ± SEM | (#AR/n) | tau ± SEM | (#AR/n) |
| I | 24.2 ± 0.2 | (2/8) | 22.1 ± 0.1 | (0/5) |
| II | 24.01 ± 0.1 | (0/10) | 22.0 ± 0.0 | (0/5) |
| III | 24.1 ± 0.2 | (3/8) | 22.0 ± 0.4 | (1/5) |
| IV | 23.8 ± 0.2 | (5/13) | 21.7 ± 0.2 | (1/9) |
| V | 23.7 ± 0.3 | (0/5) | 21.8 ± 0.2 | (0/5) |
| VI | 24.5 ± 0.5 | (6/8) | 21.9 ± 0.1 | (0/5) |
| VII | 23.8 ± 0.6 | (417) | 29.1 ± 0.1 | (0/5) |
| VIII | L | | 19.0 ± 0.1 | (2/12) |
| $dbt^P$ | L | | 19.0 ± 0.1 | (0/18) |
| IX | 26.5 ± 0.3 | (17/27) | 20.5 ± 0.1 | (3/24) |

Loss of the P element restores viability and reverts the behavioral phenotype of $dbt^P$. Excision of lines ($dbt^{Pex}$), in which the third chromosome was generated from $dbt^P$ by apparent excision of the P element (loss of orange eye color), were crossed to a dbt line (the original $dbt^P$ of Df(3R) tll-g), and to $dbt^S$. The average periods (tau) of locomotor activity in the transheterozygous progeny were assayed in DD. #AR/n, number of arrhythmic flies/total number assayed; L, a lethal genotype; $dbt^P$, a line which resulted from the same series of genetic crosses as the others, but in which the orange eye color was not lost.

Figure 10:
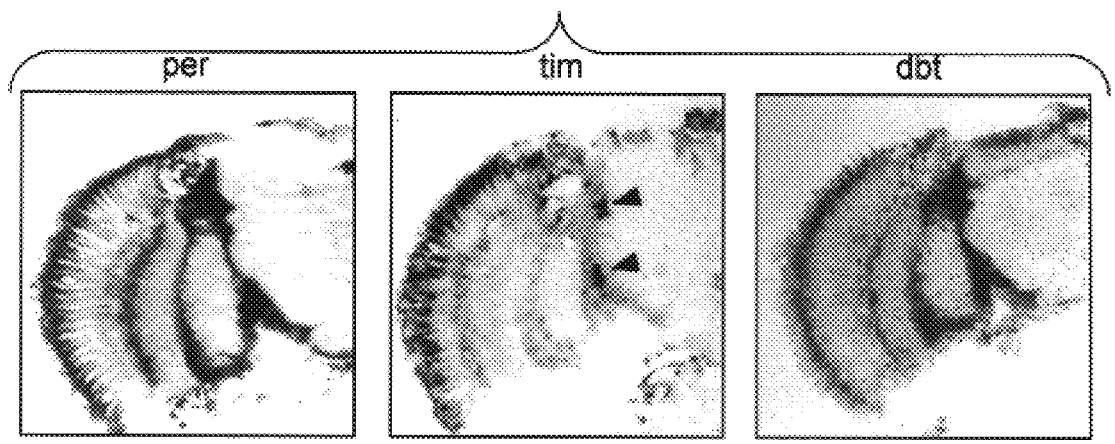
FIG. 10 shows that per, tim and dbt mRNAs are co-localized in adult heads. In situ hybridization of antisense digoxigenin RNA probes for per, tim and dbt to sections of Canton S adult heads at ZT12. Only half of each head section is shown. Expression of all three transcripts is detected in the photoreceptor cells. per and dbt transcripts are expressed in a broad region between the optic lobes and central brain, whereas tim is expressed discretely in lateral neuron pacemaker cells (indicated by arrowheads).

In situ Hybridization Analysis of dbt mRNA: In order to test whether dbt is expressed in clock cells in the brain, in situ hybridizations to adult head sections with per, tim and dbt antisense RNAs were performed. The results in FIG. 10 indicate that all three genes are expressed in photoreceptor cells composing the eyes. tim shows a discrete pattern in brain, and is expressed at highest levels in the lateral neurons [LNs; Ewer et al., *J. Neurosci.*, 12:3321–3349 (1992); Frisch et al., *Neuron*, 12:555–570 (1994) and Vosshall and Young, *Neuron*, 15:345–360 (1995)]. per and dbt are expressed in a wider region between the optic lobe and the central brain, which includes the LNs. The pattern of per RNA expression seen here is identical to the anti-β-galactosidase staining previously seen in a per promoter b-galactosidase transgenic line [Vosshall and Young, *Neuron*, 15:345–360 (1995)], and the pattern of tim staining is the same as that observed with anti-TIM antibody [Myers et al., *Science*, 271:1736–1740 (1996)]. Therefore, per and dbt appear to be expressed in the same cells in the brain, which include the tim-expressing cells. Interestingly, the RNA signals for all three genes are located predominantly at the periphery of the nucleus in the photoreceptors, although the significance of this is not yet clear.

Sequence Analysis of dbt and the $dbt^S$ and $dbt^L$ Mutations: Each of the eight putative dbt cDNA clones was completely sequenced. The most complete of these (~3.0 kb, clone P12) contained an open reading frame of 1320 bp flanked by 5' and 3' untranslated sequences. In vitro transcription and translation of P12 demonstrated that this clone encodes a protein of ~46 kDa, as determined by SDS-PAGE (discussed further below). The sequence of the P12 open reading predicts a 440 aa protein with a molecular mass of 48 kDa. Oligonucleotide primers flanking the predicted open reading frame were synthesized and used for PCR amplification of the dbt gene from genomic DNA isolated from the $dbt^S$ and $dbt^L$ mutant lines, as well as from the parental line used for chemical mutagenesis. Comparison of genomic DNA sequence obtained from each line revealed a single nucleotide change from the corresponding parental DNA for each mutant, providing perhaps the strongest evidence that the gene isolated is dbt. Each point mutation results in an amino acid change with $Pro^{47} \rightarrow Ser$ in $dbt^S$ flies and $Met^{80} \rightarrow Ile$ in $dbt^L$ (FIG. 11).

BLAST [Altschul et al., *J. Mol. Biol.* 215:403–410 (1990)] searches conducted with the dbt DNA sequence revealed that DBT is closely related to a family of previously identified protein kinases. The most closely related kinase is the epsilon isoform of human casein kinase I [Fish et al., *Journ.BiolChem*, 270:14875–14883 (1995)]. dbt is 75% (719/947) identical at the nucleotide level and 86% (260/301) identical at the amino acid level to the kinase domain of human casein kinase I$\epsilon$, suggesting that DBT is a structual homologue of this enzyme. FIG. 11 shows an alignment of the amino acid sequences of casein kinase I family members from diverse species. Because the DBT amino acid sequence identity with casein kinase I family members begins at the initiator methionine, and the sequence surrounding the predicted AUG start codon precisely matches the consensus sequence for a Drosophila translation start site [Cavener, *NAR*, 15:1353–1361 (1987)], it is believed that the Met$^1$ in FIG. 11 is the authentic translation initiation site. Note that the amino acid changes in the dbt$^S$ and dbt$^L$ mutants occur at positions which are highly conserved between organisms. Although no specific function has been attributed to these regions [Hanks et al., *Science* 241: 42–54 (1988)], they are probably required for normal DBT function.

The nucleotide sequences of all eight cDNAs, were compared to the wild type sequence of the genomic region surrounding the P element insertion site. Alignment of the cDNA and genomic sequences demonstrates that the dbt transcript is encoded by four exons and that the predicted open reading frame resides within a single exon (FIG. 7). Two potential polyadenylation signals have been identified, which could produce transcripts of approximately 3.2 and 4.0 kb. Most of the cDNAs terminate after the first putative poly A addition signal. The P element insertion is located within the intron separating exons II and III (FIG. 7), providing further support for identification of the gene as dbt.

Figure 12A:
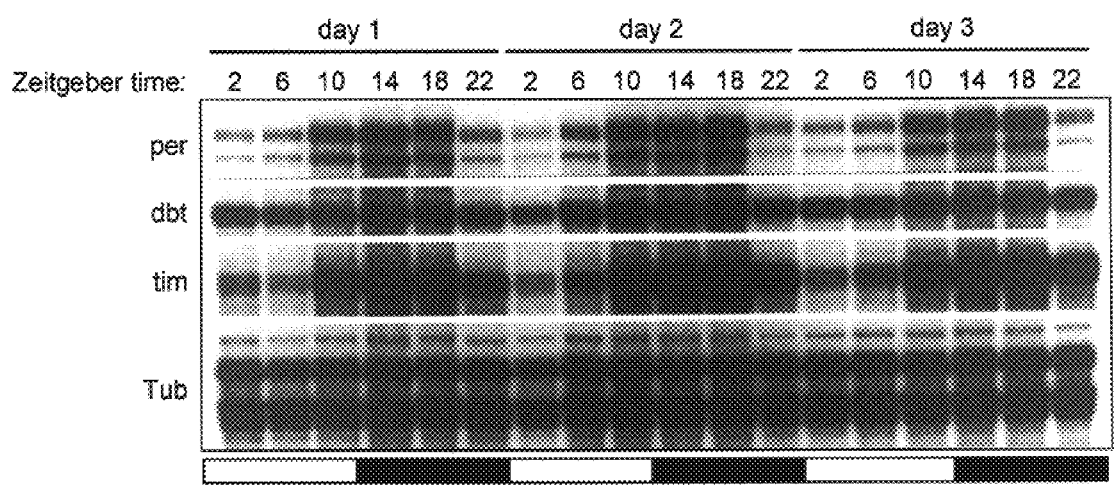
FIGS. 12A–12B show that the levels of the dbt transcript in adult heads do not appear to oscillate.
Figure 12B:
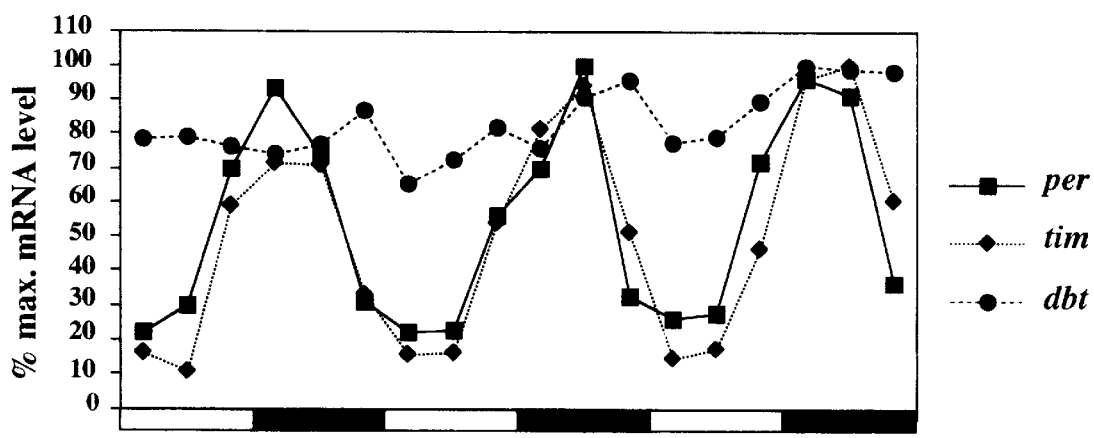

Analysis of dbt RNA levels in Wild type Flies at Different Times of Day: Because mRNA levels of the two previously identified Drosophila clock genes, per and tim, have been shown to oscillate with a 24 hour period in heads of adult wild type flies [Hardin et al., *Nature*, 343:536–540 (1990) and Sehgal et al., *Science*, 270:808–810 (1995)], it was of interest to determine whether levels of dbt mRNA oscillate as well. Although analysis of wild type pupae had already suggested that the abundance of dbt RNA remains essentially constant throughout the day and night, these measurements represent RNA levels found in whole pupae. Oscillations in the levels of the per and tim transcripts are considered to be such a central feature of a normally functioning clock, that it was necessary to repeat this analysis under conditions where per and tim oscillations could be robustly observed (i.e. in adult fly heads). Wild type flies were entrained to a 12:12 LD cycle and flies were collected at four hour intervals for three days. Heads were isolated from the flies collected at each time point and used to prepare total RNA. RNAse protection analyses demonstrated that while per and tim mRNA levels display strong (approximately 10-fold) circadian oscillations, levels of dbt mRNA remain essentially constant (FIG. 12). Therefore, there are two unique features of dbt that distinguish it from per and tim: (a) Strong hypomorphic mutations of this gene are homozygous lethal, and (b) levels of the dbt transcript apparently do not oscillate.

DBT and PER Proteins Physically Interact In Vitro and in Cultured Drosophila Cells: Because DBT and PER appear to be expressed in the same cells in the Drosophila brain and eyes, and patterns of PER phosphorylation and accumulation are altered in dbt mutants, it was asked whether functional interactions between PER and DBT might include a physical association of these proteins. Two independent methods were employed to test and confirm such a physical interaction: in vitro binding studies, and co-immunoprecipitation of DBT and PER from cultured Drosophila cells (S2) programmed to express both proteins.

In vitro translation of DBT from dbt cDNA P12 showed that this cDNA encoded a protein of ~46 kDa as predicted from sequence analysis (FIG. 13A, input). GST (Glutathione-S-transferase) fusions, involving varying segments of PER, were tested for evidence of affinity for this DBT protein. The GST-PER fusions were immobilized on gluthatione agarose beads and subsequently incubated with in vitro translated, $^{35}$S-labeled DBT. After extensive washing to remove nonspecifically bound proteins, SDS-PAGE analysis of labeled DBT proteins bound to the beads showed that DBT binds to PER 1–640 and PER 1–365, but the protein does not bind to PER 530–640 or GST alone. These results show that DBT and PER can physically associate in vitro, and that DBT interacts directly with an N-terminal region of PER.

In order to confirm that such a physical interaction between DBT and PER can take place in Drosophila cells, immunoprecipitations were performed using extracts from four groups of S2 cells, one expressing only a Green Fluorescent Protein (GFP)-DBT fusion, a second co-expressing PER and GFP-DBT, a third producing PER alone, and a fourth expressing neither protein. FIG. 13B shows that when the cell extracts were immunoprecipitated with anti-GFP antibodies, PER-DBT complexes are only detected in cells co-expressing PER and GFP-DBT proteins. The results indicate that PER and DBT are present in a complex when expressed in the same Drosophila cell.

Discussion

The cloning of the dbt gene is reported. This is the third Drosophila gene to be isolated that has an essential role in circadian rhythms. Several lines of evidence were presented to show that the gene cloned is dbt: (a) The P-element insertion associated with dbt$^P$ resides within an intron of the dbt gene and causes a strong reduction in dbt RNA levels. (b) Viability, behavioral rhythmicity, and dbt mRNA levels are restored following simple excision of the P-element associated with dbt$^P$. (c) The dbt$^S$ and dbt$^L$ phenotypes are each associated with single nucleotide mutations, that result in amino acid changes, in the dbt gene. (d) The dbt transcript is detected in the same cell types as are per and tim. (e) DBT has been shown to be capable of binding to PER in vitro and in Drosophila cells. dbt encodes a kinase that is requiredfor wild type patterns of PER phosphorylation andfor adult viability: Sequence analyses indicate that dbt is a structural homologue of human casein kinase I$\epsilon$, with 86% of the amino acids composing DBT identical to those composing the kinase domain of human casein kinase I$\epsilon$. PER proteins are hypo-phosphorylated in dbt$^P$ mutants, and the timing of PER phosphorylation appears to be altered in dbt$^L$ and dbt$^S$ mutants [Example 1, above] suggesting that a kinase activity supplied by DBT is required for normal PER phosphorylation in vivo. In this study it is shown that PER and DBT will physically associate in vitro and in cultured Drosophila cells, and in addition, the formation of a PER/DBT complex leads to DBT-dependent phosphorylation of PER in vitro. DBT is the first Drosophila clock protein to have a structure that indicates a recognizeable biochemical function. Although strong evidence for involvement of protein phosphorylation in circadian rhythmicity has been reported in several organisms [Edery et al., *PNAS USA*, 91:2260–2264

(1994); Garceau et al., *Cell*, 89:469–476 (1997); Price et al., *EMBO J.*, 14:4044–4049 (1995); Roberts et al., *Res.*, 504:211–215 (1989); Schulz et al., *Cronobiol.1 Intern.*, 2:223–233 (1985) and Zwartjes and Eskin, *J. Neurobiol*, 21:376–383 (1989)], this is the first evidence linking a specific kinase to regulation of circadian rhythmicity.

Levels of dbt mRNA show no evident circadian oscillation, so in pacemaker cells, DBT activity may be constitutive. dbt is also the first clock gene to be described in any organism that is essential for viability. The lethality of $dbt^P$ homozygotes is not due to over-accumulation of PER because $per^o$; $dbt^P$ doubly homozygous mutants are inviable [Example 1, above]. Thus, the pupal lethality of $dbt^P$ mutants suggests that vital proteins require DBT activity for their phosphorylation.

Figure 14:
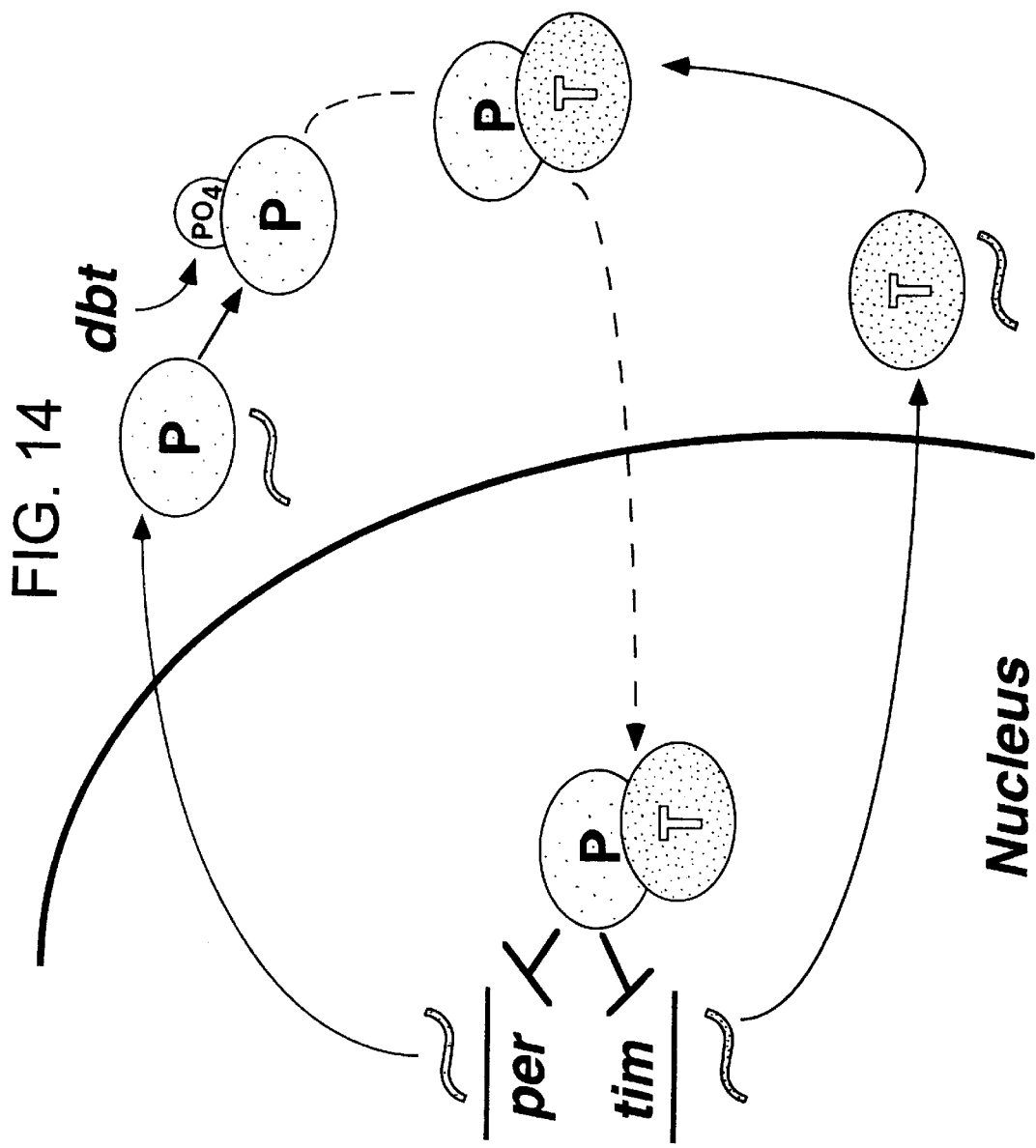
FIG. 14 shows a model depicting regulation of PER phosphorylation and stability by dbt in wild type flies. In the model, dbt function promotes phosphorylation of cytoplasmic PER monomers. Once modified, PER proteins turn over rapidly. Physical association of PER and TIM stabilizes PER either because residual, un-phosphorylated PER proteins are incorporated into PER/TIM dimers and these are no longer subject to modification by DBT, or phosphorylated PER proteins are stabilized by association with TIM. The latter alternative is consistent with Example 1, below because monomeric PER proteins also stably accumulate in nuclei in $dbt^P$ mutants, but not in wild type Drosophila. The model indicates that instability of phosphorylated PER monomers delays PER/TIM heterodimerization (dashed arrow) until per and tim RNA levels are high. Thus, phosphorylation promotes a delay between phases of per/tim transcription and PER/TIM complex function, which establishes molecular oscillations of RNA and protein.

A model for DBT function in a PER/TIM oscillator: FIG. 14 presents a model for the role of DBT in the regulation of circadian rhythms. As DBT and PER physically associate, as hypo-phosphorylated PER proteins accumulate to high levels in $dbt^P$ mutants [Example 1, above], and because PER proteins appear to be unstable in the cytoplasm of pacemaker cells in the absence of TIM in vivo [Dembinska et al., *J. of Bio. Rhythms.*, 12:157–172 (1997); Price et al., *EMBO J.*, 14:4044–4049 (1995) and Vosshall et al., *Science*, 263:1606–1609 (1994), Example 1, above], PER/DBT complexes appear to promote PER phosphorylation(s) that, in turn, destabilizes cytoplasmic PER monomers (FIG. 14). This is further supported by the finding that, in $dbt^P$ larval brains, PER accumulates cytoplasmically in many new cells in the apparent absence of TIM [Kaneko et al., (1997); Example 1, above]. DBT activity thus serves to retard accumulation of PER/TIM complexes in wild type Drosophila, by keeping PER levels low at times of increasing per/tim transcription. As seen with $dbt^P$ mutants, stable PER accumulation favors continuous rather than periodic nuclear transport of PER/TIM complexes, resulting in a feedback loop at equilibrium, rather than a molecular oscillator.

Edery et al. [Edery et al., *PNAS USA*, 91:2260–2264 (1994)] have shown that PER is phosphorylated over many hours, and that the most highly phosphorylated forms of the protein occur at times of night when PER proteins are predominantly nuclear. This suggests that DBT may act in both the cytoplasm and the nucleus, or that additional kinases continue to phosphorylate PER in the nucleus. The present finding that $dbt^P$ mutants accumulate high levels of nuclear PER, and that $dbt^L$ mutants show delayed degradation of hyper-phosphorylated, monomeric forms of PER [Example 1, above], suggests that DBT activity can influence stability of nuclear PER proteins after they have dissociated from TIM. However, this could be due to the production of a phosphorylated form of PER by cytoplasmic DBT, with subsequent transfer of phosphorylated PER to nuclei as a PER/TIM complex. It is not yet known whether all monomeric PER proteins are phosphorylated in response to DBT, so that PER/TIM complexes stabilize previously phosphorylated PER proteins, or whether only PER proteins that have escaped phosphorylation as a monomer contribute to PER/TIM complexes (see also FIG. 14, legend).

Why $dbt^S$ and $dbt^L$ mutations are semi-dominant: The amino acids affected in $DBT^S$ and $DBT^L$ are highly conserved in the catalytic domains of other casein kinase I family members (FIG. 11). Thus, $DBT^S$ and $DBT^L$ may have altered kinase activities. However, changes in enzyme activity are not easily linked to the semi-dominant rhythm phenotypes produced by these mutations; studies of flies carrying 1 to 3 copies of the wild type gene have indicated that period length is relatively insensitive to dbt gene dosage [Example 1, above].

Although the basis for $dbt^S$ and $dbt^L$ semi-dominance is unknown, one possibility is that semi-dominance reflects a stable stoichiometric interaction between PER and DBT in vivo, as the two proteins have been shown to physically interact in vitro and in cultured Drosophila cells (FIG. 13). For example, in $dbt^S/dbt^+$ flies, there might be distinct pools of PER- one complexed to wild type DBT and one to $DBT^S$. PER complexed to $DBT^S$ should be prematurely degraded as in $dbt^S$ homozygotes [Example 1, above]. In $dbt^L/dbt^+$ flies, degradation should be delayed for PER/$DBT^L$ complexes as in $dbt^L$ homozygotes [Example 1, above].

It is possible that alterations in protein affinities have occurred for mutant DBT and wild type PER proteins. If $DBT^S$, for example, were to interact more strongly with PER than wild type DBT, degradation might be enhanced in $dbt^S/dbt^+$ in comparison to wild type. However, even if changes in PER/DBT affinity were associated with the mutants, there would still be a requirement for functionally distinct pools of PER/DBT complexes, as outlined above, to produce the observed molecular and behavioral mutant phenotypes. Differences in the stability of wild type, $DBT^L$ and $DBT^S$ proteins cannot be ruled out in the absence of an antibody, but once again this seems unlikely given the dosage insensitivity of wild type DBT.

Structural homologues of two Drosophila clock genes are now recognized in mammals: per homologues have recently been identified in mice and humans, and cycling patterns of per expression in the suprachiasmatic nucleus (SCN), the mouse pacemaker, suggest a role in the regulation of mammalian circadian rhytlms as in Drosophila [Albrecht et al., *Cell*, 91:1055–15 1064 (1997); Shearman et al., *Neuron*, 19:1261–1269 (1997); Shigeyoshi et al., *Cell*, 91:1043–1053 (1997); Sun et al., *Cell*, 90:1003–1011 (1997) and Tei et al., *Nature*, 389:512–516 (1997)]. As the protein encoded by dbt is closely related to a human casein kinase, it is likely that a specific DBT homologue is expressed in cells composing the SCN, and that such a kinase similarly regulates the phosphorylation and stability of PER to control mammalian circadian rhythms.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended clairm.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method of identifying an agent that modulates the interaction between a PERIOD (PER) protein and a DOUBLETIME (DBT) protein comprising:
   (a) contacting the PER protein with the DBT protein in the presence of the agent under conditions in which the DBT protein binds the PER protein in the absence of the agent; and
   (b) measuring the binding of the PER protein and the DBT protein; wherein when the binding of the PER protein with the DBT protein is different in the presence of the agent than in its absence, an agent that modulates the interaction between the PER protein and the DBT protein is identified.

2. A method of identifying a compound that modulates the phosphorylation of a PERIOD (PER) protein by a DOUBLETIME (DBT) protein comprising:
   (a) contacting the PER protein with the DBT protein in the presence of the compound under conditions in which the DBT protein phosphorylates the PER protein in the absence of the compound; and
   (b) measuring the phosphorylation of the PER protein; wherein when the phosphorylation of the PER protein is different in the presence of the compound than in its absence a compound that modulates the phosphorylation of the PER protein by the DBT protein is identified.

3. The method of claim 1 wherein the step of determining the binding of the PER protein and the DBT protein includes determining the dissociation constant between the PER protein and the DBT protein.

4. The method of claim 1 wherein a fragment of the PER protein and a fragment of the DBT protein are used in place of the PER protein and the DBT protein; wherein the fragment of the PER protein retains its DBT protein binding capacity, whereas the fragment of the DBT protein retains its PER protein binding capacity.

5. The method of claim 1, wherein the DBT protein is human casein kinase Iε.

6. The method of claim 2 wherein a fragment of the PER protein and a fragment of the DBT protein are used in place of the PER protein and the DBT protein; wherein the fragment of the PER protein retains its phosphorylation site, whereas the fragment of the DBT protein retains its kinase activity.

7. The method of claim 2, wherein the DBT protein is human casein kinase Iε.

8. The method of claim 7, wherein the human casein kinase Iε has the amino acid sequence of SEQ ID NO:9.

9. The method of claim 7, wherein the human casein kinase Iε has the amino acid sequence of SEQ ID NO:9 comprising a conservative amino acid substitution.

10. The method of claim 6, wherein the fragment of the DBT protein is a fragment of the DBT protein having the amino acid sequence of SEQ ID NO:2.

11. The method of claim 6, wherein the fragment of the DBT protein is a fragment of the DBT protein having the amino acid sequence of SEQ ID NO:2 comprising a conservative amino acid substitution.

12. The method of claim 6, wherein the fragment of the DBT protein is a fragment of a human casein kinase Iε.

13. The method of claim 12, wherein the fragment of the DBT protein is a fragment of the human casein kinase Iε having the amino acid sequence of SEQ ID NO:9.

14. The method of claim 12, wherein the fragment of the DBT protein is a fragment of the human casein kinase Iε having the amino acid sequence of SEQ ID NO:9 comprising a conservative amino acid substitution.

15. The method of claim 12, wherein the DBT protein has the amino acid sequence of SEQ ID NO:2.

16. The method of claim 12, wherein the DBT protein has the amino acid sequence of SEQ ID NO:2 comprising a conservative amino acid substitution.

17. The method of claim 5, wherein the human casein kinase Iε has the amino acid sequence of SEQ ID NO:9.

18. The method of claim 5, wherein the human casein kinase Iε has the amino acid sequence of SEQ ID NO:9 comprising a conservative amino acid substitution.

19. The method of claim 4, wherein the fragment of the DBT protein is a fragment of the DBT protein having the amino acid sequence of SEQ ID NO:2.

20. The method of claim 4, wherein the fragment of the DBT protein is a fragment of the DBT protein having the amino acid sequence of SEQ ID NO:2 comprising a conservative amino acid substitution.

21. The method of claim 4, wherein the fragment of the DBT protein is a fragment of a human casein kinase Iε.

22. The method of claim 21, wherein the fragment of the DBT protein is a fragment of the human casein kinase Iε having the amino acid sequence of SEQ ID NO:9.

23. The method of claim 21, wherein the fragment of the DBT protein is a fragment of the human casein kinase Iε having the amino acid sequence of SEQ ID NO:9 comprising a conservative amino acid substitution.

24. The method of claim 1, wherein the DBT protein has the amino acid sequence of SEQ ID NO:2.

25. The method of claim 1, wherein the DBT protein has the amino acid sequence of SEQ ID NO:2 comprising a conservative amino acid substitution.

* * * * *

SEQUENCE LISTING

<160> NUMBER OF SEQ ID NOS: 14

<210> SEQ ID NO 1
<211> LENGTH: 1520
<212> TYPE: DNA
<213> ORGANISM: Drosophila melanogaster

<400> SEQUENCE: 1

| | | | | | |
|---|---|---|---|---|---|
| aaatccgagg | aaccgaggag | tccgaactct | accacacaga | aacccacaga | aacagacgta | 60 |
| acaaaatgga | gctgcgcgtg | ggtaacaaat | atcgcctggg | ccgcaagata | ggatcgggat | 120 |
| cgttcggcga | catctacctg | ggcaccacga | tcaacactgg | cgaggaggtg | gccatcaagc | 180 |
| tggagtgcat | ccgcaccaaa | cacccccagc | tgcacatcga | gtcaaagttc | tacaagacga | 240 |
| tgcagggtgg | cataggcata | ccccgcataa | tctggtgcgg | cagcgagggc | gactacaatg | 300 |
| tgatggtgat | ggagctactc | ggaccctcgc | tggaggacct | cttcaacttt | tgttcacgcc | 360 |
| gcttttcgtt | gaagacggtt | ctgctgctgg | cggaccagat | gatctcccgc | atcgattaca | 420 |
| tacactcgcg | ggacttcatc | catcgcgaca | tcaagccgga | taacttcctc | atgggtcttg | 480 |
| gcaagaaggg | caacctggtg | tacatcattg | actttggcct | ggccaagaaa | ttccgcgatg | 540 |
| cccggtcgct | gaagcacatt | ccctatcggg | aaaacaagaa | cctcacgggc | actgcccgct | 600 |
| atgcctccat | caacacacat | ttgggcattg | agcaatcgcg | tcgtgacgac | ctggagtccc | 660 |
| tgggttacgt | cctaatgtac | ttcaatctgg | gcgccttgcc | ctggcagggc | ttaaaggcag | 720 |
| ccaacaagag | gcaaaagtac | gagaggatct | cggagaagaa | gctgtccacc | tcgattgtgg | 780 |
| tgctgtgcaa | gggcttcccc | agcgagttcg | tcaactatct | gaacttctgt | cgccagatgc | 840 |
| atttcgacca | gcgtcccgat | tactgccacc | tgcgcaaact | cttccgcaac | ttgttccacc | 900 |
| gtttgggctt | cacttacgac | tatgtgtttg | actggaacct | gcttaagttt | ggcggacctc | 960 |
| gcaatcccca | ggcgattcag | caggcgcagg | acggagcgga | cggccaggcg | ggtcatgatg | 1020 |
| cggtggccgc | agcagcggcg | gtggcagcag | cggcagccgc | ctcctcgcat | caacagcagc | 1080 |
| agcacaaggt | caatgcggcg | ctgggtggcg | gaggaggcag | tcgtgcgcaa | cagcaactcc | 1140 |
| agggcggcca | aacgctggcg | atgctgggcg | gcaatggagg | cggtaacggc | agccaactga | 1200 |
| tcggcggcaa | cggactcaac | atggacgatt | cgatggcggc | caccaactcg | tcgagaccgc | 1260 |
| cgtacgacac | gccggagcgt | cggcccctcga | tacggatgcg | gcagggaggc | ggtggtggcg | 1320 |
| gcggtggagt | gggcgtaggc | ggtatgcaga | gcggcggagg | gggcggtggc | gtggggaacg | 1380 |
| ccaaataata | ttttatcgtt | taggttgcga | cgctggacac | gacacagtag | acaaacaaca | 1440 |
| acagaactca | acaaactata | catgtagtat | atatagttat | ataacctaa | tatatataat | 1500 |
| acttgcttta | tatatgcggt | | | | | 1520 |

<210> SEQ ID NO 2
<211> LENGTH: 440
<212> TYPE: PRT
<213> ORGANISM: Drosophila melanogaster

<400> SEQUENCE: 2

Met Glu Leu Arg Val Gly Asn Lys Tyr Arg Leu Gly Arg Lys Ile Gly
 1               5                  10                  15

Ser Gly Ser Phe Gly Asp Ile Tyr Leu Gly Thr Thr Ile Asn Thr Gly
            20                  25                  30

Glu Glu Val Ala Ile Lys Leu Glu Cys Ile Arg Thr Lys His Pro Gln

```
                 35                  40                  45
Leu His Ile Glu Ser Lys Phe Tyr Lys Thr Met Gln Gly Gly Ile Gly
         50                  55                  60

Ile Pro Arg Ile Ile Trp Cys Gly Ser Glu Gly Asp Tyr Asn Val Met
 65                  70                  75                  80

Val Met Glu Leu Leu Gly Pro Ser Leu Glu Asp Leu Phe Asn Phe Cys
                 85                  90                  95

Ser Arg Arg Phe Ser Leu Lys Thr Val Leu Leu Ala Asp Gln Met
                100                 105                 110

Ile Ser Arg Ile Asp Tyr Ile His Ser Arg Asp Phe Ile His Arg Asp
                115                 120                 125

Ile Lys Pro Asp Asn Phe Leu Met Gly Leu Gly Lys Lys Gly Asn Leu
130                 135                 140

Val Tyr Ile Ile Asp Phe Gly Leu Ala Lys Lys Phe Arg Asp Ala Arg
145                 150                 155                 160

Ser Leu Lys His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
                180                 185                 190

Arg Asp Asp Leu Glu Ser Leu Gly Tyr Val Leu Met Tyr Phe Asn Leu
                195                 200                 205

Gly Ala Leu Pro Trp Gln Gly Leu Lys Ala Ala Asn Lys Arg Gln Lys
210                 215                 220

Tyr Glu Arg Ile Ser Glu Lys Lys Leu Ser Thr Ser Ile Val Val Leu
225                 230                 235                 240

Cys Lys Gly Phe Pro Ser Glu Phe Val Asn Tyr Leu Asn Phe Cys Arg
                245                 250                 255

Gln Met His Phe Asp Gln Arg Pro Asp Tyr Cys His Leu Arg Lys Leu
                260                 265                 270

Phe Arg Asn Leu Phe His Arg Leu Gly Phe Thr Tyr Asp Tyr Val Phe
                275                 280                 285

Asp Trp Asn Leu Leu Lys Phe Gly Gly Pro Arg Asn Pro Gln Ala Ile
290                 295                 300

Gln Gln Ala Gln Asp Gly Ala Asp Gly Gln Ala Gly His Asp Ala Val
305                 310                 315                 320

Ala Ala Ala Ala Ala Val Ala Ala Ala Ala Ala Ser Ser His Gln
                325                 330                 335

Gln Gln Gln His Lys Val Asn Ala Ala Leu Gly Gly Gly Gly Ser
                340                 345                 350

Arg Ala Gln Gln Gln Leu Gln Gly Gly Gln Thr Leu Ala Met Leu Gly
                355                 360                 365

Gly Asn Gly Gly Asn Gly Ser Gln Leu Ile Gly Gly Asn Gly Leu
370                 375                 380

Asn Met Asp Asp Ser Met Ala Ala Thr Asn Ser Ser Arg Pro Pro Tyr
385                 390                 395                 400

Asp Thr Pro Glu Arg Arg Pro Ser Ile Arg Met Arg Gln Gly Gly Gly
                405                 410                 415

Gly Gly Gly Gly Gly Val Gly Val Gly Gly Met Gln Ser Gly Gly Gly
                420                 425                 430

Gly Gly Gly Val Gly Asn Ala Lys
                435                 440
```

<210> SEQ ID NO 3

```
<211> LENGTH: 440
<212> TYPE: PRT
<213> ORGANISM: Drosophila melanogaster

<400> SEQUENCE: 3

Met Glu Leu Arg Val Gly Asn Lys Tyr Arg Leu Gly Arg Lys Ile Gly
  1               5                  10                  15

Ser Gly Ser Phe Gly Asp Ile Tyr Leu Gly Thr Thr Ile Asn Thr Gly
             20                  25                  30

Glu Glu Val Ala Ile Lys Leu Glu Cys Ile Arg Thr Lys His Ser Gln
         35                  40                  45

Leu His Ile Glu Ser Lys Phe Tyr Lys Thr Met Gln Gly Gly Ile Gly
     50                  55                  60

Ile Pro Arg Ile Ile Trp Cys Gly Ser Glu Gly Asp Tyr Asn Val Met
 65                  70                  75                  80

Val Met Glu Leu Leu Gly Pro Ser Leu Glu Asp Leu Phe Asn Phe Cys
                 85                  90                  95

Ser Arg Arg Phe Ser Leu Lys Thr Val Leu Leu Ala Asp Gln Met
            100                 105                 110

Ile Ser Arg Ile Asp Tyr Ile His Ser Arg Asp Phe Ile His Arg Asp
        115                 120                 125

Ile Lys Pro Asp Asn Phe Leu Met Gly Leu Gly Lys Lys Gly Asn Leu
130                 135                 140

Val Tyr Ile Ile Asp Phe Gly Leu Ala Lys Lys Phe Arg Asp Ala Arg
145                 150                 155                 160

Ser Leu Lys His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ala Leu Pro Trp Gln Gly Leu Lys Ala Ala Asn Lys Arg Gln Lys
210                 215                 220

Tyr Glu Arg Ile Ser Glu Lys Lys Leu Ser Thr Ser Ile Val Val Leu
225                 230                 235                 240

Cys Lys Gly Phe Pro Ser Glu Phe Val Asn Tyr Leu Asn Phe Cys Arg
                245                 250                 255

Gln Met His Phe Asp Gln Arg Pro Asp Tyr Cys His Leu Arg Lys Leu
            260                 265                 270

Phe Arg Asn Leu Phe His Arg Leu Gly Phe Thr Tyr Asp Tyr Val Phe
        275                 280                 285

Asp Trp Asn Leu Leu Lys Phe Gly Gly Pro Arg Asn Pro Gln Ala Ile
290                 295                 300

Gln Gln Ala Gln Asp Gly Ala Asp Gly Gln Ala Gly His Asp Ala Val
305                 310                 315                 320

Ala Ala Ala Ala Ala Val Ala Ala Ala Ala Ala Ser Ser His Gln
                325                 330                 335

Gln Gln Gln His Lys Val Asn Ala Ala Leu Gly Gly Gly Gly Ser
            340                 345                 350

Arg Ala Gln Gln Gln Leu Gln Gly Gly Gln Thr Leu Ala Met Leu Gly
            355                 360                 365

Gly Asn Gly Gly Gly Asn Gly Ser Gln Leu Ile Gly Gly Asn Gly Leu
        370                 375                 380

Asn Met Asp Asp Ser Met Ala Ala Thr Asn Ser Ser Arg Pro Pro Tyr
```

```
385                 390                 395                 400
Asp Thr Pro Glu Arg Arg Pro Ser Ile Arg Met Arg Gln Gly Gly Gly
                    405                 410                 415
Gly Gly Gly Gly Gly Val Gly Val Gly Gly Met Gln Ser Gly Gly Gly
            420                 425                 430
Gly Gly Gly Val Gly Asn Ala Lys
        435                 440

<210> SEQ ID NO 4
<211> LENGTH: 440
<212> TYPE: PRT
<213> ORGANISM: Drosophila melanogaster

<400> SEQUENCE: 4

Met Glu Leu Arg Val Gly Asn Lys Tyr Arg Leu Gly Arg Lys Ile Gly
 1               5                  10                  15
Ser Gly Ser Phe Gly Asp Ile Tyr Leu Gly Thr Thr Ile Asn Thr Gly
                20                  25                  30
Glu Glu Val Ala Ile Lys Leu Glu Cys Ile Arg Thr Lys His Pro Gln
            35                  40                  45
Leu His Ile Glu Ser Lys Phe Tyr Lys Thr Met Gln Gly Gly Ile Gly
        50                  55                  60
Ile Pro Arg Ile Ile Trp Cys Gly Ser Glu Gly Asp Tyr Asn Val Ile
65                  70                  75                  80
Val Met Glu Leu Leu Gly Pro Ser Leu Glu Asp Leu Phe Asn Phe Cys
                85                  90                  95
Ser Arg Arg Phe Ser Leu Lys Thr Val Leu Leu Leu Ala Asp Gln Met
            100                 105                 110
Ile Ser Arg Ile Asp Tyr Ile His Ser Arg Asp Phe Ile His Arg Asp
        115                 120                 125
Ile Lys Pro Asp Asn Phe Leu Met Gly Leu Gly Lys Lys Gly Asn Leu
    130                 135                 140
Val Tyr Ile Ile Asp Phe Gly Leu Ala Lys Lys Phe Arg Asp Ala Arg
145                 150                 155                 160
Ser Leu Lys His Ile Pro Tyr Arg Glu Asn Lys Asn Leu Thr Gly Thr
                165                 170                 175
Ala Arg Tyr Ala Ser Ile Asn Thr His Leu Gly Ile Glu Gln Ser Arg
            180                 185                 190
Arg Asp Asp Leu Glu Ser Leu Gly Tyr Val Leu Met Tyr Phe Asn Leu
        195                 200                 205
Gly Ala Leu Pro Trp Gln Gly Leu Lys Ala Ala Asn Lys Arg Gln Lys
    210                 215                 220
Tyr Glu Arg Ile Ser Glu Lys Lys Leu Ser Thr Ser Ile Val Val Leu
225                 230                 235                 240
Cys Lys Gly Phe Pro Ser Glu Phe Val Asn Tyr Leu Asn Phe Cys Arg
                245                 250                 255
Gln Met His Phe Asp Gln Arg Pro Asp Tyr Cys His Leu Arg Lys Leu
            260                 265                 270
Phe Arg Asn Leu Phe His Arg Leu Gly Phe Thr Tyr Asp Tyr Val Phe
        275                 280                 285
Asp Trp Asn Leu Leu Lys Phe Gly Gly Pro Arg Asn Pro Gln Ala Ile
    290                 295                 300
Gln Gln Ala Gln Asp Gly Ala Asp Gly Gln Ala Gly His Asp Ala Val
305                 310                 315                 320
```

```
Ala Ala Ala Ala Ala Val Ala Ala Ala Ala Ser Ser His Gln
            325                 330                 335

Gln Gln Gln His Lys Val Asn Ala Ala Leu Gly Gly Gly Gly Ser
            340                 345                 350

Arg Ala Gln Gln Gln Leu Gln Gly Gly Gln Thr Leu Ala Met Leu Gly
            355                 360                 365

Gly Asn Gly Gly Asn Gly Ser Gln Leu Ile Gly Gly Asn Gly Leu
            370                 375                 380

Asn Met Asp Asp Ser Met Ala Ala Thr Asn Ser Ser Arg Pro Pro Tyr
385                 390                 395                 400

Asp Thr Pro Glu Arg Arg Pro Ser Ile Arg Met Arg Gln Gly Gly
                405                 410                 415

Gly Gly Gly Gly Val Gly Val Gly Met Gln Ser Gly Gly
            420                 425                 430

Gly Gly Gly Val Gly Asn Ala Lys
            435                 440

<210> SEQ ID NO 5
<211> LENGTH: 72
<212> TYPE: DNA
<213> ORGANISM: Drosophila melanogaster

<400> SEQUENCE: 5
ataggatcgg gatcgttcgg cgacatctac ctgggcacca cgatcaacac tggcgaggag    60
gtggccatca ag                                                       72

<210> SEQ ID NO 6
<211> LENGTH: 24
<212> TYPE: PRT
<213> ORGANISM: Drosophila melanogaster

<400> SEQUENCE: 6

Ile Gly Ser Gly Ser Phe Gly Asp Ile Tyr Leu Gly Thr Thr Ile Asn
  1               5                  10                  15

Thr Gly Glu Glu Val Ala Ile Lys
            20

<210> SEQ ID NO 7
<211> LENGTH: 39
<212> TYPE: DNA
<213> ORGANISM: Drosophila melanogaster

<400> SEQUENCE: 7
ttcatccatc gcgacatcaa gccggataac ttcctcatg                           39

<210> SEQ ID NO 8
<211> LENGTH: 13
<212> TYPE: PRT
<213> ORGANISM: Drosophila melanogaster

<400> SEQUENCE: 8

Phe Ile His Arg Asp Ile Lys Pro Asp Asn Phe Leu Met
  1               5                  10

<210> SEQ ID NO 9
<211> LENGTH: 416
<212> TYPE: PRT
<213> ORGANISM: Homo sapiens

<400> SEQUENCE: 9
```

-continued

```
Met Glu Leu Arg Val Gly Asn Lys Tyr Arg Leu Gly Arg Lys Ile Gly
 1               5                  10                  15

Ser Gly Ser Phe Gly Asp Ile Tyr Leu Gly Ala Asn Ile Ala Ser Gly
                20                  25                  30

Glu Glu Val Ala Ile Lys Leu Glu Cys Val Lys Thr Lys His Pro Gln
            35                  40                  45

Leu His Ile Glu Ser Lys Phe Tyr Lys Met Met Gln Gly Gly Val Gly
        50                  55                  60

Ile Pro Ser Ile Lys Trp Cys Gly Ala Glu Gly Asp Tyr Asn Val Met
 65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285

Asp Trp Asn Met Leu Lys Phe Gly Ala Ala Arg Asn Pro Glu Asp Val
290                 295                 300

Asp Arg Glu Arg Arg Glu His Glu Arg Glu Glu Arg Met Gly Gln Leu
305                 310                 315                 320

Arg Gly Ser Ala Thr Arg Ala Leu Pro Pro Gly Pro Pro Thr Gly Ala
                325                 330                 335

Thr Ala Asn Arg Leu Arg Ser Ala Ala Glu Pro Val Ala Ser Thr Pro
            340                 345                 350

Ala Ser Arg Ile Gln Pro Ala Gly Asn Thr Ser Pro Arg Ala Ile Ser
        355                 360                 365

Arg Val Asp Arg Glu Arg Lys Val Ser Met Arg Leu His Arg Gly Ala
370                 375                 380

Pro Ala Asn Val Ser Ser Ser Asp Leu Thr Gly Arg Gln Glu Val Ser
385                 390                 395                 400

Arg Ile Pro Ala Ser Gln Thr Ser Val Pro Phe Asp His Leu Gly Lys
                405                 410                 415
```

```
<210> SEQ ID NO 10
<211> LENGTH: 319
<212> TYPE: PRT
<213> ORGANISM: Arabidopsis thaliana

<400> SEQUENCE: 10

Met Asp Leu Val Ile Gly Gly Lys Phe Lys Leu Gly Arg Lys Ile Gly
 1               5                  10                  15

Ser Gly Ser Phe Gly Glu Leu Tyr Leu Gly Ile Asn Val Gln Thr Gly
            20                  25                  30

Glu Glu Val Ala Val Lys Leu Glu Ser Val Lys Thr Lys His Pro Gln
        35                  40                  45

Leu His Tyr Glu Ser Lys Leu Tyr Met Leu Leu Gln Gly Gly Thr Gly
    50                  55                  60

Val Pro Asn Leu Lys Trp Tyr Gly Val Glu Gly Asp Tyr Asn Val Met
65                  70                  75                  80

Val Ile Asp Leu Leu Gly Pro Ser Leu Glu Asp Leu Phe Asn Tyr Cys
                85                  90                  95

Asn Arg Lys Leu Ser Leu Lys Thr Val Leu Met Leu Ala Asp Gln Leu
            100                 105                 110

Ile Asn Arg Val Glu Phe Met His Thr Arg Gly Phe Leu His Arg Asp
        115                 120                 125

Ile Lys Pro Asp Asn Phe Leu Met Gly Leu Gly Arg Lys Ala Asn Gln
    130                 135                 140

Val Tyr Ile Ile Asp Phe Gly Leu Gly Lys Lys Tyr Arg Asp Leu Gln
145                 150                 155                 160

Thr His Arg His Ile Pro Tyr Arg Glu Asn Lys Asn Leu Thr Gly Thr
                165                 170                 175

Ala Arg Tyr Ala Ser Val Asn Thr His Leu Gly Val Glu Gln Ser Arg
            180                 185                 190

Arg Asp Leu Glu Ala Leu Gly Tyr Val Leu Met Tyr Phe Leu Lys
        195                 200                 205

Gly Ser Leu Pro Trp Gln Gly Leu Lys Ala Gly Thr Lys Lys Gln Lys
    210                 215                 220

Tyr Asp Arg Ile Ser Glu Lys Lys Val Ala Thr Pro Ile Glu Val Leu
225                 230                 235                 240

Cys Lys Asn Gln Pro Ser Glu Phe Val Ser Tyr Phe Arg Tyr Cys Arg
                245                 250                 255

Ser Leu Arg Phe Asp Asp Lys Pro Asp Tyr Ser Tyr Leu Lys Arg Leu
            260                 265                 270

Phe Arg Asp Leu Phe Ile Arg Glu Gly Tyr Gln Phe Asp Tyr Val Phe
        275                 280                 285

Asp Trp Thr Val Leu Lys Tyr Pro Gln Ile Gly Ser Ser Ser Gly Ser
    290                 295                 300

Ser Ser Arg Thr Arg Val Val Tyr Ala Ala Phe Ser Phe Gly Ser
305                 310                 315

<210> SEQ ID NO 11
<211> LENGTH: 337
<212> TYPE: PRT
<213> ORGANISM: Xenopus laevis

<400> SEQUENCE: 11

Met Ala Ser Ser Ser Gly Ser Lys Ala Glu Phe Ile Val Gly Gly Lys
 1               5                  10                  15

Tyr Lys Leu Val Arg Lys Ile Gly Ser Gly Ser Phe Gly Asp Ile Tyr
```

```
                   20                  25                  30

Leu Ala Ile Asn Ile Thr Asn Gly Glu Glu Val Ala Val Lys Leu Glu
         35                  40                  45

Ser Gln Lys Ala Arg His Pro Gln Leu Leu Tyr Glu Ser Lys Leu Tyr
 50                  55                  60

Lys Ile Leu Gln Gly Gly Val Gly Ile Pro His Ile Arg Trp Tyr Gly
 65                  70                  75                  80

Gln Glu Lys Asp Tyr Asn Val Leu Val Met Asp Leu Leu Gly Pro Ser
                 85                  90                  95

Leu Glu Asp Leu Phe Asn Phe Cys Ser Arg Arg Phe Thr Met Lys Thr
             100                 105                 110

Val Leu Met Leu Ala Asp Gln Met Ile Ser Arg Ile Glu Tyr Val His
         115                 120                 125

Thr Lys Asn Phe Ile His Arg Asp Ile Lys Pro Asp Asn Phe Leu Met
 130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                 165                 170                 175

Glu Asp Lys Asn Leu Thr Gly Thr Ala Arg Tyr Ala Ser Ile Asn Ala
             180                 185                 190

His Leu Gly Ile Glu Gln Ser Arg Arg Asp Asp Met Glu Ser Leu Gly
         195                 200                 205

Tyr Val Leu Met Tyr Phe Asn Arg Thr Ser Leu Pro Trp Gln Gly Leu
 210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                 245                 250                 255

Ala Met Tyr Leu Asn Tyr Cys Arg Gly Leu Arg Phe Glu Glu Ala Pro
             260                 265                 270

Asp Tyr Met Tyr Leu Arg Gln Leu Phe Arg Ile Leu Phe Arg Thr Leu
         275                 280                 285

Asn His Gln Tyr Asp Tyr Thr Phe Asp Trp Thr Met Leu Lys Gln Lys
 290                 295                 300

Ala Ala Gln Gln Ala Ala Ser Ser Gly Gln Gly Gln Ala Gln
305                 310                 315                 320

Thr Pro Thr Gly Lys Gln Thr Asp Lys Ser Lys Ser Asn Met Lys Gly
                 325                 330                 335

Phe

<210> SEQ ID NO 12
<211> LENGTH: 337
<212> TYPE: PRT
<213> ORGANISM: Gallus gallus

<400> SEQUENCE: 12

Met Ala Ser Ser Ser Gly Ser Lys Ala Glu Phe Ile Val Gly Gly Lys
  1               5                  10                  15

Tyr Lys Leu Val Arg Lys Ile Gly Ser Gly Ser Phe Gly Asp Ile Tyr
                 20                  25                  30

Leu Ala Ile Asn Ile Thr Asn Gly Glu Glu Val Ala Val Lys Leu Glu
             35                  40                  45

Ser Gln Lys Ala Arg His Pro Gln Leu Leu Tyr Glu Ser Lys Leu Tyr
```

-continued

```
                50                  55                  60
Lys Ile Leu Gln Gly Gly Val Gly Ile Pro His Ile Arg Trp Tyr Gly
 65                  70                  75                  80

Gln Glu Lys Asp Tyr Asn Val Leu Val Met Asp Leu Leu Gly Pro Ser
                 85                  90                  95

Leu Glu Asp Leu Phe Asn Phe Cys Ser Arg Arg Phe Thr Met Lys Thr
                100                 105                 110

Val Leu Met Leu Ala Asp Gln Met Ile Ser Arg Ile Glu Tyr Val His
                115                 120                 125

Thr Lys Asn Phe Ile His Arg Asp Ile Lys Pro Asp Asn Phe Leu Met
130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
                180                 185                 190

His Leu Gly Ile Glu Gln Ser Arg Arg Asp Asp Met Glu Ser Leu Gly
                195                 200                 205

Tyr Val Leu Met Tyr Phe Asn Arg Thr Ser Leu Pro Trp Gln Gly Leu
210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
                260                 265                 270

Asp Tyr Met Tyr Leu Arg Gln Leu Phe Arg Ile Leu Phe Arg Thr Leu
                275                 280                 285

Asn His Gln Tyr Asp Tyr Thr Phe Asp Trp Thr Met Leu Lys Gln Lys
290                 295                 300

Ala Ala Gln Gln Ala Ala Ser Ser Ser Gly Gln Gly Gln Gln Ala Gln
305                 310                 315                 320

Thr Pro Thr Gly Lys Gln Thr Asp Lys Ser Lys Ser Asn Met Lys Gly
                325                 330                 335

Phe
```

<210> SEQ ID NO 13
<211> LENGTH: 365
<212> TYPE: PRT
<213> ORGANISM: Schizosaccharomyces pombe

<400> SEQUENCE: 13

```
Met Ala Leu Asp Leu Arg Ile Gly Asn Lys Tyr Arg Ile Gly Arg Lys
  1               5                  10                  15

Ile Gly Ser Gly Ser Phe Gly Asp Ile Tyr Leu Gly Thr Asn Val Val
                 20                  25                  30

Ser Gly Glu Glu Val Ala Ile Lys Leu Glu Ser Thr Arg Ala Lys His
                 35                  40                  45

Pro Gln Leu Glu Tyr Glu Tyr Arg Val Tyr Arg Ile Leu Ser Gly Gly
                 50                  55                  60

Val Gly Ile Pro Phe Val Arg Trp Phe Gly Val Glu Cys Asp Tyr Asn
 65                  70                  75                  80

Ala Met Val Met Asp Leu Leu Gly Pro Ser Leu Glu Asp Leu Phe Asn
```

```
              85                  90                  95
Phe Cys Asn Arg Lys Phe Ser Leu Lys Thr Val Leu Leu Leu Ala Asp
                100                 105                 110
Gln Leu Ile Ser Arg Ile Glu Phe Ile His Ser Lys Ser Phe Leu His
            115                 120                 125
Arg Asp Ile Lys Pro Asp Asn Phe Leu Met Gly Ile Gly Lys Arg Gly
        130                 135                 140
Asn Gln Val Asn Ile Ile Asp Phe Gly Leu Ala Lys Lys Tyr Arg Asp
145                 150                 155                 160
His Lys Thr His Leu His Ile Pro Tyr Arg Glu Asn Lys Asn Leu Thr
                165                 170                 175
Gly Thr Ala Arg Tyr Ala Ser Ile Asn Thr His Leu Gly Ile Glu Gln
            180                 185                 190
Ser Arg Arg Asp Asp Leu Glu Ser Leu Gly Tyr Val Leu Val Tyr Phe
        195                 200                 205
Cys Arg Gly Ser Leu Pro Trp Gln Gly Leu Lys Ala Thr Thr Lys Lys
    210                 215                 220
Gln Lys Tyr Glu Lys Ile Met Glu Lys Lys Ile Ser Thr Pro Thr Glu
225                 230                 235                 240
Val Leu Cys Arg Gly Phe Pro Gln Glu Phe Ser Ile Tyr Leu Asn Tyr
                245                 250                 255
Thr Arg Ser Leu Arg Phe Asp Asp Lys Pro Asp Tyr Ala Tyr Leu Arg
            260                 265                 270
Lys Leu Phe Arg Asp Leu Phe Cys Arg Gln Ser Tyr Glu Phe Asp Tyr
        275                 280                 285
Met Phe Asp Trp Thr Leu Lys Arg Lys Thr Gln Gln Asp Gln Gln His
    290                 295                 300
Gln Gln Gln Leu Gln Gln Leu Ser Ala Thr Pro Gln Ala Ile Asn
305                 310                 315                 320
Pro Pro Pro Glu Arg Ser Ser Phe Arg Asn Tyr Gln Lys Gln Asn Phe
                325                 330                 335
Asp Glu Lys Gly Gly Asp Ile Asn Thr Thr Val Pro Val Ile Asn Asp
            340                 345                 350
Pro Ser Ala Thr Gly Ala Gln Tyr Ile Asn Arg Pro Asn
        355                 360                 365

<210> SEQ ID NO 14
<211> LENGTH: 1331
<212> TYPE: DNA
<213> ORGANISM: Homo sapiens

<400> SEQUENCE: 14
gaattccggg caagagtgag ccatggagct acgtgtgggg aacaagtacc gcctgggacg      60
gaagatcggg agcgggtcct tcggagatat ctacctgggt gccaacatcg cctctggtga     120
ggaagtcgcc atcaagctgg agtgtgtgaa gacaaagcac ccccagctgc acatcgagag     180
caagttctac aagatgatgc agggtggcgt ggggatcccg tccatcaagt ggtgcggagc     240
tgagggcgac tacaacgtga tggtcatgga gctgctgggg cctagcctcg aggacctgtt     300
caacttctgt tcccgcaaat tcagcctcaa gacggtgctg ctcttggccg accagatgat     360
cagccgcatc gagtatatcc actccaagaa cttcatccac cgggacgtca agcccgacaa     420
cttcctcatg gggctgggga agaagggcaa cctggtctac atcatcgact cgggcctggc     480
caagaagtac cgggacgccc gcacccacca gcacattccc taccgggaaa acaagaacct     540
```

-continued

```
gaccggcacg gcccgctacg cttccatcaa cacgcacctg ggcattgagc aaagccgtcg    600
agatgacctg gagagcctgg gctacgtgct catgtacttc aacctgggct ccctgccctg    660
gcaggggctc aaagcagcca ccaagcgcca gaagtatgaa cggatcagcg agaagaagat    720
gtcaacgccc atcgaggtcc tctgcaaagg ctatccctcc gaattctcaa catacctcaa    780
cttctgccgc tccctgcggt ttgacgacaa gcccgactac tcttacctac gtcagctctt    840
ccgcaacctc ttccaccggc agggcttctc ctatgactac gtctttgact ggaacatgct    900
gaaattcggt gcagcccgga atcccgagga tgtggaccgg gagcggcgag aacacgaacg    960
cgaggagagg atggggcagc tacggggtc cgcgacccga gccctgcccc ctggcccacc    1020
cacgggggcc actgccaacc ggctccgcag tgccgccgag cccgtggctt ccacgccagc    1080
ctcccgcatc cagccggctg gcaatacttc tcccagagcg atctcgcggg tcgaccggga    1140
gaggaaggtg agtatgaggc tgcacagggg tgcgcccgcc aacgtctcct cctcagacct    1200
cactgggcgg caagaggtct cccggatccc agcctcacag acaagtgtgc catttgacca    1260
tctcgggaag tgaggagagc ccccattgga ccagtgtttg cttagtgtct tcactgtatt    1320
ttctggaatt c                                                        1331
```